(12) United States Patent
Cheng et al.

(10) Patent No.: US 9,487,556 B2
(45) Date of Patent: Nov. 8, 2016

(54) POLYCONJUGATES FOR DELIVERY OF RNAI TRIGGERS TO TUMOR CELLS IN VIVO

(71) Applicant: Arrowhead Madison Inc., Madison, WI (US)

(72) Inventors: Weijun Cheng, Middleton, WI (US); So Wong, Oregon, WI (US); Aaron M. Almeida, Madison, WI (US); David B. Rozema, Middleton, WI (US); Andrei V. Blokhin, Fitchburg, WI (US); Jeffrey C. Carlson, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 149 days.

(21) Appl. No.: 14/452,626

(22) Filed: Aug. 6, 2014

(65) Prior Publication Data
US 2015/0045573 A1    Feb. 12, 2015

Related U.S. Application Data

(60) Provisional application No. 61/863,056, filed on Aug. 7, 2013.

(51) Int. Cl.
| | | |
|---|---|---|
| *C07K 5/062* | (2006.01) | |
| *C07K 5/078* | (2006.01) | |
| *C07K 5/065* | (2006.01) | |
| *C07K 5/06* | (2006.01) | |
| *C07K 5/09* | (2006.01) | |

(52) U.S. Cl.
CPC ....... *C07K 5/06008* (2013.01); *C07K 5/06026* (2013.01); *C07K 5/06043* (2013.01); *C07K 5/06052* (2013.01); *C07K 5/06078* (2013.01); *C07K 5/06156* (2013.01); *C07K 5/0817* (2013.01)

(58) Field of Classification Search
CPC .......... C07K 5/06008; C07K 5/06156; C07K 5/06043; C07K 5/06052; C07K 5/06078; C07K 5/06026
See application file for complete search history.

(56) References Cited

U.S. PATENT DOCUMENTS

| | | | |
|---|---|---|---|
| 6,028,226 A | 2/2000 | Schapira et al. | |
| 2008/0152661 A1 | 6/2008 | Rozema et al. | |
| 2008/0287630 A1 | 11/2008 | Wakefield et al. | |
| 2009/0023890 A1 | 1/2009 | Monahan et al. | |
| 2009/0257952 A1 | 10/2009 | Cochran et al. | |
| 2011/0207799 A1 | 8/2011 | Rozema et al. | |
| 2012/0165393 A1 | 6/2012 | Rozema et al. | |
| 2012/0172412 A1* | 7/2012 | Rozema ................ | C12N 15/87 514/44 A |
| 2013/0121954 A1 | 5/2013 | Wakefield et al. | |
| 2013/0197205 A1 | 8/2013 | Chin et al. | |
| 2013/0317079 A1 | 11/2013 | Wakefield et al. | |

OTHER PUBLICATIONS

Sigma-Aldrich, Amino Acids Reference Chart, obtained from http://www.sigmaaldrich.com/life-science/metabolomics/learning-center/amino-acid-reference-chart.html on Mar. 7, 2016.*

Abrams MJ et al. "Technetium-99m-Human Polyclonal IgG Radiolabeled via the Hydrazino Nicotinamide Derivative for Imaging Focal Sites of Infection in Rats," J. Nucl. Med. 1990, vol. 31: 2022-2028.

Agard NJ et al. "A comparative study of bioorthogonal reactions with azides." ACS Chem Biol 2006, vol. 1: 644-648.

Amarzguioui et al. "An algorithm for selection of functional siRNA sequences," Biochem Biophys Res Commun 2004, vol. 316: 1050-1058.

Best MD "Click chemistry and bioorthogonal reactions: unprecedented selectivity in the labeling of biological molecules." Biochemistry 2009, vol. 48: 6571-6584.

Brooks et al. "Integrin αvβ3 Antagonists Promote Tumor Regression by Inducing Apoptosis of Angiogenic Blood Vessels" Cell 1994 vol. 79: 1157-1164.

Chalk et al. "Improved and automated prediction of effective siRNA," Biochem Biophys Res Commun 2004, vol. 319: 264-274.

Dubowchik at al. "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity" Bioconjugate Chemistry 2002, vol. 13(4): 855-69.

Dubowchik at al. "Cathepsin B-Sensitive Dipeptide Progrugs, 1. A Model Study of Structural Requirements for Efficient Release of Doxorubicin," Bioorganic Medicinal Chemistry Letters 2002 vol. 8: 3341-3346.

Frier et al. "Improved free-energy parameters for predictions of RNA duplex stability," Proc Natl Acad Sci USA 1986, vol. 83: 9373-9377.

Khvorova et al. "Functional siRNAs and miRNAs Exhibit Strand Bias," Cell 2003, vol. 115: 209-216.

Mujamdar et al. "Peptide-Mediated Targeted Drug Delivery," Medicinal Research Reviews 2010 vol. 32(3): 637-658.

Pei et al. "On the art of identifying effective and specific siRNAs," Nature Methods 2006 vol. 3(9): 670-676.

Prakasam et al. "Click Chemistry for Drug Development and Diverse Chemical-Biology Applications," Chem Rev 2013, vol. 113 (7): 4905-4979.

Quelever et al. "New β-strand macrocyclic peptidomimetic analogues containing α-(O-, S- or NH-)aryl substituted glycine residues: synthesis, chemical and enzymatic properties," Organic & Biomolecular Chemistry, 2003, vol. 1(10): 1676-1683.

(Continued)

*Primary Examiner* — Matthew Coughlin
(74) *Attorney, Agent, or Firm* — Kirk Ekena

(57) ABSTRACT

The present invention is directed compositions for delivery of RNA interference (RNAi) triggers to integrin positive tumor cells in vivo. The compositions comprise RGD ligand-targeted amphipathic membrane active polyamines reversibly modified with enzyme cleavable dipeptide-amidobenzyl-carbonate masking agents. Modification masks membrane activity of the polymer while reversibility provides physiological responsiveness. The reversibly modified polyamines (dynamic polyconjugate or conjugate) are further covalently linked to an RNAi trigger.

18 Claims, 14 Drawing Sheets

(56) References Cited

OTHER PUBLICATIONS

Reynolds et al. "Rational siRNA design for RNA interference," Nature Biotechnology 2004, vol. 22(3): 326-30. Epub Feb. 1, 2004.
Schwarz et al. "Asymmetry in the Assembly of the RNAi Enzyme Complex," Cell 2003, vol. 115: 199-208.
Seftor et al. "Role of the αvβ3 integrin in human melanoma cell invasion," Proc. Natl. Acad. Sci. USA, 1992 vol. 89:1557-1561.
Sletten EM et al. "Bioorthogonal chemistry: fishing for selectivity in a sea of functionality." Angew Chem Int Ed Engl 2009, vol. 48: 6974-6998.
Sumerlin BS et al. "Macromolecular Engineering through Click Chemistry and Other Efficient Transformations," Macromolecules 2010, vol. 43(1): 1-13.
Torchilin V "Tumor delivery of macromolecular drugs based on the EPR effect," Adv Drug Deliv Rev 2011, vol. 63 (3):131-135, Epub Mar. 18, 2010.
Turner et al. "Free Energy Increments for Hydrogen Bonds in Nucleic Acid Base Pairs," J Am Chem Soc 1987, vol. 109:3782-3785.
Ui-Tei et al. "Guidelines for the selection of highly effective siRNA sequences for mammalian and chick RNA interference," Nucleic Acids Research 2004, vol. 32(3): 936-948.
van Dijk M et al. "Synthesis and Applications of Biomedical and Pharmaceutical Polymers via Click Chemistry Methodologies" Bioconjugate Chem 2009, vol. 20(11): 2001-2016.
Wooddell et al. "Hepatocyte-targeted RNAi Therapeutics for the Treatment of Chronic Hepatitis B Virus Infection," Molecular Therapy 2013 vol. 21(5): 973-985.
Wu et al. "Proapoptotic Function of Integrin β3 in Human Hepatocellular Carcinoma Cells," Clinical Cancer Research 2009 vol. 15: 60-69.
Meldal M et al. "Cu-catalyzed azide-alkyne cycloaddition." Chem Rev 2008, vol. 108: 2952-3015.
Amblard F et al. "Cu(I)-catalyzed Huisgen azide-alkyne 1,3-dipolar cycloaddition reaction in nucleoside, nucleotide, and oligonucleotide chemistry." Chem Rev 2009, vol. 109: 4207-4220.
Written Opinion of the International Searching Authority for corresponding Application PCT/US2014/049851, 2015.

* cited by examiner

A.

Dipeptide masking agent

B.

Dipeptide masking agent linked to a polyamine.

A.

PEG-GlyGly-PABC-PNP

B.

PEG-AsnGly-PABC-PNP

C.

PEG-PheLys-PABC-PNP

D.

PEG-ValCit-PABC-PNP

E.

PEG-AlaAsn-PABC-PNP

F.

PEG-PheLys(CH$_3$)$_2$-PABC-PNP

A.

(i) N-hydroxysuccinimide (NHS), N-N'-dicyclohexylcarbodiimide (DCC), 0-20°C.

B.

(i) Triethylamine (Et₃N) in dimethylformamide (DMF).

C.

$A^1$= Gly, Glu(2PhiPr), Asn(DMCP), Phe, Ala, Val.
$A^2$=Gly, Lys(MMT), Cit, Asn(DMCP), Lys(CH₃)₂.

(i) H-A₂-OH, NaHCO₃, mixture of dimethoxyethane (DME), tetrahydrofurane (THF) and H₂O.
(ii) H-A₂-OH, NaHCO₃, DME/THF/H₂O. (iii) H-Cit-OH, NaHCO₃, THF in H₂O.

A.

A¹ = Gly, Glu(2PhiPr), Asn(DMCP), Phe, Ala, Val.
A² = Gly, Lys(MMT), Cit, Asn(DMCP), Lys(CH₃)₂

A¹ = Lys(CH₃)₂, Leu, Asn(DMCP), Cit (i) PABA, EEDQ, THF

B.

(i) Triethylamine (Et₃N) in DMF, 10h.
(ii) Fmoc-Phe-NHS, disopropylethylamine (DIEA), DMF.

(i) Et$_3$N in DMF, 10h.

PEG-A¹A²-PABA

22 a-k

(i) DIEA, DMF, 5-10h.

A.

PEG–A¹A²–PABC–PNP

23 a-k

(i) (PNP)$_2$CO, dioxane or THF, 40-60°C, 10h.

B.

PEG–A¹A²–PABC–PNP

24 a-c

(i) TFA/H$_2$O=3:1, 5°C, 2-3h.

A is a boc protected ethyl-ethoxy amino acrylate
B is a propyl methacrylate
C is a RAFT agent CPCPA (4-Cyano-4-(phenylcarbonothioylthio) pentanoic acid)
n and m are integers.
Removal of the boc protecting group after synthesis yields the amine monomers.

POLYCONJUGATES FOR DELIVERY OF RNAI TRIGGERS TO TUMOR CELLS IN VIVO

BACKGROUND OF THE INVENTION

The delivery of RNAi triggers and other substantially cell membrane impermeable compounds into a living cell is highly restricted by the complex membrane system of the cell. Drugs used in antisense, RNAi, and gene therapies are relatively large hydrophilic polymers and are frequently highly negatively charged. Both of these physical characteristics severely restrict their direct diffusion across the cell membrane. For this reason, the major barrier to RNAi trigger delivery is the delivery of the RNAi trigger across a cell membrane to the cell cytoplasm or nucleus.

Numerous transfection reagents have also been developed that achieve reasonably efficient delivery of polynucleotides to cells in vitro. However, in vivo delivery of polynucleotides using these same transfection reagents is complicated and rendered ineffective by in vivo toxicity, adverse serum interactions, and poor targeting. Transfection reagents that work well in vitro, cationic polymers and lipids, typically form large cationic electrostatic particles and destabilize cell membranes. The positive charge of in vitro transfection reagents facilitates association with nucleic acid via charge-charge (electrostatic) interactions thus forming the nucleic acid/transfection reagent complex. Positive charge is also beneficial for nonspecific binding of the vehicle to the cell and for membrane fusion, destabilization, or disruption. Destabilization of membranes facilitates delivery of the substantially cell membrane impermeable polynucleotide across a cell membrane. While these properties facilitate nucleic acid transfer in vitro, they cause toxicity and ineffective targeting in vivo. Cationic charge results in interaction with serum components, which causes destabilization of the polynucleotide-transfection reagent interaction, poor bioavailability, and poor targeting. Membrane activity of transfection reagents, which can be effective in vitro, often leads to toxicity in vivo.

For in vivo delivery, the vehicle (nucleic acid and associated delivery agent) should be small, less than 100 nm in diameter, and preferably less than 50 nm. Even smaller complexes, less that 20 nm or less than 10 nm would be more useful yet. Delivery vehicles larger than 100 nm have very little access to cells other than blood vessel cells in vivo. Complexes formed by electrostatic interactions tend to aggregate or fall apart when exposed to physiological salt concentrations or serum components. Further, cationic charge on in vivo delivery vehicles leads to adverse serum interactions and therefore poor bioavailability. Interestingly, high negative charge can also inhibit targeted in vivo delivery by interfering with interactions necessary for targeting, i.e. binding of targeting ligands to cellular receptors. Thus, near neutral vehicles are desired for in vivo distribution and targeting. Without careful regulation, membrane disruption or destabilization activities are toxic when used in vivo. Balancing vehicle toxicity with nucleic acid delivery is more easily attained in vitro than in vivo.

Rozema et al., (U.S. Patent Publications 20080152661, 20110207799, 20120165393, and 20120172412) developed conjugates suitable for in vivo delivery of polynucleotides. These conjugates featured reversible regulation of membrane disruptive activity of a membrane active polyamine using reversible physiologically labile masking. Using uncharged galactose or cholesterol as targeting ligands, Rozema et al. have shown in vivo delivery of polynucleotides to hepatocytes using these conjugates. Adaptation of these conjugates to target RNAi triggers to cancer cells would provide another therapeutic in the fight against cancer.

Integrins are a group of cell surface glycoproteins which mediate cell adhesion. Integrins are heterodimers composed of α and β polypeptide subunits. Currently eleven different α subunits and six different β subunits have been identified. The various α subunits combine with various β subunits to form distinct integrins. The $\alpha_v\alpha_3$ integrin (vitronectin receptor) has been shown to play a role in tumor metastases, solid tumor growth (neoplasia), and tumor angiogenesis. The integrin $\alpha_v\beta_3$ plays an important role in angiogenesis. It is expressed on tumoral endothelial cells as well as on some tumor cells. Seftor et al. (Proc. Natl. Acad. Sci. USA, Vol. 89 (1992) 1557-1561), for example, have shown a role for $\alpha_v\beta_3$ integrin in melanoma cell invasion. Brooks et al. (Cell, Vol. 79 (1994) 1157-1164) demonstrated that systemic administration of $\alpha_v\beta_3$ antagonists caused dramatic regression of various histologically distinct human tumors.

Tumor cell expression of the integrins $\alpha_v\beta_3$ is correlated with disease progression in various tumor types. $\alpha_v\beta_3$ integrin is widely expressed on blood vessels of human tumor biopsy samples but not on vessels in normal tissues. In breast cancer, overexpression of $\alpha_v\beta_3$ integrin is associated with bone metastasis and induces increased tumor growth and invasion in response to osteopontin. In glioblastoma, $\alpha_v\beta_3$ integrin is overexpressed at the invasive margins of the tumor and levels of fibronectin are increased, which is associated with enhanced cell motility and apoptosis resistance. In pancreatic tumor, the increased expression of $\alpha_v\beta_3$ integrin is associated with increased activation of MMP-2 and lymph node metastasis. In prostate carcinoma cell, $\alpha_v\beta_3$ integrin is expressed resulting in metastasis to bone because of an association between integrins and processes of attachment and migration involving laminin, fibronectin, and osteopontin.

$\alpha_v\beta_3$ integrins bind to a number of Arg-Gly-Asp (RGD) containing matrix macromolecules. The RGD peptide sequence has been linked to various other compounds to provide $\alpha_v\beta_3$ integrin binding. Therefore, RGD peptides have been examined for targeting of compounds to $\alpha_v\beta_3$ integrin positive tumors. However, in addition to relatively low affinity, many RGD peptides are also relatively non-selective for RGD-dependent integrins. For example, most RGD peptides which bind to $\alpha_v\beta_3$ also bind to $\alpha_v\beta_5$, $\alpha_v\alpha_1$, and $\alpha_{IIb}\beta_3$ integrins.

SUMMARY OF THE INVENTION

We describe compositions for delivering RNAi triggers to tumor cells in mammals in vivo comprising: integrin-targeted reversibly masked membrane active polyamines covalently linked to RNAi triggers. The described compositions deliver RNAi triggers to tumor cells where the RNAi triggers interact with the cells' endogenous RNA interference pathways to inhibit expression of target genes.

The invention features a composition for delivering an RNA interference (RNAi) trigger to a tumor cell in vivo comprising: a masked amphipathic membrane active polyamine (delivery polymer) and an RNAi trigger wherein the RNAi trigger is covalently linked to the delivery polymer. The delivery polymer comprises an amphipathic membrane active polyamine masked by reversible modification of polymer amines with one or more RGD dipeptide masking agents and optionally one or more PEG dipeptide masking agents such that at least 50% or at least 80% of the polymer amines are modified. A preferred linkage for covalent attachment of the delivery polymer to the RNAi trigger is a physiologically labile linkage. In one embodiment, this linkage is orthogonal to the dipeptide masking agent linkage. The delivery conjugate is administered to a mammal in a pharmaceutically acceptable carrier or diluent.

In a preferred embodiment, we describe a composition comprising: an amphipathic membrane active polyamine covalently linked to: a) a plurality of RGD ligands and steric stabilizers via dipeptide-amidobenzyl-carbamate reversible physiologically labile linkages; and b) one or more RNAi triggers via one or more labile covalent linkages. In one embodiment, the dipeptide-amidobenzyl-carbamate is orthogonal to the labile covalent linkage. The RNAi trigger-polymer conjugate is administered to a mammal in a pharmaceutically acceptable carrier or diluent.

In a preferred embodiment, a reversibly masked membrane active polyamine (delivery polymer) comprises: an amphipathic membrane active polyamine reversibly modified by reaction of amines of the polyamine with RGD masking agents and steric stabilizer masking agents. Reaction of a polymer amine with a masking agent reversibly modifies the amine to form a reversible physiologically labile covalent linkage. An amine is reversibly modified if cleavage of the modifying group restores the amine. Reversible modification of the membrane active polyamine reversibly inhibits membrane activity of the membrane active polyamine, inhibits interaction of the polyamine with serum components thereby providing increased circulation properties, and targets the polyamine to a tumor cell in vivo. In the masked state, the reversibly masked membrane active polyamine does not exhibit membrane disruptive activity. Membrane activity inhibition and/or in vivo targeting of the membrane active polyamine requires modification of >50% of the polymer amines. Reversible modification of more than 50%, more than 55%, more than 60%, more than 65%, more than 70%, more than 75%, more than 80%, more than 85%, or more than 90% of the amines on the polyamine with masking agents may be required to form an optimal delivery polymer.

A modified polymer amine of the delivery polymers of the invention is represented by:

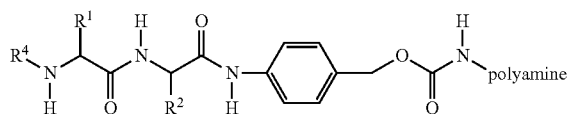

wherein $R^4$ comprises an RGD ligand or steric stabilizer and $R^1$ and $R^2$ are amino acid side chains. $R^1$ is preferably a side group of a hydrophobic amino acid. A preferred hydrophobic amino acid is an alanine. $R^2$ is preferably a side chain of a hydrophilic uncharged amino acid at neutral pH. A preferred hydrophilic uncharged amino acid is a citrulline. In vivo enzymatic cleavage after the dipeptide, between the amino acid and the amidobenzyl group, by removes $R^4$ from the polymer and initiates an elimination reaction in which the amidobenzyl-carbamate undergoes a spontaneous rearrangement that results in regeneration of the polymer amine.

The delivery polymer is further covalently linked to the RNAi trigger. In one embodiment, the RNAi trigger is linked to the delivery polymer via a physiologically labile bond. In a preferred embodiment, the labile bond connecting the RNAi trigger to the delivery polymer is orthogonal to the labile bond connected the masking agents to the polyamine.

Thus, conjugates of the invention comprise: an RNAi trigger covalently linked to a reversibly modified amphipathic membrane active polyamine having the general form represented by:

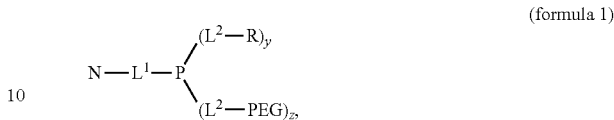

(formula 1)

wherein N comprises an RNAi trigger, $L^2$ is a reversible physiologically labile linkage such as $A^1A^2$-amidobenzyl-carbamate, P comprises an amphipathic membrane active polyamine, R comprises an RGD ligand, each as defined herein, PEG comprises a polyethylene glycol or other steric stabilizer, $L^1$ is a physiologically labile linker, y is an integer greater than zero and z is an integer greater than zero (0), wherein the value of the sum of y and z is greater than 50% of the number of amines present on polyamine P as determine be the number of amines in the unmodified membrane active polyamine.

The compounds according to the present invention can be generally obtained using methods known to the person of ordinary skill in the art of organic or medicinal chemistry. Further objects, features, and advantages of the invention will be apparent from the following detailed description when taken in conjunction with the accompanying drawings.

In a preferred embodiment, polymer modifications $-L^2-R$ and $-L^2$-PEG have the general form:

R-$A^1A^2$-amidobenzyl-carbamate- (formula 2a)

and

PEG-$A^1A^2$-amidobenzyl-carbamate- (formula 2b).

wherein $A^1A^2$ is a dipeptide, $A^1$ is an amino acid, and $A^2$ is an amino acid. An RGD ligand may be linked to the dipeptide via a linker such as a PEG linker. A preferred steric stabilizer is a polyethylene glycol (PEG). $A^1$ is preferably a hydrophobic amino acid. $A^2$ is preferably a hydrophilic uncharged amino acid. $A^1$ and $A^2$ are preferably linked via an amide bond. A preferred amidobenzyl group is a p-amidobenzyl group. The carbamate is formed by reaction of a carbonate with a polymer amine. A preferred carbonate is an activated amine reactive carbonate. The $A^1A^2$-amidobenzyl-carbamate linkage is stable until the dipeptide is cleaved in vivo by an endogenous protease, thus cleaving the steric stabilizer or RGD ligand from the polyamine. Following enzymatic cleavage after the dipeptide (between $A^2$ and the amidobenzyl), the amidobenzyl-carbamate undergoes a spontaneous rearrangement which results in regeneration of the polymer amine.

In one embodiment, the RGD ligand is linked to the dipeptide using a linker that aids in attachment of the RGD ligand to the dipeptide and in solubility of the masking agent. A preferred asking agent has the general form: RGD ligand-PEG1-diaryl hydrazone-PEG2-dipeptide-amidobenzyl-carbonate. Each of the components can be linked using standard methods in the art, such as formation of amide linkages. The diaryl hydrazone can be formed by reaction of a HyNic (hydrazino-nicotinamide) group with an aryl aldehyde. PEG1 comprises $(CH_2—CH_2—O)_n$ and PEG2 comprises $(CH_2—CH_2—O)_m$. n and m are independently integers greater than or equal to 4 and the sum of n+m is 12-48. The PEG groups aid in solubility and presentation of the RGD ligand, thereby imrpoving tumor targeting of the modified polyamine. Surprisingly, the diaryl hydrazone also improves in vivo function of the modified polyamine. In one embodiment, an aryl aldehyde-PEG2-dipeptide-amidobenzyl-carbonate is first reacted with a polyamine to form an aryl aldehyde-PEG2-dipeptide-amidobenzyl-carbamate-polyamine. This compound is then reacted with an RGD ligand-PEG1-HyNic to from: RGD ligand-PEG1-diaryl hydrazone-PEG2-dipeptide-amidobenzyl-carbomate-polyamine.

DETAILED DESCRIPTION OF THE INVENTION

Figure 1:
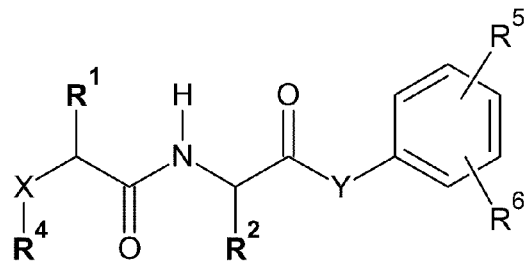
FIG. 1. Illustrations showing the structure of (A) a dipeptide masking agent or (B) a dipeptide masking agent linked to a polyamine: $R^1$ and $R^2$ are the R groups of amino acids, $R^4$ comprises an RGD ligand or a steric stabilizer, —X— is —NH—, —O—, or —CH$_2$—, —Y— is —NH— or —O—, —$R^5$ is at position 2, 4, or 6 and is —CH$_2$—O—C(O)—O—Z wherein Z carbonate, and —$R^6$ is independently hydrogen, alkyl, or halide at each of positions 2, 3, 4, 5, or 6 except for the position occupied by $R^5$.
Figure 1:
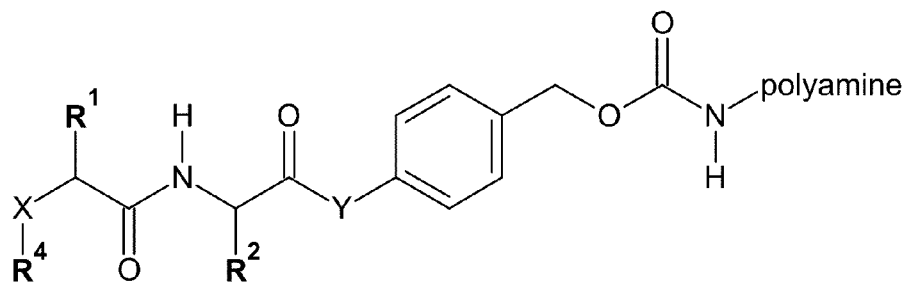
Figure 2:
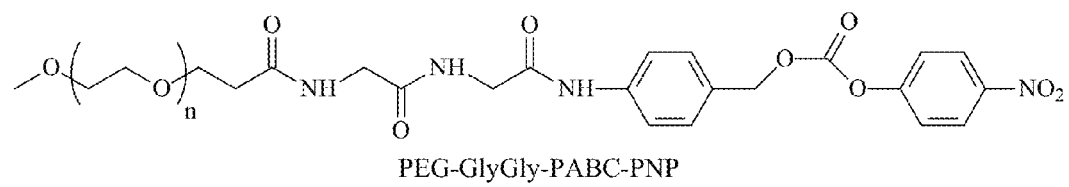
FIG. 2. Illustration showing the structures of various PEG dipeptide masking agents: (A) PEG-GlyGly-PABC-PNP, (B) PEG-AsnGly-PABC-PNP, (C) PEG-PheLys-PABC-PNP, (D) PEG-ValCit-PABC-PNP, (E) PEG-AlaAsn-PABC-PNP, and (F) PEG-PheLys(CH3)2-PABC-PNP.
Figure 2:
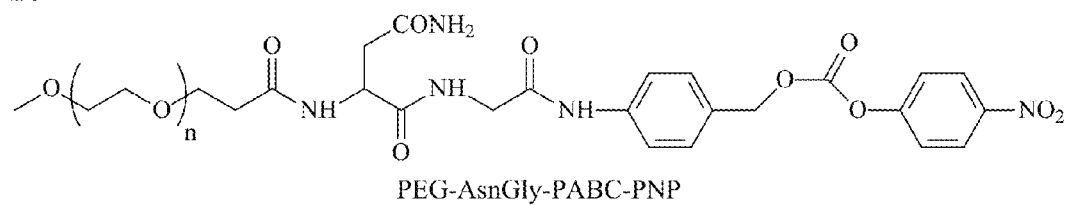
Figure 2:
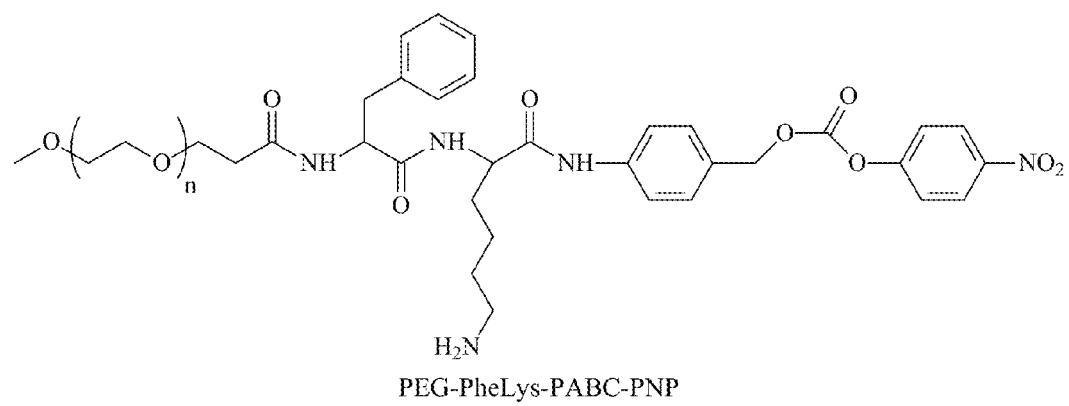
Figure 2:
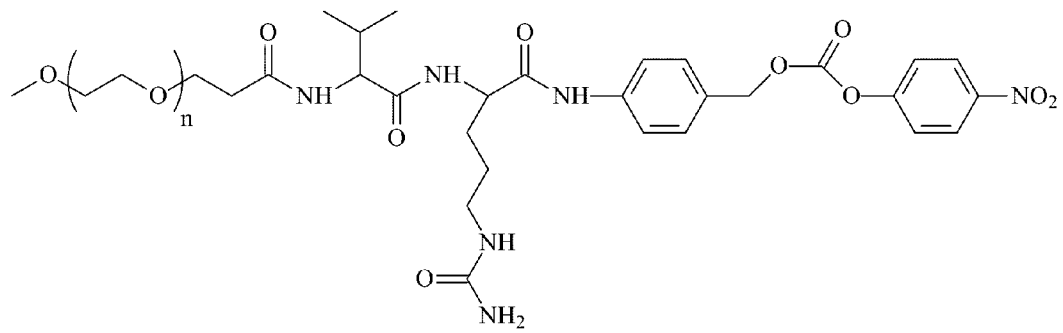
Figure 2:
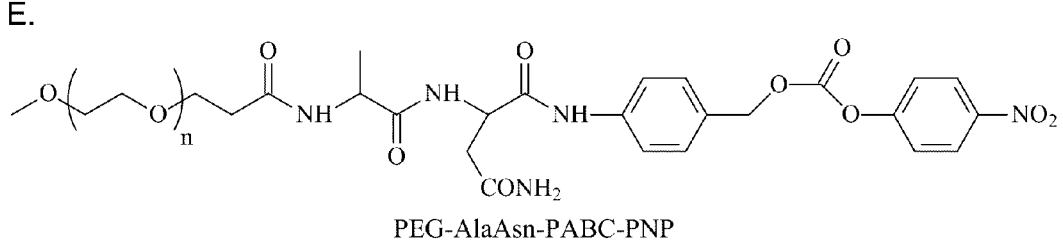
Figure 2:
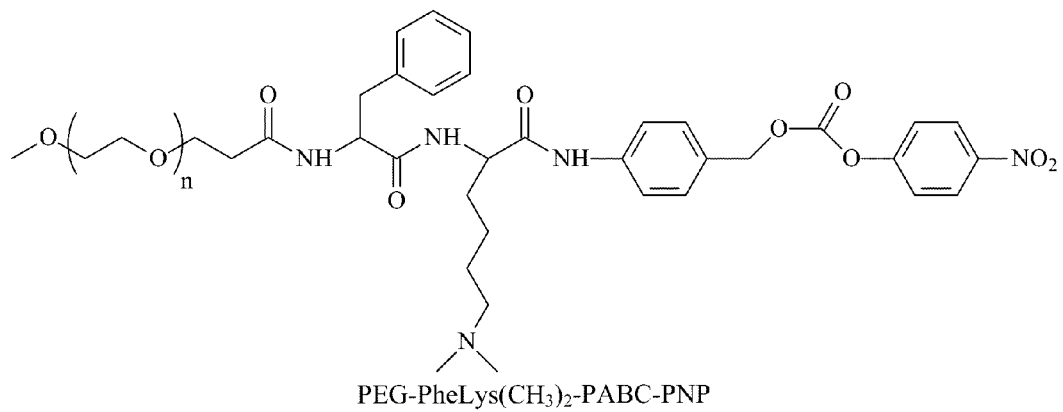

The present invention provides conjugates and methods for delivering RNA interference (RNAi) triggers into integrin expressing tumor cells in vivo. The described conjugates comprise integrin-targeted reversibly modified membrane active polyamines covalently linked to the RNAi trigger to be delivered. Integrin targeting is provided by RGD ligands described herein. Reversible modification of the membrane active polyamine is provided by RNA ligand and steric stabilizer peptidase cleavable masking agents described herein. The peptidase cleavable linkages are stable to hydrolysis in absence of protease, and provide extended stability in storage and in in vivo circulation. Improved (longer) half-life in circulation facilitates widening of the window of opportunity for RGD ligand-mediated accumulation in tissue, such as tumor tissue. In vivo delivery of RNAi triggers is useful for therapeutic inhibition (knockdown) of gene expression.

The invention includes conjugate delivery systems of the general structure:

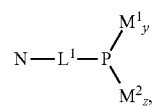

wherein N is an RNAi trigger, $L^1$ is a physiologically labile linkage, P is an amphipathic membrane active polyamine, $M^1$ comprises an RGD ligand linked to P via a dipeptide-amidobenzyl-carbamate linkage (RGD masking agent), and $M^2$ comprises a steric stabilizer linked to P via a dipeptide-amidobenzyl-carbamate linkage (PEG masking agent). y and z are each integers greater than zero provided the value of y+z has a value greater than 50%, greater than 60%, greater than 70%, greater than 80% or greater than 90% of the number of primary amines on polyamine P, as determined by the quantity of amines on P in the absence of any masking agents. In its unmodified state, P is a membrane active polyamine. Delivery polymer $M^1_y$-P-$M^2_z$ is not membrane active. Reversible modification of P primary amines, by attachment of $M^1$ and $M^2$, reversibly inhibits or inactivates membrane activity of P. It is noted that some small amphipathic membrane active polyamine, such as melittin peptide, contain as few as 3-5 primary amines. Modification of a percentage of amines is meant to reflect the modification of a percentage of amines in a population of polymers. Upon cleavage of $M^1$ and $M^2$, amines of the polyamine are regenerated thereby reverting P to its unmodified, membrane active state.

For tumor deliver, y has a value equal to 2-20% of the number of primary amines on polymer P. More preferably, y has a value equal to 2-10% of the number of primary amines on polymer P. z therefore has a value equal to 80-98% of the number of primary amines on polymer P. The ratio y (RGD):z (steric stabilizer) is preferably about 1-12:50 and more preferably about 1:20.

In the masked state, the reversibly masked membrane active polyamine does not exhibit membrane disruptive activity. Reversible modification of more than 50%, more than 55%, more than 60%, more than 65%, more than 70%, more than 75%, more than 80%, more than 85%, or more than 90% of the amines on the polyamine with dipeptide masking agents may be required to inhibit membrane activity and provide cell targeting function, i.e. form a reversibly masked membrane active polymer (delivery polymer).

In one embodiment, the RNAi trigger is linked to the delivery polymer of the invention via a physiologically labile covalent linkage. By using a physiologically labile linkage, the RNAi trigger can be cleaved from the polymer, releasing the RNAi trigger to engage in functional interactions with cell components.

Masking is accomplished through reversible attachment of the described masking agents to the membrane active polyamine to form a reversibly masked membrane active polymer, i.e. a delivery polymer. In addition to inhibiting membrane activity, the masking agents shield the polymer from non-specific interactions, reduce serum interactions, increase circulation time, and/or provide cell-specific interactions, i.e. targeting.

It is an essential feature of the masking agents that, in aggregate, they inhibit membrane activity of the polymer. Masking agents may shield the polymer from non-specific interactions (reduce serum interactions, increase circulation time). The membrane active polyamine is membrane active in the unmodified (unmasked) state and not membrane active (inactivated) in the modified (masked) state. A sufficient number of masking agents are linked to the polymer to achieve the desired level of inactivation. The desired level of modification of a polymer by attachment of masking agent(s) is readily determined using appropriate polymer activity assays. For example, if the polymer possesses membrane activity in a given assay, a sufficient level of masking agent is linked to the polymer to achieve the desired level of inhibition of membrane activity in that assay. Masking requires modification of ≥50%, ≥60%, ≥70%, ≥80% or ≥90% of the primary amine groups on a population of polymer, as determined by the quantity of primary amines on the polymer in the absence of any masking agents. It is desirable that the masked polymer retain aqueous solubility.

It is an essential feature of the RGD masking agents that, in aggregate, they target the delivery polymer to $\alpha_v\beta_3$ integrin positive tumor cells. A sufficient number of masking agents are linked to the polymer to achieve the tumor cellular targeting. Targeting may require modification of about 2% to about 20%, about 2% to about 10%, or about 3% to about 6% of the primary amine groups on a population of polymer, as determined by the number of primary amines on the polymer in the absence of any masking agents.

In one embodiment, an RGD masking agent suitable for modification of a polyamine to form an integrin-targeted delivery polymer comprises: an RGD ligand covalently linked to a dipeptide-amidobenzyl-carbonate (RGD dipeptide masking agent). Similarly, a steric stabilizer dipeptide masking agent suitable for modification of a polyamine to form an integrin-targeted delivery polymer comprises: a steric stabilizer covalently linked to a dipeptide-amidobenzyl-carbonate. The masking agents have the general form:

(R or PEG)-A$^1$A$^2$-amidobenzyl-carbonate.

wherein R comprises an RGD ligand, PEG comprises a polyethylene glycol of other steric stabilizer, A$^1$A$^2$ is a dipeptide containing a first amino acid A$^1$ and a second amino acid A$^2$, and carbonate is an activated amine-reactive carbonate. Reaction of the masking agent carbonate with a polymer amine yields a carbamate linkage. The RNA ligand or steric stabilizer may be attached to the dipeptide prior to reaction of the carbonate with the polymer amine or after formation of the carbamate linkage. The masking agent is stably linked to the polymer until the dipeptide is cleaved in vivo by an endogenous protease, thus cleaving the RGD ligand or steric stabilizer from the polyamine. Following enzymatic cleavage after the dipeptide (between A$^2$ and the amidobenzyl), the amidobenzyl-carbamate undergoes a spontaneous rearrangement which results in regeneration of the polymer amine. An RGD ligand may be linked to the dipeptide via a linker such as a PEG linker. A preferred steric stabilizer masking agent is uncharged. A preferred uncharged steric stabilizer is a polyethylene glycol (PEG). A preferred dipeptide consists of a hydrophobic amino acid linked (A$^1$) to a hydrophilic uncharged amino acid (A$^2$) via an amide bond. A preferred amidobenzyl group is a p-amidobenzyl group. A preferred carbonate is an activated amine reactive carbonate.

Masking agents suitable for formation of integrin-targeted delivery polymers of the invention have the general structure:

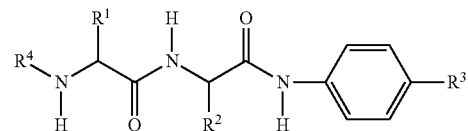

wherein R$^4$ comprises an RGD ligand or steric stabilizer, R$^3$ comprises an amine reactive carbonate moiety, and R$^1$ and R$^2$ are amino acid side chains. R$^1$ is preferably a side group of a hydrophobic amino acid. A preferred hydrophobic amino acid is an alanine. R$^2$ is preferably a side chain of a hydrophilic uncharged amino acid. A preferred hydrophilic uncharged amino acid is a citrulline. A preferred activated carbonate is a para-nitrophenol. However, other amine reactive carbonates known in the art are readily substituted for the para-nitrophenol. Reaction of the activated carbonate with an amine connects the RGD ligand or steric stabilizer to the membrane active polyamine via a peptidase cleavable dipeptide-amidobenzyl carbamate linkage as represented by:

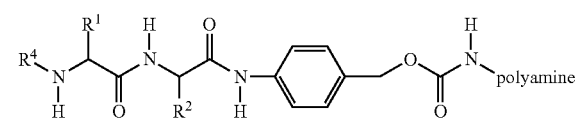

wherein R$^4$, R$^1$, and R$^2$ are as described above. Enzyme cleavage after the dipeptide, between the amino acid and the amidobenzyl group, removes R$^4$ from the polymer and triggers an elimination reaction in which the amidobenzyl-carbamate undergoes a spontaneous rearrangement which results in regeneration of the polymer amine.

In another embodiment, attachment of the RGD ligand to the polyamine via a reversible physiologically labile linkage is achieved by first reversibly modifying the amine with a dipeptide-amidobenzyl-carbonate have the general structure:

(formula 3)

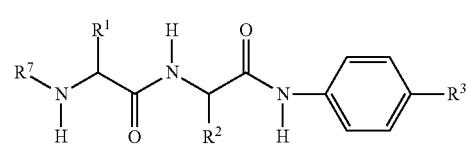

wherein $R^7$ comprises a reactive group suitable for reaction with an RGD ligand-containing moiety and less amine reactive than the carbonate of $R^3$. $R^1$, $R^2$, and $R^3$ are as defined above. In one embodiment, $R^7$ further comprises a PEG linking moiety (also termed PEG2 herein). We have found that inserting a PEG linking moiety between the dipeptide and the reactive group improves solubility and in vivo function of the assembled RGD masking agent. A preferred PEG linking moiety is a $(CH_2-CH_2-O)_{4-44}$. After modification of a polymer amine with the reactive group ($R^7$)-containing dipeptide-amidobenzyl-carbonate, the RGD ligand-containing moiety is covalently linked via reaction with reactive group $R^7$. Exemplary reactive group moieties suitable linking the dipeptide and the RGD ligand-containing moiety include, but are not limited to: HyNic and aldehyde (including aryl aldehyde), "Click" chemistry crosslinkers (certain azides and alkynes). An exemplary molecule of formula 3 is a (4-formylbenzaldehyde)-PEG-Ala-Cit-ara-aminobenzyl carbonate.

Dipeptides of the dipeptide masking agents, represented herein as $A^1A^2$ (or AA), are dimers of amino acids connected via amide bonds. Amino acids, including α and β amino acids are well known in biology and chemistry and are molecules containing an amine group, a carboxylic acid group and a side-chain that varies between different amino acids. A preferred amino acid is an L α-amino acid having the generic formula $H_2NCHRCOOH$, where R ($R^1$ and $R^2$ of formula 3) is an organic substituent or side group. A preferred L α amino acid is an uncharged naturally occurring amino acid. In a preferred dipeptide, $A^1$ is a hydrophobic amino acid and $A^2$ is an uncharged hydrophilic amino acid. A preferred hydrophobic amino acid is phenylalanine, valine, isoleucine, leucine, alanine, or tryptophan. A preferred uncharged hydrophilic amino acid is asparagine, glutamine, or citrulline. A more preferred hydrophobic amino acid is alanine or phenylalanine. A more preferred uncharged hydrophilic amino acid is citrulline. While dipeptides are preferred, it is possible to insert additional amino acids between $A^1$ and R. It is also possible to use a single amino acid instead of a dipeptide by eliminating amino acid $A^1$. Any natural amino acids used in the present invention are referred to herein by their common abbreviations.

In a preferred embodiment, an amphipathic membrane active polyamine is reversibly modified by reaction with a described dipeptide-amidobenzyl-carbonate masking agent to yield a membrane inactive delivery polymer. The dipeptide masking agents shield the polymer from non-specific interactions, increase circulation time, enhance specific interactions, inhibit toxicity, or alter the charge of the polymer.

Reversibly masked polymers of the invention comprise the structure:

wherein:
X is —NH—, —O—, or —CH$_2$—
Y is —NH— or —O—
$R^1$ is preferably —(CH$_2$)$_k$-phenyl (k is 1, 2, 3, 4, 5, 6; k=1 phenylalanine), —CH—(CH$_3$)$_2$ (valine), —CH$_2$—CH—(CH$_3$)$_2$ (leucine), —CH(CH$_3$)—CH$_2$—CH$_3$ (isoleucine), —CH$_3$ (alanine), or (tryptophan);

$R^2$ is preferably hydrogen (glycine), —(CH$_2$)$_3$—NH—C(O)—NH$_2$ (citrulline), —CH$_2$—C(O)—NH$_2$ (asparagine), —(CH$_2$)$_2$—C(O)—NH$_2$ (glutamine), —(CH$_2$)$_4$—N—(CH$_3$)$_2$ (lysine(CH$_3$)$_2$), —(CH2)$_k$—C(O)—NH$_2$; (k is 1, 2, 3, 4, 5, 6), —CH$_2$—C(O)—NR'R" (aspartic acid amide), —(CH$_2$)$_2$—C(O)—NR'R" (glutamic acid amide), —CH$_2$—C(O)—OR (aspartic acid ester), or —(CH$_2$)$_2$—C(O)—OR (glutamic acid ester), wherein R' and R" are alkyl groups
$R^4$ comprises an RGD ligand or a polyethylene glycol; and
the polyamine is an amphipathic membrane active polyamine.

While the structure above indicates a single dipeptide masking agent linked to the polymer, in practice of the invention, 50% to 100% of polymer amines are modified by dipeptide masking agents.

In a preferred embodiment, a reversibly masked polymer of the invention comprises the structure:

wherein $R^1$, $R^2$, $R^4$ and polyamine as described above.

Reversibly masked polymers of the invention can be formed by reaction of dipeptide masking agents of the invention with amines on the polymer. Dipeptide masking agents of the invention have the structure:

wherein:
X, Y, $R^1$, $R^2$, and $R^4$ are as described above
$R^5$ is at position 2, 4, or 6 and is —CH$_2$—O—C(O)—O—Z wherein Z is -Halide, -continued

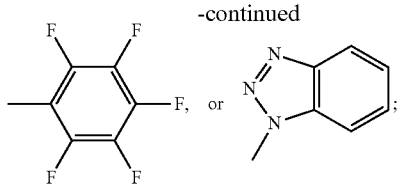

and

R[6] is independently hydrogen, alkyl, —(CH$_2$)$_n$—CH$_3$ (wherein n=0-4), —(CH$_2$)—(CH$_3$)$_2$, or halide at each of positions 2, 3, 4, 5, or 6 except for the position occupied by R[5].

In a preferred embodiment, X is —NH—, Y is —NH—, R[4] comprises an RGD ligand or PEG group, R[5] is at position 4, and R[6] is hydrogen as shown by:

(formula 4)

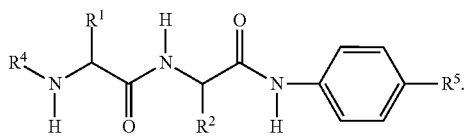

In another embodiment, R[4] of formula 4 is R[8]—(O—CH$_2$—CH$_2$)$_s$—O—Y[1]—, wherein: R[8] is hydrogen, methyl, or ethyl; and s is an integer from 1 to 150, and Y[1] is a linker suitable in the art for connecting a PEG group to the dipeptide. Suitable linkers Y[1] include, but are not limited to: —(CH$_2$)$_{1-3}$—C(O)—, —Y[2]—NH—C(O)—(CH$_2$)$_2$—C(O)— (wherein Y[2] is —(CH$_2$)$_3$—), and —C(O)—N—(CH$_2$—CH$_2$—O)—CH$_2$—CH$_2$— (p is an integer from 1 to 20).

As used herein, an RGD ligand comprises a zwitterionic RGD peptide or RGD mimic <1500 kDa in size that binds to (has affinity for) the alpha v/beta 3 (αvβ3 or α$_v$β$_3$) integrin.

As used herein, an RGD peptide comprises an arginine-glycine-aspartate tripeptide. An RGD peptide may further comprise additional amino acids amino or carboxy terminal to the RGD sequence. If additional amino acids are present, the contiguous peptide sequence constitutes the RGD peptide. An RGD peptide may be conformationally constrained. Conformational constraint is typically accomplished by cyclization of the peptide, such as by adding Cysteine amino acids amino and carboxy terminal of the RGD sequence and forming a disulfide bond between the cysteine thiols. A preferred constrained RGD peptide comprises the amino acid sequence: X$_{n1}$C$_m$X$_{n2}$CX$_{n3}$RGDX$_{n4}$CX$_{n5}$C$_m$X$_{n6}$ (SEQ ID 1) wherein X is a naturally occurring amino acid, m is zero (0) or one (1), and n1-n6 are independently 0, 1, 2, or 3. If present (n=1, 2, or 3), the one or more amino acids at each X are independent of the selection of amino acid(s) at the other positions. In one embodiment, m, n1, n2, and n5 are each one (1), and n3, n4, and n6 are each zero (0). In another embodiment, m is one (1), X$_{n1}$ is Alanine, X$_{n2}$ is Aspartate, X$_{n5}$ is Phenylalanine, and n3, n4, and n6 are each zero (0) (ACDCRGDCFC, SEQ ID 2). An RGD peptide may have non-peptide components linked to the RGD amino acid sequence. For example, the amino terminus of the peptide may be acylated or a linker may be attached to the carboxy terminus of the peptide. In another embodiment, m is one (1), X$_{n1}$ is acylated Alanine, X$_{n2}$ is Aspartate, X$_{n5}$ is Phenylalanine, n3, n4, and n6 are each zero (0).

As used herein, an RGD mimic is a non-peptide synthetic molecule other than an RDG peptide that biologically mimics the active determinants of an RGD peptide, an integrin-binding RGD portion of a integrin binding protein, or an α$_v$β$_3$ integrin binding RGD motif. An RGD mimic may contain one or two naturally occurring amino acids linked via amide bonds. An RGD mimetic may be a modified peptide, contain non-standard amino acids or non-standard amino acid side chains. An RGD mimic may have a peptide backbone represented by the structure:

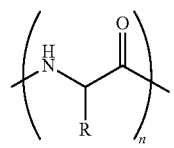

wherein n is an integer.

In one embodiment, an RGD ligand comprises a guanidinium group linked to a glycine-aspartate dipeptide via an amide bond. Guanidinium groups of the invention have the structure represented by:

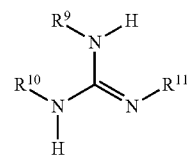

wherein R[9] and R[10] are independently hydrogen or alkyl and may by connected to form a ring, and R[11] is a linker connecting the guanidinium group to the glycine-aspartate dipeptide. The guanidinium group includes both the structure represented above and its resonance structures. A preferred linker is:

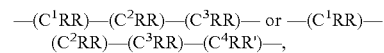

wherein: a) each R is independently optional and if present is independently hydrogen, alkyl, or aryl, b) R' is hydrogen, alkyl, aryl, or NH$_2$, and c) C[1], C[2], and C[3] may be linked by single bonds, a single bond and a double bond, or aromatic bonds.

While not explicitly shown in the structure RGD ligand structures presented herein, is it well known and understood that guanidinium groups are positively charged at neutral or near neutral pH (pH 6.5-7.5):

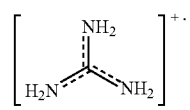

Similarly, while not explicitly shown in the RGD ligand structures presented herein, is it well known and understood that amino acid aspartic acid is negatively charged at neutral or near neutral pH (pH 6.5-7.5):

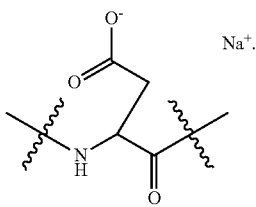 [SMILES: *NC(CC(=O)[O-])C(*)=O]

A phenoxy group attached to the aspartate amino acid of the RGD ligand was found to improve targeting the polyamine to tumor cells in vivo. A preferred RGD ligand comprises a quanidinium-glycine-aspartate-4-aminophenoxy compound. A preferred quanidinium-glycine-aspartate-4-aminophenoxy compound comprises the structure represented by:

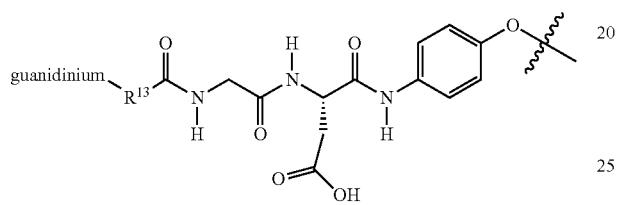

wherein $R^{13}$ is:

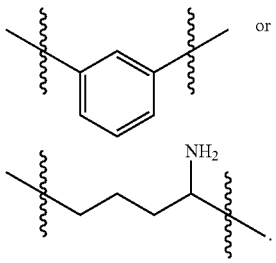

A preferred guanidinium is

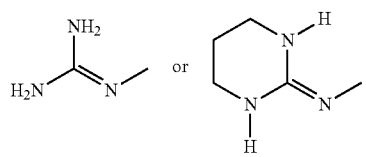

and their resonance structures.

In another embodiment, an RGD ligand-containing moiety comprises the structure represented by:

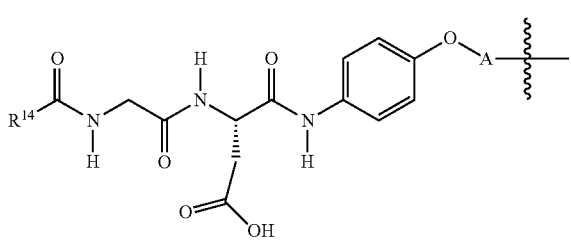

wherein:
$R^{14}$ is

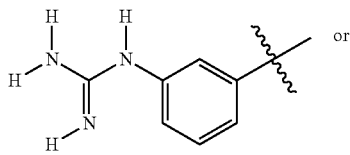

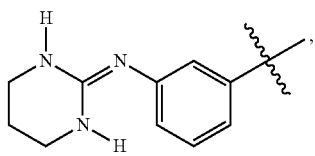

and

A comprises a linker. The linker connects the RGD mimic to another molecule such as a dipeptide amidobenzyl-carbonate, provides for increased solubility, or provides a means for covalent linkage to another molecule.

In one embodiment, linker A comprises:

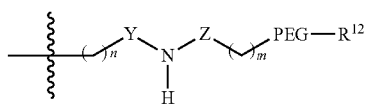

wherein
n is 0, 1, 2, or 3,
Y is absent or

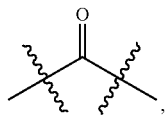 [SMILES: *C(*)=O]

Figure 13:
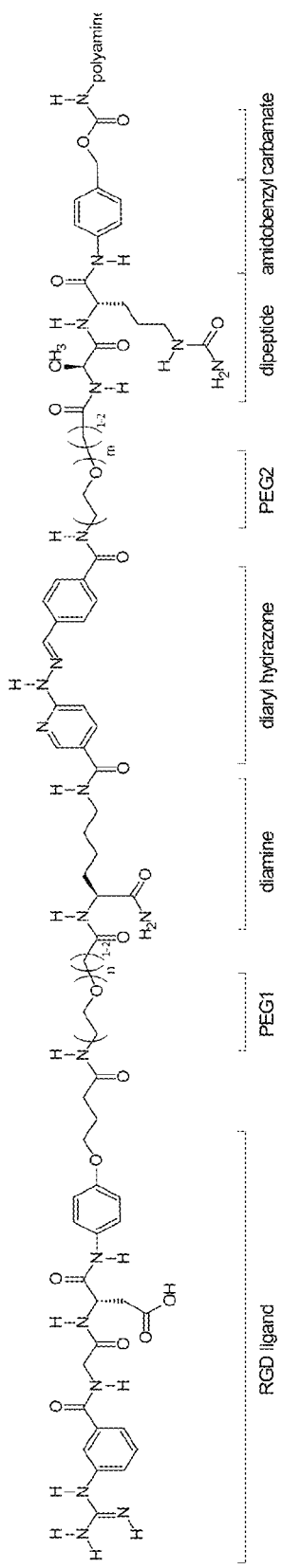
FIG. 13. Illustration showing a polyaminer modified by one example of an RGD masking agent: RGD ligand-PEG1-diamine-diaryl hydrazone-PEG2-dipeptide-amidobenzyl-carbomate-polyamine. Atoms not explicitly indicated as being part of a unit by the ∟⎯⎯⏌ (i.e. RGD ligand, PEG1, etc.) are considered linking atoms and may be considered to be part of the labeled unit to either side.

Z is absent,

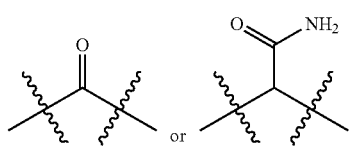

m is 0, 1, 2, 3, or 4, and
PEG (PEG1 in FIG. 13) is $(CH_2-CH_2-O)_{4-44}$, and
$R^{12}$ comprises a reactive group capable of reacting with $R^7$ to from a covalent linkage.

Each of the separate components, PEG, reactive group, etc. can be combined (covalently linked) using methods readily available in the art, including, but not limited to formation of amide bonds. In one embodiment, reactive group $R^{12}$ can be linked to the PEG via a diamine such as a lysine. The carboxyl group of the lysine can be attached to a solid support to aid is synthesis of the R GD ligand. The terminal and ε-amines are then used to link the PEG group and reactive group. The reactive group $R^{12}$ is selected to readily reactive with reactive group $R^7$ of formula 3 to form a covalently linkage. Pairs of reactive groups suitable for use with $R^{12}$ and $R^7$ may be selected from the pairs comprising: azide and phosphine, azide and alkyne, nitrone and alkyne, tetrazine and octane, tetrazine and cyclopropene, tetrazine and isonitrile, di-ene and alkene, aldehyde and hydrazine, aldehyde and aminooxy, aldehyde and hydrazide, ketone and hydrazine, ketone and aminooxy, and ketone and hydrazide. A preferred reactive group is:

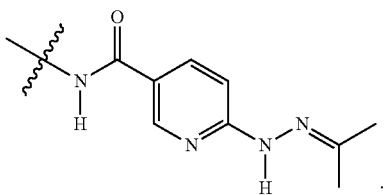 [SMILES: *NC(=O)c1ccc(NN=C(C)C)nc1]

In a preferred embodiment, an RGD ligand-containing moiety comprises the structure represented by:

wherein $R^{14}$ is a guanidinium-containing moiety as defined above, A' comprises a PEG-containing linker, $R^1$ is preferably a side group of a hydrophobic amino acid, $R^2$ is preferably a side chain of a hydrophilic uncharged amino acid (at neutral pH), and $R^3$ is an amine-reactive carbonate. In one embodiment, linker A' comprises a PEG group having 4-48 ethoxy units. In another embodiment, linker A' comprises a first PEG (PEG1) group having 4-44 ethylene units and a second PEG (PEG2) group having 4-44 ethylene groups separated by a diacyl hydrazine or other linkage chemistry. In one embodiment, the diacyl hydrazone is linked to the first PEG group via a diamine, such as a lysine. The diaryl hydrazone can be formed by reaction of a HyNic (hydrazino-nicotinamide) group with an aryl aldehyde.

In another embodiment, the linker A' comprises linkages form be the reaction of: an azide with a phosphine, an azide with an alkyne, a nitrone with an alkyne, a tetrazine with an octene, a tetrazine with a cyclopropene, a tetrazine with an isonitrile, a di-ene with an alkene, an aldehyde with a hydrazine, an aldehyde with an aminooxy, an aldehyde with

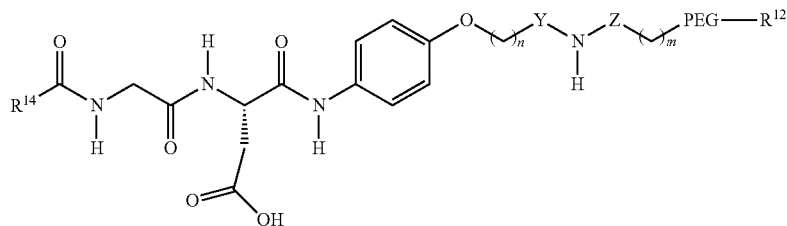

wherein: $R^{14}$, n, Y, Z, m, PEG, and $R^{12}$ are each as defined above.

The reactive group $R^{12}$ can be used to attached the RGD ligand to a reversible physiologically labile linker such as a dipeptide linker to yield an RGD masking agent. In one embodiment, an RGD masking agent comprises the structure represented by:

a hydrazide, a ketone with a hydrazine, a ketone with an aminooxy, or a ketone with a hydrazide.

Modification of a membrane active polyamine by attachment of an RGD masking agent yields a reversibly modified polyamine. In one embodiment, a membrane active polyamine modified by an RGD masking agent comprises the structure represented by:

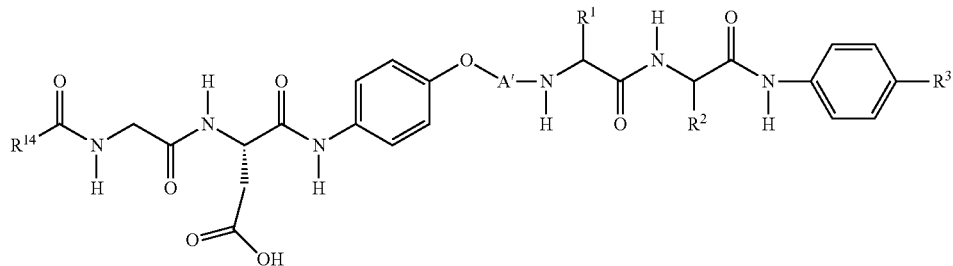

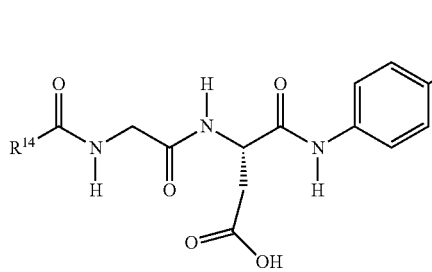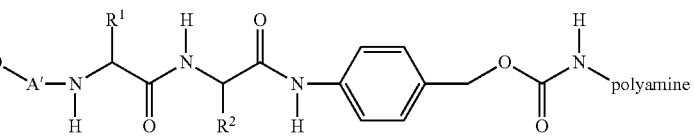

wherein $R^{14}$, $R^1$, $R^2$, and A' are as defined above. In one embodiment, the RGD is attached to the dipeptide after the dipeptide is linked to the amphipathic membrane active polyamine. In one embodiment, an aryl aldehyde-PEG2-dipeptide-amidobenzyl-carbonate is first reacted with a polyamine to form an aryl aldehyde-PEG2-dipeptide-amidobenzyl-carbamate-polyamine. This compound is then reacted with an RGD ligand-PEG1-diamine-HyNic to form: RGD ligand-PEG1-diamine-diaryl hydrazone-PEG2-dipeptide-amidobenzyl-carbomate-polyamine (See FIG. 13).

As used herein, the term peptide has the usual meaning in the art: a short chain of L α amino acid monomers linked by peptide (amide) bonds, the covalent chemical bonds formed when the carboxyl group of one amino acid reacts with the amino group of another.

As used herein, the phrase naturally occurring amino acid has the usual meaning in the art. As used herein, the phrase standard amino acid has the usual meaning in the art: a naturally occurring L α amino acid encoded directly by a triplet codon in the genetic code.

Non-limiting examples of membrane active polymers suitable for use with the invention have been previously described in US Patent Publications US20080152661, US20090023890, US20080287630, US20110207799, US20130121954, and US20130317079 (each of which is incorporated herein by reference). Suitable amphipathic membrane active polyamine can also be small peptides such as a melittin peptide.

Figure 3:
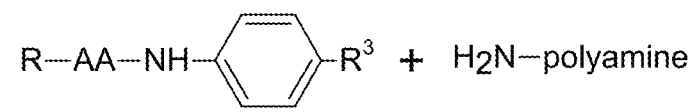
FIG. 3. Illustration showing reversible modification of a polyamine using a dipeptide masking agent: R comprises an RGD ligand or a PEG, AA is a dipeptide (either with or without protecting groups), $R^3$ is an amine-reactive carbonate, and polyamine is an amphipathic membrane active polyamine.
Figure 3:
Figure 3:
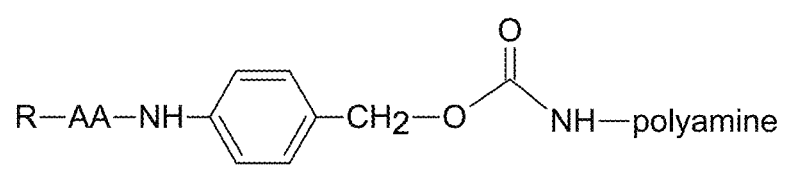

Polymer amines are reversibly modified using the peptidase cleavable linkers described herein. An amine is reversibly modified if cleavage of the modifying group results in regeneration of the amine. Reaction of the activated carbonate of the masking agent with a polymer amine connects an RGD ligand or steric stabilizer to the polymer via a peptidase cleavable dipeptide-amidobenzyl carbamate linkage as shown in FIG. 3.

Protecting groups may be used during synthesis and conjugation of RGD ligands and dipeptide masking agents. If present, protecting groups may be removed prior to or after modification of the amphipathic membrane active polyamine.

Figure 4:
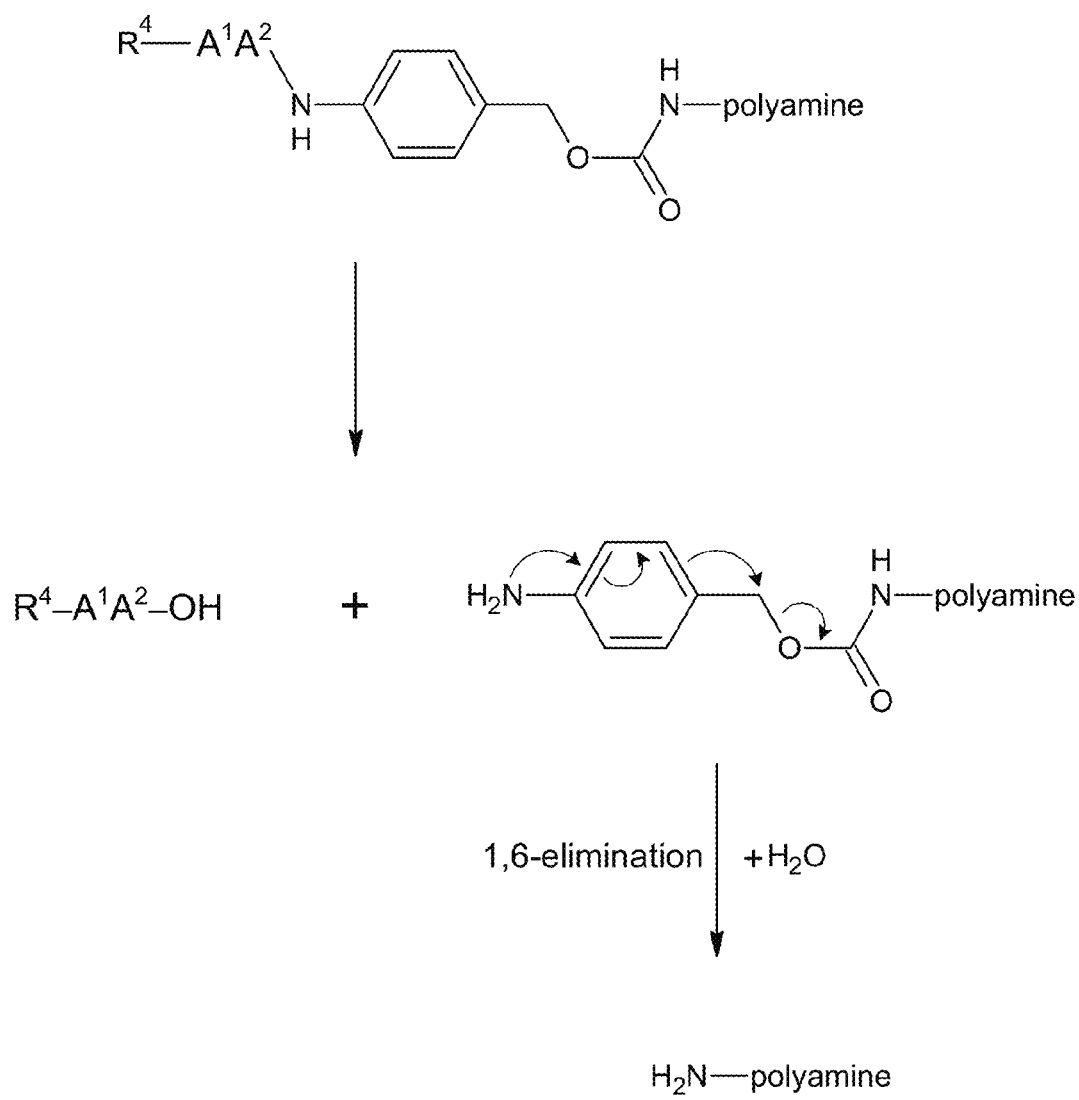
FIG. 4. Illustration showing the elimination reaction in which the amidobenzyl-carbamate undergoes a spontaneous rearrangement that results in regeneration of a polymer amine: AA ($A^1A^2$) is a dipeptide, and $R^4$ comprises an RGD ligand or a steric stabilizer.

Reversible modification of a sufficient percentage of the polymer amines with the dipeptide masking agents inhibits membrane activity of the membrane active polyamine. The dipeptide-amidobenzyl-carbamate linkage is susceptible to protease (or peptidase) cleavage. In presence of protease, the anilide bond is cleaved, resulting in an intermediate which immediately undergoes a 1,6 elimination reaction to release free polymer (FIG. 4). After the elimination reaction, the free polymer is unmodified and membrane activity is restored.

The membrane active polyamine can be conjugated to masking agents in the presence of an excess of masking agents. The excess masking agent may be removed from the conjugated delivery polymer prior to administration of the delivery polymer.

As used herein, a "steric stabilizer" is a non-ionic hydrophilic polymer (either natural, synthetic, or non-natural) that prevents or inhibits intramolecular or intermolecular interactions of a polymer to which it is attached relative to the polymer containing no steric stabilizer. A steric stabilizer hinders a polymer to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a polymer. A preferred steric stabilizer is a polyethylene glycol (PEG) or PEG derivative. As used herein, a preferred PEG can have about 1-500 ethylene glycol monomers, or 2-25. As used herein, a preferred PEG can also have a molecular weight average of about 85-20,000 Daltons (Da), about 85-1000 Da. As used herein, steric stabilizers prevent or inhibit intramolecular or intermolecular interactions of a polymer to which it is attached relative to the polymer containing no steric stabilizer in aqueous solution.

"Ligands" enhance the pharmacokinetic or biodistribution properties of a conjugate to which they are attached to improve cell- or tissue-specific distribution and cell-specific uptake of the conjugate. Ligands enhance the association of molecules with a target cell. Thus, ligands can enhance the pharmacokinetic or biodistribution properties of a conjugate to which they are attached to improve cellular distribution and cellular uptake of the conjugate. Binding of a ligand to a cell or cell receptor may initiate endocytosis. Ligands may be monovalent, divalent, trivalent, tetravalent, or have higher valency.

As used herein, membrane active polyamines are capable of disrupting plasma membranes or lysosomal/endocytic membranes. This membrane activity is an essential feature for cellular delivery of the RNAi trigger. Membrane activity, however, leads to toxicity when the polymer is administered in vivo. Polyamines also interact readily with many anionic components in vivo, leading to undesired bio-distribution. Therefore, reversible masking of membrane activity of the polyamine is necessary for in vivo use.

In a one embodiment, the membrane active polyamine comprises: an amphipathic polymer formed by random polymerization of amine-containing monomers and hydrophobic group-containing monomers. The amine-containing monomers contain pendant primary amine groups. The hydrophobic monomers contain pendent hydrophobic groups. The hydrophobic groups may be lower hydrophobic groups, having 1-6 carbon atoms, or higher hydrophobic groups, having more than 6 carbon atoms. Preferred hydrophobic group may be selected from the list comprising: propyl, butyl, isopropyl, and isobutyl. The ratio of amine groups to hydrophobic groups is selected to form a water soluble polymer with membrane disruptive activity, preferably ≥1 amine monomer per hydrophobic monomer. In one embodiment the polymer will have 50-80% amine monomers and more preferably 55-75% amine monomers. Hydrophobic groups may be selected from the group consisting of: alkyl group, alkenyl group, alkynyl group, aryl group, aralkyl group, aralkenyl group, and aralkynyl group, each of which may be linear, branched, or cyclic. Hydrophobic groups are preferably hydrocarbons, containing only carbon and hydrogen atoms. However, substitutions or heteroatoms which maintain hydrophobicity, and include, for example fluorine, may be permitted.

"Amphipathic", or amphiphilic, polymers are well known and recognized in the art and have both hydrophilic (polar, water-soluble) and hydrophobic (non-polar, lipophilic, water-insoluble) groups or parts.

"Hydrophilic groups" indicate in qualitative terms that the chemical moiety is water-preferring. Typically, such chemical groups are water soluble, and are hydrogen bond donors or acceptors with water. A hydrophilic group can be charged or uncharged. Charged groups can be positively charged (anionic) or negatively charged (cationic) or both (zwitterionic). Examples of hydrophilic groups include the following chemical moieties: carbohydrates, polyoxyethylene, certain peptides, oligonucleotides, amines, amides, alkoxy amides, carboxylic acids, sulfurs, and hydroxyls.

"Hydrophobic groups" indicate in qualitative terms that the chemical moiety is water-avoiding. Typically, such chemical groups are not water soluble, and tend not to form hydrogen bonds. Lipophilic groups dissolve in fats, oils, lipids, and non-polar solvents and have little to no capacity to form hydrogen bonds. Hydrocarbons containing two (2) or more carbon atoms, certain substituted hydrocarbons, cholesterol, and cholesterol derivatives are examples of hydrophobic groups and compounds.

Hydrophobic groups are preferably hydrocarbons, containing only carbon and hydrogen atoms. However, non-polar substitutions or non-polar heteroatoms which maintain hydrophobicity, and include, for example fluorine, may be permitted. The term includes aliphatic groups, aromatic groups, acyl groups, alkyl groups, alkenyl groups, alkynyl groups, aryl groups, aralkyl groups, aralkenyl groups, and aralkynyl groups, each of which may be linear, branched, or cyclic. The term hydrophobic group also includes: sterols, steroids, cholesterol, and steroid and cholesterol derivatives.

As used herein, with respect to amphipathic polymers, a part is defined as a molecule derived when one covalent bond is broken and replaced by hydrogen. For example, in butyl amine, a breakage between the carbon and nitrogen bonds, and replacement with hydrogens, results in ammonia (hydrophilic) and butane (hydrophobic). If 1,4-diaminobutane is cleaved at nitrogen-carbon bonds, and replaced with hydrogens, the resulting molecules are again ammonia (2×) and butane. However, 1,4,-diaminobutane is not considered amphipathic because formation of the hydrophobic part requires breakage of two bonds.

As used herein, a surface active polymer lowers the surface tension of water and/or the interfacial tension with other phases, and, accordingly, is positively adsorbed at the liquid/vapor interface. The property of surface activity is usually due to the fact that the molecules of the substance are amphipathic or amphiphilic.

As used herein, "membrane active" polymers are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polymer's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Polymers that preferentially cause disruption of endosomes or lysosomes over plasma membrane are considered endosomolytic. The effect of membrane active polymers on a cell membrane may be transient. Membrane active possess affinity for the membrane and cause a denaturation or deformation of bilayer structures. Membrane active polymers may be synthetic or non-natural amphipathic polymers.

As used herein, membrane active polymers are distinct from a class of polymers termed cell penetrating peptides or polymers represented by compounds such as the arginine-rich peptide derived from the HIV TAT protein, the antennapedia peptide, VP22 peptide, transportan, arginine-rich artificial peptides, small guanidinium-rich artificial polymers and the like. While cell penetrating compounds appear to transport some molecules across a membrane, from one side of a lipid bilayer to other side of the lipid bilayer, apparently without requiring endocytosis and without disturbing the integrity of the membrane, their mechanism is not understood.

Delivery of a RNAi trigger to a cell is mediated by the membrane active polymer disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Amphipathic membrane active polyamine copolymers of the invention are the product of copolymerization of two or more monomer species. In one embodiment, amphipathic membrane active heteropolymers of the invention have the general structure:

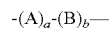

wherein, A contains a pendent primary amine functional group and B contains a pendant hydrophobic group. a and b are integers >0. The polymers may be random, block, or alternating. The incorporation of additional monomers is permissible.

As used herein, "endosomolytic polymers" are polymers that, in response to an endosomal-specific environmental factors, such as the presence of lytic enzymes, are able to cause disruption or lysis of an endosome or provide for release of a normally cell membrane impermeable compound, such as an RNAi trigger, from a cellular internal membrane-enclosed vesicle, such as an endosome or lysosome. Endosomolytic polymers undergo a shift in their physico-chemical properties in the endosome. This shift can be a change in the polymer's solubility or ability to interact with other compounds or membranes as a result in a shift in charge, hydrophobicity, or hydrophilicity. A reversibly masked membrane active polyamine of the invention are considered to be endosomolytic polymers.

As used herein, "melittin" is a small amphipathic membrane active peptide which naturally occurs in bee venom (US patent publication 20120165393). Melittin can be isolated from a biological source or it can be synthetic. A synthetic polymer is formulated or manufactured by a chemical process "by man" and is not created by a naturally occurring biological process. As used herein, melittin encompasses the naturally occurring bee venom peptides of the melittin family that can be found in, for example, venom of the species: *Apis mellifera, Apis cerana, Vespula maculifrons, Vespa magnifica, Vespa velutina nigrithorax, Polistes* sp. HQL-2001, *Apis florae, Apis dorsata, Apis cerana cerana, Polistes hebraeus*. As used herein, melittin also encompasses synthetic peptides having amino acid sequence identical to or similar to naturally occurring melittin peptides. Specifically, melittin amino acid sequence encompass those shown in Table 1. Synthetic melittin peptides can contain naturally occurring L form amino acids or the enantiomeric D form amino acids (inverso). However, a melittin peptide should either contain essentially all L form or all D form amino acids but may have amino acids of the opposite stereocenter appended at either the amino or carboxy termini. The melittin amino acid sequence can also be reversed (reverso). Reverso melittin can have L form amino acids or D form amino acids (retroinverso). Two melittin peptides can also be covalently linked to form a melittin dimer. Melittin can have modifying groups, other than masking agents, that enhance tissue targeting or facilitate in vivo circulation attached to either the amino terminal or carboxy terminal ends.

A linkage or "linker" is a connection between two atoms that links one chemical group or segment of interest to another chemical group or segment of interest via one or more covalent bonds. For example, a linkage can connect a masking agent, polynucleotide, or RNAi trigger to a polymer. A labile linkage contains a labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides. Spacer groups are well known in the art and the preceding list is not meant to limit the scope of the invention.

A "labile bond" is a covalent bond other than a covalent bond to a hydrogen atom that is capable of being selectively broken or cleaved under conditions that will not break or cleave other covalent bonds in the same molecule. More specifically, a labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life (t) of bond cleavage (the time required for half of the bonds to cleave). Thus, labile bonds encompass bonds that can be selectively cleaved more rapidly than other bonds a molecule.

As used herein, a "physiologically labile bond" is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. A cellular physiologically labile bond may also be cleaved in response to administration of a pharmaceutically acceptable exogenous agent.

The term "polynucleotide", or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap moiety at the 5'-end, the 3'-end, or both the 5' and 3' ends. The cap moiety can be, but is not limited to, an inverted deoxy abasic moiety, an inverted deoxy thymidine moiety, a thymidine moiety, or 3' glyceryl modification.

RNAi triggers inhibit gene expression through the biological process of RNA interference (RNAi). RNAi triggers comprise double stranded RNA or RNA-like structures typically containing 15-50 base pairs and preferably 18-25 base pairs and having a nucleobase sequence identical (perfectly complementary) or nearly identical (substantially complementary) to a coding sequence in an expressed target gene within the cell. RNAi triggers include, but are not limited to: short interfering RNAs (siRNAs), double-strand RNAs (dsRNA), micro RNAs (miRNAs), short hairpin RNAs (shRNA), meroduplexes, and dicer substrates (U.S. Pat. Nos. 8,084,599 8,349,809 and 8,513,207).

The RNAi trigger comprises at least two sequences that are partially, substantially, or fully complementary to each other. In one embodiment, the two RNAi trigger sequences comprise a sense strand comprising a first sequence and an antisense strand comprising a second sequence. In another embodiment, the two RNAi trigger sequences comprise two sense strands which together comprise a first sequence and an antisense strand comprising a second sequence, wherein the sense strands and the antisense strand together form a meroduplex (Tables 2 and 4). The sense strand may be connected to the antisense strand via a linker molecule, such as a polynucleotide linker or a non-nucleotide linker.

The antisense strand comprises a nucleotide sequence which is complementary to a part of an mRNA encoding by a target gene, and the region of complementarity is most preferably less than 30 nucleotides in length. The RNAi trigger sense strands comprise sequences which have an identity of at least 90% to at least a portion of an AAT mRNA. The RNAi trigger, upon delivery to a cell expressing the target gene, inhibits the expression of said target gene in vitro or in vivo.

RNAi trigger molecules may be comprised of naturally occurring nucleotides or may be comprised of at least one modified nucleotide or nucleotide mimic. The RNAi trigger sense and antisense strands of the invention may be synthesized and/or modified by methods well established in the art. RNAi trigger molecules nucleosides, or nucleotide bases, may be linked by phosphate-containing (natural) or non-phosphate-containing (non-natural) covalent internucleoside linkages, i.e. the RNAi trigger molecules may have natural or non-natural oligonucleotide backbones. In another embodiment, at the RNAi trigger contains at non-standard (non-phosphate) linkage between to nucleotide bases.

Modified nucleotides include, but are not limited to: 2' modifications, 2'-O-methyl nucleotide, 2'-deoxy-2'-fluoro nucleotide, 2'-deoxy nucleotide, 2'-amino nucleotide, 2'-alkyl nucleotide, terminal 3' to 3' linkages, inverted deoxythymidine, a nucleotide comprising a 5'-phosphorothioate group, thiophosphate linkages, phosphorodithioate group, non-natural base comprising nucleotide, locked nucleotides, bridged nucleotides, peptide nucleic acids, unlocked nucleotides (represented herein as $N_{UNA}$), morpholino nucleotides, and abasic nucleotide. It is not necessary for all positions in a given compound to be uniformly modified. Conversely, more than one modifications may be incorporated in a single RNAi trigger compound or even in a single nucleotide thereof. Ribose 2' modification may be combined with modified nucleoside linkages.

RNAi trigger molecules may also comprise overhangs, i.e. typically unpaired, overhanging nucleotides which are not directly involved in the double helical structure normally formed by the core sequences of the herein defined pair of sense strand and antisense strand.

RNAi triggers may contain 3' and/or 5' overhangs of 1-5 bases independently on each of the sense strands and antisense strands. In one embodiment, both the sense strand and the antisense strand contain 3' and 5' overhangs. In one embodiment, one or more of the 3' overhang nucleotides of one strand base pairs with one or more 5' overhang nucleotides of the other strand. In another embodiment, the one or more of the 3' overhang nucleotides of one strand base do not pair with the one or more 5' overhang nucleotides of the other strand. The sense and antisense strands of an RNAi trigger may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In another embodiment, one or more of the nucleotides in the overhang contains a thiophosphate, phosphorothioate, deoxynucleotide inverted (3' to 3' linked) nucleotide or is a modified ribonucleotide or deoxynucleotide.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

An RNAi trigger modulates expression of RNA encoded by a gene. Because multiple genes can share some degree of sequence homology with each other, an RNAi trigger can be designed to target a class of genes with sufficient sequence homology. Thus, an RNAi trigger can contain a sequence that has complementarity to sequences that are shared amongst different gene targets or are unique for a specific gene target. Therefore, the RNAi trigger can be designed to target conserved regions of an RNA sequence having homology between several genes thereby targeting several genes in a gene family (e.g., different gene isoforms, splice variants, mutant genes, etc.). In another embodiment, the RNAi trigger can be designed to target a sequence that is unique to a specific RNA sequence of a single gene.

The term "complementarity" refers to the ability of a polynucleotide to form hydrogen bond(s) with another polynucleotide sequence by either traditional Watson-Crick or other non-traditional types. In reference to the polynucleotide molecules of the present invention, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene or the level of polypeptide, protein or protein subunit translated from the RNA, is reduced below that observed in the absence of the RNAi trigger-conjugates of the invention. Inhibition, down-regulation, or knockdown of gene expression, with a RNAi trigger delivered by the compositions of the invention, is preferably below that level observed in the presence of a control inactive nucleic acid, a nucleic acid with scrambled sequence or with inactivating mismatches, or in absence of conjugation of the RNAi trigger to the masked polymer.

Linkage of an RNAi Trigger to Delivery Polymer

In one embodiment, the RNAi trigger is linked to the delivery polymer via a physiologically labile bond or linker. The physiologically labile linker is selected such that it undergoes a chemical transformation (e.g., cleavage) when present in certain physiological conditions, (e.g., disulfide bond cleaved in the reducing environment of the cell cytoplasm). Release of the trigger from the polymer, by cleavage of the physiologically labile linkage, facilitates interaction of the trigger with the appropriate cellular components for activity.

The RNAi trigger-polymer conjugate is formed by covalently linking the trigger to the polymer. The polymer is polymerized or modified such that it contains a reactive group A. The RNAi trigger is also polymerized or modified such that it contains a reactive group B. Reactive groups A and B are chosen such that they can be linked via a reversible covalent linkage using methods known in the art.

Conjugation of the RNAi trigger to the polymer can be performed in the presence of an excess of polymer. Because the RNAi trigger and the polymer may be of opposite charge during conjugation, the presence of excess polymer can reduce or eliminate aggregation of the conjugate. Alternatively, an excess of a carrier polymer, such as a polycation, can be used. The excess polymer can be removed from the conjugated polymer prior to administration of the conjugate to the animal or cell culture. Alternatively, the excess polymer can be co-administered with the conjugate to the animal or cell culture.

In Vivo Administration

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions of the invention. The compounds of the present invention can be administered via any suitable route, most preferably parenterally, in a preparation appropriately tailored to that route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals and more particularly in humans.

These carrier may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic Effect

RNAi triggers may be delivered for research purposes or to produce a change in a cell that is therapeutic. In vivo delivery of RNAi triggers is useful for research reagents and for a variety of therapeutic, diagnostic, target validation, genomic discovery, genetic engineering, and pharmacogenomic applications. We have disclosed RNAi trigger delivery resulting in inhibition of endogenous gene expression in hepatocytes. Levels of a reporter (marker) gene expression measured following delivery of a RNAi trigger indicate a reasonable expectation of similar levels of gene expression following delivery of other RNAi triggers. Levels of treatment considered beneficial by a person having ordinary skill in the art differ from disease to disease. For example, Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. Similarly, inhibition of a gene need not be 100% to provide a therapeutic benefit. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes serve as useful paradigms for expression of intracellular proteins in general.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

As used herein, in vivo means that which takes place inside an organism and more specifically to a process performed in or on the living tissue of a whole, living multicellular organism (animal), such as a mammal, as opposed to a partial or dead one.

As used herein, "pharmaceutical composition" includes the conjugates of the invention, a pharmaceutical carrier or diluent and any other media or agent necessary for formulation.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

EXAMPLES

Example 1

Synthesis of PEG Protease (Peptidase) Cleavable Masking Agents

All reactions, except coupling of amino acids in aqueous NaHCO$_3$ and silyl-group deprotection, were carried out in anhydrous conditions using fresh anhydrous solvents. Column purification was done on a silica gel using specified eluents. Mass-spectra (MS) were taken using electrospray ionization.

Figure 5:
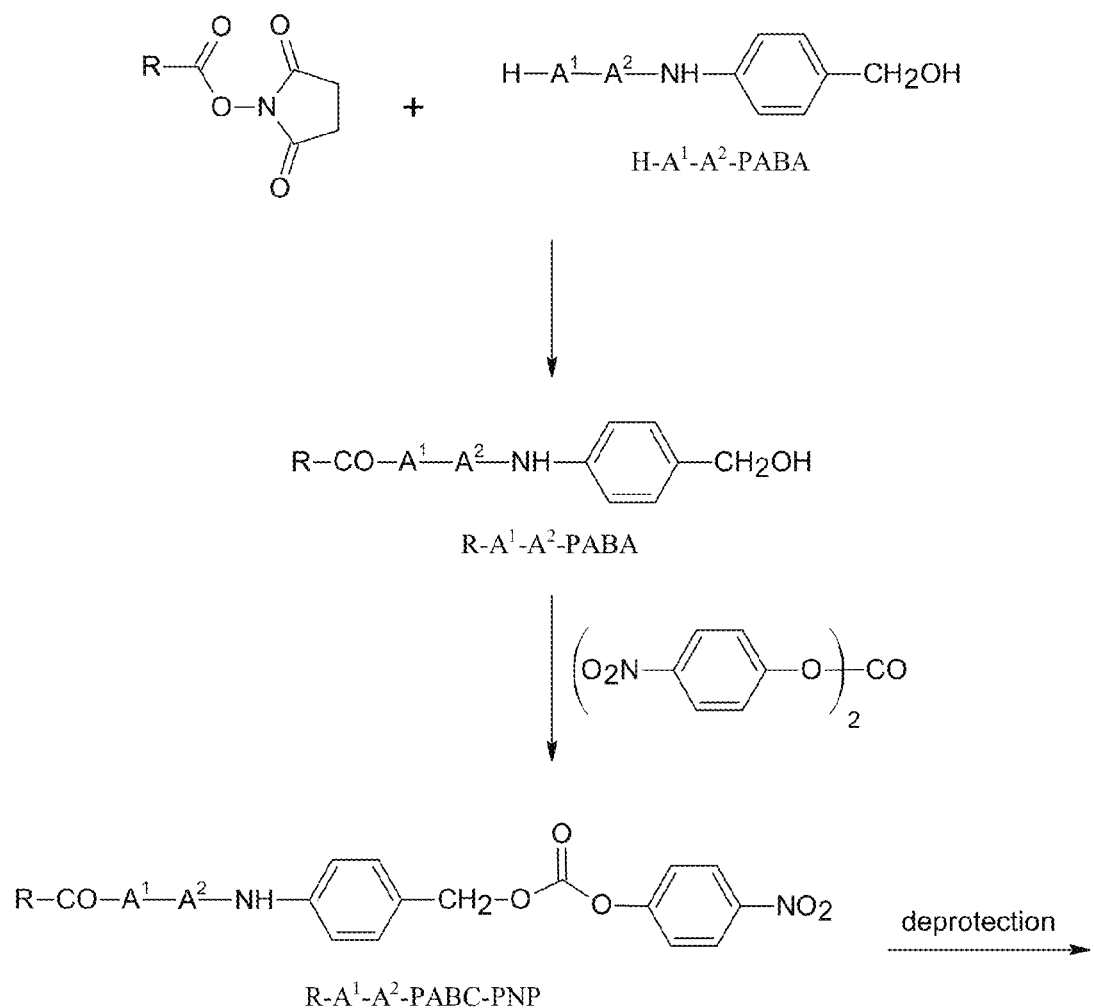
FIG. 5. Illustration showing synthesis of PEG dipeptide masking agents: R comprises a PEG, and $A^1$ and $A^2$ are amino acids (either protected or unprotected).
Figure 6:
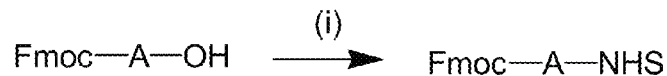
FIG. 6. Illustrations showing formation of (A) NHS esters of dipeptides, (B) amino acids H-Asn(DMCP)-OH and H-Lys(MMT)-OH from Fmoc-protected derivatives, and (C) Fmoc-$A_1A_2$-OH: A, $A^1$, and $A^2$ are amino acids.
Figure 6:
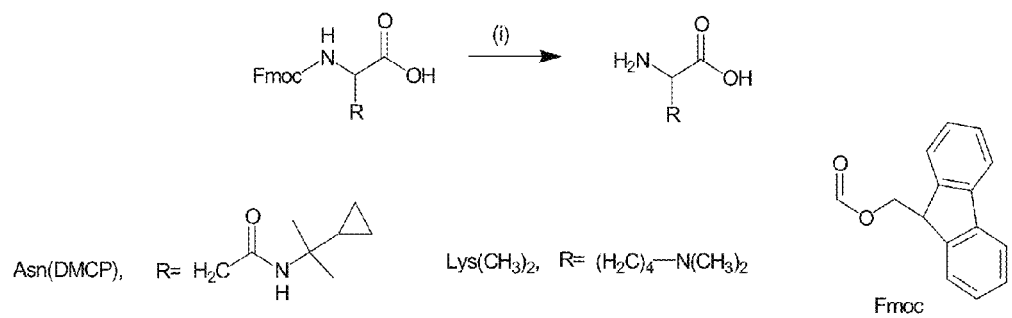
Figure 6:
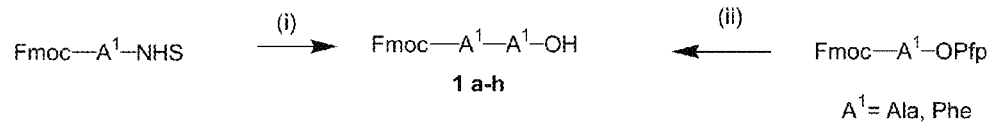

In preparation of active p-nitrophenyl-p-acylamidobenzyl carbonate derivatives of PEG PEG-AA-PABC-PNP) we utilized NHS ester of PEG or to acylate amino terminus of dipeptido-p-acylaminobenzy alcohol precursor. In the following steps benzylic hydroxyl group was converted into p-nitrophenyl carbonate followed by removal of protective groups from amino acids. In some applications, when paranitrophenol (PNP)-carbonates were used for modification of certain polymers, protective groups were removed prior to polymer modification (see FIG. 5).

The synthesis starts from preparation of H-A$^1$A$^2$-PABA (Table 2) derivatives. These adducts were obtained utilizing synthetic scheme described by Dubowchik at al. (2002) with some modifications. Fmoc-protected amino acids, Fmoc-A$^1$-OH, were activated by conversion into N-hydroxycuccinimide esters, Fmoc-A$^1$-NHS, in reaction with dicyclohexylcarbodiimide (DCC) and N-hydroxycuccinimide (NHS). These reactive NHS-esters were coupled with protected amino acids A$^2$ in presence of aqueous NaHCO$_3$ added to keep amino group reactive. For preparation of 1e and 1f (Table 2), instead of NHS esters, commercially available pentafluorophenyl esters (OPfp) for were used for coupling.

Synthesis of Fmoc Dipeptides 1a-h.

a) NHS Esters of AA were Prepared from Respective Amino Acids with NHS and DCC and Used without Additional Purification (FIG. 5A).

For Fmoc-Ala-NHS, DCC (286 mg, 1.38 mmol) was added to an ice cold solution of Fmoc-Ala-OH (412 mg, 1.32 mmol) and NHS (160 mg, 1.38 mmol) in DCM (13 ml), stirred for 30 min, and then at 20° C. for 16 h (hour). The solid dicyclohexylurea (DCU) was filtered off and the solvent was removed in vacuo.

For Fmoc-Asn(DMCP)-NHS, DCC (148 mg, 0.72 mmol) was added to an ice cold solution of Fmoc-Asn(DMCP)-OH (298 mg, 0.68 mmol) and NHS (83 mg, 0.72 mmol) in DCM (13 ml), stirred for 30 min, and then at 20° C. for 16 h. The solid DCU was filtered off and the solvent was removed in vacuo.

For Fmoc-Gly-NHS, Fmoc-Gly-OH (891 mg, 3 mmol) and NHS (380 mg, 3.3 mmol) were stirred in THF (10 ml) at 0° C. for 5 min and treated with a DCC solution (650 mg, 3.15 mmol) in THF (5 ml). The cooling bath was removed in 30 min and the reaction mixture was stirred at 20° C. for 10 h. The solid DCU was filtered off, washed with THF and the solvent was removed on the rotovap. The product was weighed and dissolved in DME to make a 0.2 mM solution.

For Fmoc-Glu(O-2PhiPr)-NHS, DCC (217 mg, 1.05 mmol) was added to an ice cold solution of Fmoc-Glu(O-2PhiPr)-OH (487 mg, 1 mmol) and NHS (127 mg, 1.1 mmol) in THF (5 ml), stirred for 15 min and then at 20° C. for 10 h. The workup was done as described for Fmoc-Gly-NHS.

For Fmoc-Phe-NHS, DCC (1.181 g, 5.72 mmol) was added to an ice cold solution of Fmoc-Phe-OH (2.11 g, 5.45 mmol) and NHS (664 mg, 5.77 mmol) in DCM (50 ml), stirred for 30 min, and then at 20° C. for 10 h. The solid DCU was filtered off and the solvent was removed in vacuo.

For Fmoc-Val-NHS, DCC (227 mg, 1.1 mmol) was added to an ice cold solution of Fmoc-Val-OH (339 mg, 1 mmol) and NHS (127 mg, 1.1 mmol) in DCM (13 ml), stirred for 30 min, and then at 20° C. for 16 h. The solid DCU was filtered off and the solvent was removed in vacuo.

b) Amino Acids H-Asn(DMCP)-OH and H-Lys(MMT)-OH were Prepared from Available Fmoc-Protected Derivatives (See FIG. 5B).

H-Asn(DMCP)-OH. Fmoc-Asn(DMCP)-OH (576 mg, 1.32 mmol) was stirred in DMF (9 ml) with Et$_3$N (3.7 ml, 26.4 mmol) for 15 h. All volatiles were removed on a rotovap at 40° C./oil pump vacuum. The residue was triturated with ether (30 ml) three times and dried in vacuo. Yield 271 mg (96%). MS: 643.6 [3M+1]$^+$; 451.3 [2M+Na]$^+$; 429.5 [2M+1]$^+$; 236.7 [M+Na]$^+$; 215.3 [M+1]$^+$; 132.8 [M−DMCP+1]$^+$.

H-Lys(MMT)-OH. Fmoc-Lys(MMT)-OH (4.902 g, 7.65 mmol) was stirred in DMF (100 ml) with Et$_3$N (32 ml, 30 eq. 229.4 mmol) for 10 h. All volatiles were removed on a rotovap at 40° C./oil pump vacuum. The residue was triturated with ether two times and dried in vacuo. Yield 3.1 g (97%). MS (neg. mode): 455, 453.3 [M+Cl]$^−$; 417.8 [M−1]$^−$.

c) Synthesis of Fmoc-A$_1$A$_2$-OH. (FIG. 5C.) For Fmoc-GlyGly-OH 1a, Glycine (75 mg, 1 mmol) and NaHCO$_3$ (100 mg, 1.2 mmol) were dissolved in H$_2$O (10 ml) and dimethoxyethane (DME) (5 ml). Fmoc-Gly-NHS solution in DME (5 ml, 1 mmol) was added. THF (2.5 ml) was added, the mixture was sonicated to make it homogeneous and stirred for 20 h. All volatiles were removed on a rotovap, the residue was treated with EtOAc and 5% KHCO$_3$ solution in H$_2$O. Product was extracted four times with EtOAc, washed with brine at pH=3, dried (Na$_2$SO$_4$), concentrated and dried in vacuo. Yield 321 mg (90%). MS: 775.0 [2M+2Na]$^+$; 377.4 [M+Na]$^+$; 355.1 [M+1]$^+$.

For Fmoc-Glu(O-2PhiPr)Gly-OH 1b, Glycine (75 mg, 1 mmol) and NaHCO$_3$ (84 mg, 1 mmol) were dissolved in a mixture of H$_2$O (2 ml), THF (4 ml) and DME (5 ml). Fmoc-Glu(O-2PhiPr)-NHS solution in DME (5 ml, 1 mmol) was added and stirred for 10 h. All volatiles was removed on a rotovap, 20 ml of 0.1M MES buffer (pH=5) was added followed by EtOAc (25 ml). The reaction mixture was stirred on ice and acidified to pH=5 with 5% solution of KHSO$_4$. Product was extracted four times with EtOAc, rinsed with brine at pH=5, dried (Na$_2$SO$_4$), concentrated and dried in vacuo. Yield 528 mg (96%). MS: 567 [M+Na]$^+$; 562 [M+NH$_4$]$^+$; 545.0 [M+1]$^+$; 427.1 [M−2PhiPr]$^+$.

For Fmoc-Asn(DMCP)Gly-OH c1 was prepared from Fmoc-Asn(DMCP)-NHS and H-Gly-OH as described above for 1b. Yield 96%. MS: 987.4 [2M+1]$^+$; 516.3 [M+Na]$^+$; 494.4 [M+1]$^+$; 412.2 [M−DMCP+1]$^+$.

For Fmoc-PheLys(MMT)-OH 1d was prepared from Fmoc-Phe-NHS and H-Lys(MMT)-OH as described above for 1b. Yield 94%. MS: 788.5 [M+1]$^+$, 273.1 [M−MMT+1]$^+$.

For Fmoc-PheCit-OH 1e:
i) To Fmoc-Phe-NHS (4.96 g, 10.26 mmol) in DME (40 ml) was added to a solution containing L-citrulline (1.80 g, 10.26 mmol) and NaHCO$_3$ (0.86 g, 10.26 mmol) in a mixture of H$_2$O (40 ml) and THF (20 ml). The reaction was stirred for 15 h. Residual DCC from activation was filtered and the organic solvent was removed on a rotovap. To the residue was added H$_2$O (100 ml) and iPrOH (10 ml). The suspension was acidified to pH=3 with 5% KHSO$_4$, the product was extracted with an EtOAc:iPrOH=9:1 solution (3×, 500 ml), washed with a mixture of brine:iPrOH=9:1 (2×, 50 ml), dried (Na$_2$SO$_4$), filtered and concentrated, and dried with oil pump. Trituration with ether afforded the pure product 1e. Yield 3.84 g (68%). MS: 545.6 [M+Na]$^+$; 528.5 [M−H$_2$O]$^+$; 306.3 [M−Fmoc+H$_2$O]$^+$.
ii) A solution of Fmoc-Phe-OPfp (553 mg, 1 mmol) in THF (5 ml) was added to a solution of H-Cit-OH (184 mg, 1.05 mmol) and NaHCO$_3$ (88.2 mg, 1.05 mmol) in H$_2$O (2.6 ml). THF (2 ml) was added to make the solution homogeneous and stirred for 10 h. THF was removed on a rotovap, the residue was diluted with H$_2$O (10 ml) and iPrOH (1 ml) and acidified to pH=1 with 3% HCl. The product was extracted five times with an EtOAc:iPrOH=9:1 solution, rinsed with a mixture of brine:iPrOH=9:1, dried (Na$_2$SO$_4$) and concentrated in vacuo. Trituration with ether afforded 313 mg of pure product 1e (57%).

Fmoc-AlaCit-OH 1f was prepared from Fmoc-Ala-NHS and H-Cit-OH as described above for 1e-(a). Yield 77%. MS: 959.8 [2M+Na]$^+$; 938.1 [2M+1]$^+$; 491.4 [M+Na]$^+$; 469.9 [M+1]$^+$.

Crude Fmoc-ValCit-OH 1g was prepared from Fmoc-Val-NHS and H-Cit-OH as described above for 1b. The final purification was done by trituration with ether. Total yield 76%. MS: 1060.3 [2M+3Na]$^+$; 1015.7 [2M+Na]$^+$; 519.7 [M+Na]$^+$; 497.9 [M+1]$^+$.

Fmoc-Ala-Asn(DMCP)-OH 1h was prepared from Fmoc-Ala-NHS and H-Asn(DMCP)-OH as described above for 1b. Yield 95%. MS: 530.2 [M+Na]$^+$; 508.2 [M+1]$^+$; 426.0 [M−DMCP+1]$^+$.

Coupling with p-Aminobenzyl Alcohol, Preparation of Fmoc-AA-PABA and Fmoc-A-PABA 2a-m.

Products 1a-h were coupled with p-aminobenzyl alcohol (PABA) in presence of 2-ethoxy-1-ethoxycarbonyl-1,2-dihydroquinoline (EEDQ) to form 2a-h. Four representatives 3 j-l with only one amino acid attached to PABA moiety were also prepared (FIG. 7A).

For Fmoc-GlyGly-PABA 2a, a solution of 1a (318 mg, 0.9 mmol) and PABA (220 mg, 1.8 mmol) in DCM (17 ml) and MeOH (6 ml) were stirred with EEDQ (444 mg, 1.8 mmol) for 10 h. All volatiles were removed on a rotovap, the residue was triturated with Et$_2$O and the product was filtered out and dried in vacuo. Yield 348 mg (84%).

For Fmoc-Glu(O-2PhiPr)Gly-PABA 2b, a solution of 1b (524 mg, 0.96 mmol) and PABA (142 mg, 1.55 mmol) in DCM (10 ml) was stirred with EEDQ (357 mg, 1.44 mmol) for 10 h. The workup was done as described above for 2a. Yield 462 mg (74%).

Fmoc-Asn(DMCP)Gly-PABA 2c, was prepared as described above for 2a. Yield 64%. MS: 621.5 [M+22]$^+$; 599.3 [M+1]$^+$.

Fmoc-PheLys(MMT)-PABA 2d, was prepared as described above for 2b. Yield 70%.

For Fmoc-PheCit-PABA 2e, a solution of 1e (5.98 g, 10.97 mmol) and PABA (2.70 g, 21.95 mmol) in DCM (150 ml) and MeOH (50 ml) was treated with EEDQ (5.43 g, 21.95 mmol) and stirred for 15 h. The workup was done as described above for 2a. Yield 6.14 g (86%). MS: 650.7 [M+1]$^+$; 527.3 [M−PABA+1]$^+$.

For Fmoc-AlaCit-PABA 2f, a solution of 1f (2.89 g, 6.17 mmol) and PABA (1.52 g, 12.34 mmol) in DCM (45 ml) and MeOH (15 ml) was treated with EEDQ (3.05 g, 12.34 mmol) and stirred for 15 h. The workup was done as described above for 2a. Yield 4.56 g (74%). MS (ES, neg. mode): 307.4 [M−263.6−1]$^−$; 349.9 [M−Fmoc-1]$^−$; 610, 608.4 [M+HCl−1]$^−$.

Fmoc-ValCit-PABA 2g was prepared as described above for 2b. (98%).

Fmoc-AlaAsn(DMCP)-PABA 2h was prepared as described above for 2a. Yield 59%. MS: 613.2 [M+1]$^+$; 531.4 [M−DMCP+1]$^+$; 408.2 [M−205+1]$^+$.

For Fmoc-Lys(CH$_3$)$_2$-PABA 2i, Fmoc-Lys(CH$_3$)$_2$—OH.HCl salt (433 mg, 1 mmol) and PABA (246 mg, 2 mmol) were dissolved in DCM (10 ml) and MeOH (1.5 ml), cooled to 5° C. and EEDQ (495 mg, 2 mmol) was added. The cooling bath was removed and the mixture was stirred for 10 h at RT (room temperature). All volatiles were removed on a rotovap, the residue was triturated with Et$_2$O, and the crude product was filtered off. It was redissolved in a mixture of DCM (2 ml) and MeOH (1 ml) and precipitated again by adding dropwise into Et$_2$O (40 ml). Product was filtered and dried in vacuo. Yield 448 mg (83%).

For Fmoc-Leu-PABA 2j, a solution of Fmoc-Leu-OH (353 mg, 1 mmol), EEDQ (495 mg, 2 mmol) and PABA (222 mg, 1.8 mmol) in DCM (10 ml) was stirred for 10 h. All volatiles were removed on a rotovap, the residue was dissolved in Et$_2$O (40 ml), chilled on dry ice for 2 h and the solid was separated by centrifugation. The obtained crude material was purified on a column, eluent gradient of MeOH (1-2%) in CHCl$_3$. Yield 444 mg (97%). MS: 459.4 [M+1]$^+$.

Fmoc-Asn(DMCP)-PABA 2k was prepared as described for 2j. In workup instead of column purification after removing of DCM the residue was triturated with Et$_2$O, chilled to 0° C. and the crude product was filtered off. This treatment was repeated one more time followed by drying in vacuo. Yield 77%. MS: 542.5 [M+1]$^+$.

For Fmoc-Cit-PABA 2l, a solution of Fmoc-Cit-OH (345.7 mg, 0.87 mmol) and PABA (214 mg, 1.74 mmol) in DCM (10 ml) and MeOH (4 ml) was treated with EEDQ (430 mg, 1.74 mmol) and stirred for 15 h. The solid product was triturated three times with ether, and the product was filtered and dried. Yield 288 mg (67%). MS: 502.3 [M+1]$^+$; 485.5 [M−H$_2$O+1]$^+$; 263 [M−Fmoc-H$_2$O+1]$^+$; 179.0 [M−306+1]$^+$; 120.2 [M−365.3+1]$^+$.

Product 2m was prepared using different scheme: coupling of H-Lys(CH$_3$)$_2$-PABA derivative 3 with Fmoc-Phe-NHS (FIG. 7B).

For Fmoc-PheLys(CH$_3$)-PABA 2m, Fmoc-Lys(CH$_3$)$_2$-PABA (2i) (448 mg, 0.83 mmol) was Fmoc deprotected by stirring with Et$_3$N (3.5 ml) in DMF (11 ml) for 10 h. All volatiles were removed on a rotovap at 40° C./oil pump vacuum to obtain the crude product 3i. This product was dissolved in DMF (7 ml), Fmoc-Phe-NHS (482 mg, 0.996 mmol) was added followed by DIEA (0.42 ml, 2.2 mmol) and the mixture was stirred for 10 h. The solvent with DIEA was removed on a rotovap at 40° C./oil pump vacuum to obtain crude 2m which was used without additional purification. MS: 549.4 [M+1]$^+$.

Figure 7:
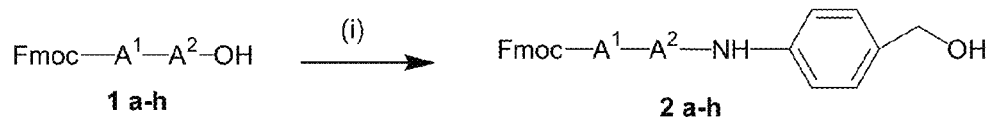
FIG. 7. Illustrations showing (A) formation of Fmoc-AA-PABA and Fmoc-A-PABA and (B) coupling of H-Lys(CH$_3$)$_2$-PABA with Fmoc-Phe-NHS.
Figure 7:
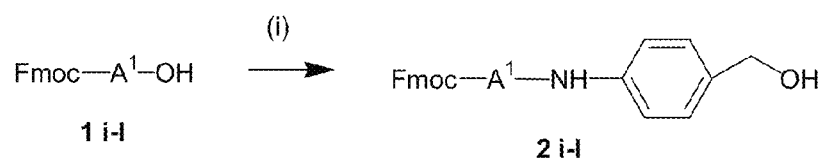
Figure 7:
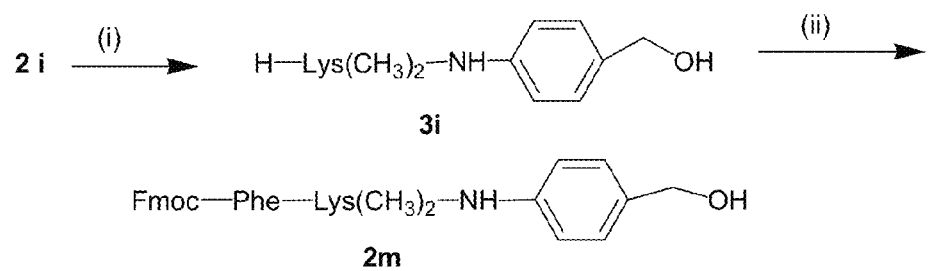
Figure 8:
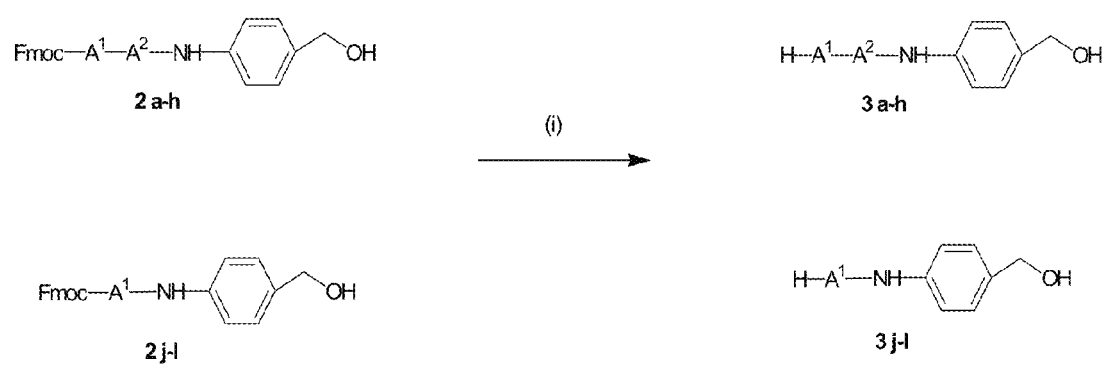
FIG. 8. Illustration showing formation of H-$A^1A^2$-PABA and H-$A^1$-PABA.

Preparation of H-AA-PABA 3a-h, m and H-A-PABA 3j-l (FIG. 7).

Fmoc-derivatives 2a-h, j-l were treated with Et$_3$N in DMF as described above for 3i followed by concentration and drying in vacuo. The crude products were dissolved in DMF to make 0.1 M solution and used without additional purification.

TABLE 2

Intermediates of H-A$^1$A$^2$-PABA (1-3)

| | A$^1$ | A$^2$ |
|---|---|---|
| 1, 2, 3a | Gly | Gly |
| 1, 2, 3b | Glu(2PhiPr) | Gly |
| 1, 2, 3c | Asn(DMCP) | Gly |
| 1, 2, 3d | Phe | Lys(MMT) |
| 1, 2, 3e | Phe | Cit |
| 1, 2, 3f | Ala | Cit |
| 1, 2, 3g | Val | Cit |
| 1, 2, 3h | Ala | Asn(DMCP) |
| 1, 2, 3i | Lys(CH$_3$)$_2$ | |
| 1, 2, 3j | Leu | — |
| 1, 2, 3k | Asn(DMCP) | — |
| 1, 2, 3l | Cit | — |
| 2, 3m | Phe | Lys(CH$_3$)$_2$ |

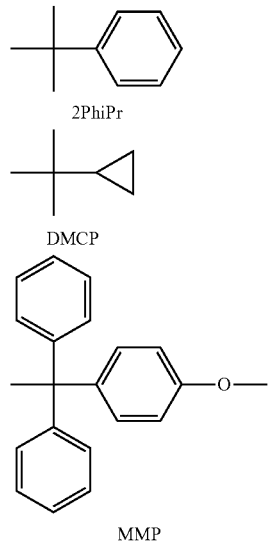

2PhiPr

DMCP

MMP

Preparation of Protease Cleavable PEG-Masking Reagents.

The amino group of any of H-AA-PABA 3b, e, g, h, j, k-m was acylated with an NHS ester of PEG-acid (DIEA, DMF, 5-10 h) to yield 22a-k. The hydroxyl group in product 22a-k was then converted into p-nitrophenyl carbonate ((PNP)$_2$CO, dioxane or THF, 40-60° C., 10 h) to yield 23a-k. For 23a, d, g, protective groups from Asn and Glu were removed by treatment with aqueous TFA (TFA/H$_2$O=3:1, 5° C., 2-3 h) to obtain desired products 24a-c.

Figure 9:
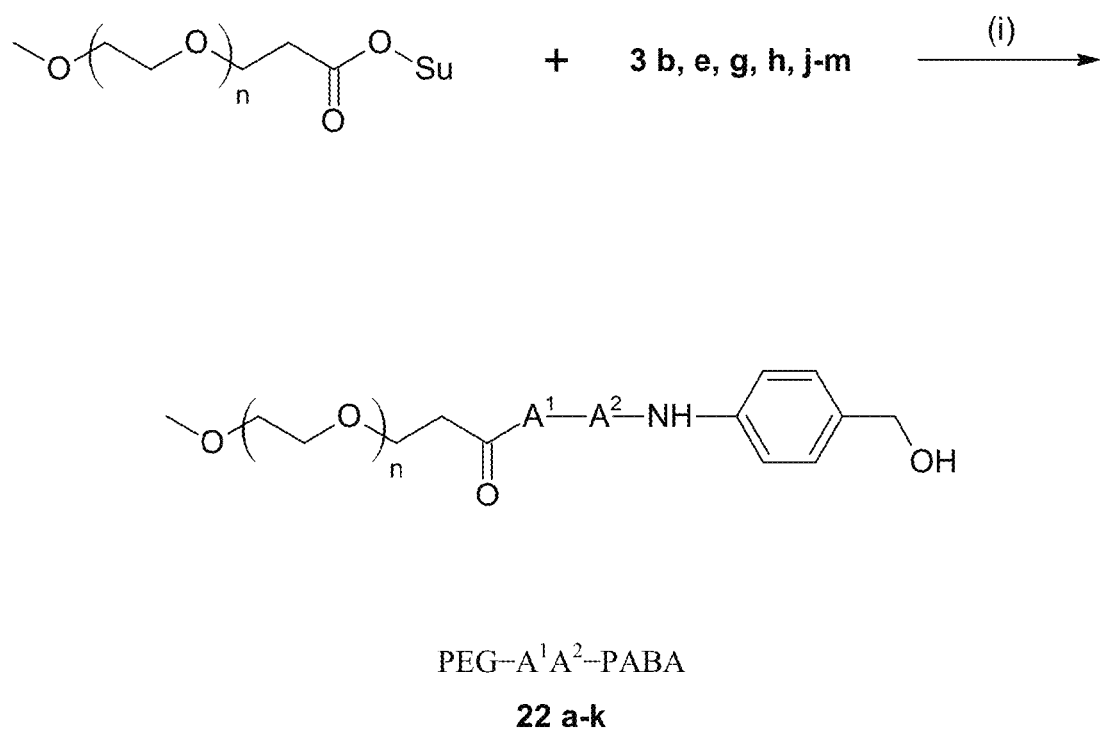
FIG. 9. Illustration showing formation of PEG$_n$-$A^1A^2$-PABA.

Preparation of PEG$_n$-AA-PABA 22a-k (FIG. 9).

Product 22a (n=1, AA=GluGly). A 0.1M solution of 3b in DMF (3.5 ml, 0.35 mmol) was stirred for 10 h with PEG$_{11}$-NHS ester (240 mg, 0.35 mmol) and DIEA (0.061 ml, 0.35 mmol). All volatiles were removed on a rotovap at 40° C./oil pump and the product was purified on a column, eluent: CHCl$_3$:MeOH:AcOH=38:2:1. Yield 274 mg (78%) MS: 1015.6 [M+NH$_4$]$^+$, 998.7 [M+1]$^+$.

Product 22b (n=11, AA=PheCit). To a solution of 3e (0.88 mmol) and DIEA (167 µl, 0.96 mmol) in DMF (3 ml) was added a solution of PEG$_{11}$-NHS ester (0.80 mmol) in DMF (3 ml). The mixture was stirred for 16 h, filtered and all volatiles were removed on a rotovap at 40° C./oil pump vacuum. The crude was precipitated into Et$_2$O (45 ml) from CHCl$_3$:MeOH (5 ml) and purified on a column, eluent a gradient of MeOH (10-16%) in CHCl$_3$. Yield 420 mg (53%). MS: 1015.9 [M+H$_2$O]$^+$; 998.8 [M+1]$^+$; 981.1 [M−H$_2$O]$^+$.

Product 22c (n=11, AA=ValCit). Product 22f was prepared from crude 3g (obtained from 300 mg, 0.5 mmol of 2g), PEG$_{11}$-NHS ester (298 mg, 0.435 mmol) and DIEA (0.09 ml, 0.522 mmol) as described for 22a. Following concentration on a rotovap at 40° C./oil pump the product was suspended in a MeOH:DCM=1:1 mixture (6 ml), sonicated, filtered and precipitated into Et$_2$O (50 ml). The solid was separated and the procedure repeated again. The residual solvents were removed in vacuo. Yield 283 mg (60%). MS: 951.5 [M+1]$^+$.

Product 22d (n=11, AA=AlaAsn(DMCP)). To a solution of 3h (0.56 mmol) and DIEA (116 µl, 0.67 mmol) in DMF (3 ml) was added a solution of PEG$_{11}$-NHS ester (0.56 mmol) in DMF (3 ml). The mixture was stirred for 16 h, filtered and all volatiles were removed on a rotovap at 40° C./oil pump vacuum. The residue was dissolved in a CHCl$_3$:MeOH=1:1 mixture (5 ml) and precipitated into chilled (0° C.) Et$_2$O (45 ml). The solid was purified on a column, eluent gradient of MeOH (3-14%) in DCM. Yield 261 mg (49%). MS: 983.7 [M+Na]$^+$; 979.1 [M+NH$_4$]$^+$; 961.8 [M+1]$^+$; 943.9 [M−H$_2$O+1]$^+$.

Product 22e (n=1, AA=PheLys(Me$_2$)). Product 22e was prepared as described for 22a. Purification was done using HPLC column Nucleodur C-18, 250×4.6, eluent ACN-H$_2$O (0.1% TFA), ramp 15-30%. MS: 998.1 [M+1]$^+$. The isolated product was desalted on Dowex 1×8 resin, eluent H$_2$O. Yield 40%.

Product 22f (n=11, AA=Leu). Product 22f was prepared as described for 22a and purified on a column, eluent: CHCl$_3$:EtOAc:MeOH:AcOH=9:7:2:0.04. Yield 48%. MS: 824.9 [M+NH$_4$]$^+$.

Product 22g (n=11, AA=Asn(DMCP). Crude 3k (obtained from 419 mg, 0.77 mmol of 2k), Peg$_{11}$NHS ester (200 mg, 0.292 mmol) and DIEA (0.06 ml, 0.35 mmol) were stirred in DCM (5 ml) for 10 h. The solvent was removed on a rotovap and the product was purified on a column, eluent CHCl$_3$:EtOAc:MeOH AcOH=4.5:3.5:1:0.02. Yield 254 mg (37%). MS: 891.1 [M+1]$^+$.

Product 22h (n=11 AA=Cit). To a solution of 3l (0.50 mmol) and DIEA (104 µl, 0.60 mmol) in DMF (2.5 ml) was added a solution of PEG$_{11}$-NHS ester (0.50 mmol) in DMF (2.5 ml). The mixture stirred for 16 h, filtered and all volatiles were removed on a rotovap at 40° C./oil pump vacuum. The residue was dissolved in a CHCl$_3$:MeOH=1:1 mixture (5 ml) and precipitated into Et$_2$O (45 ml). Precipitation was repeated two more times and the product was used without additional purification. Yield 340 mg (80%). MS: 869.4 [M+NH$_4$]$^+$; 851.9 [M+1]$^+$.

Product 22i (n=23, AA=PheCit). To a solution of 3e (0.72 mmol) and DIEA (130 µl, 0.74 mmol) in DMF (3 ml) was added a solution of PEG$_{23}$-NHS ester (0.60 mmol) in DMF (3 ml). The mixture was stirred for 16 h, filtered and all volatiles were removed on a rotovap at 40° C./oil pump vacuum. The residue was dissolved in a CHCl$_3$:MeOH=1:1 mixture (5 ml) and precipitated into Et$_2$O (45 ml). The solid product was purified on a column, eluent gradient of MeOH (7-12%) in CHCl$_3$. Yield 487 mg (53%). MS: 1555.2 [M+Na]$^+$; 1544.7 [M+NH$_4$]$^+$; 1527.7 [M+1]$^+$.

Product 22j (PEG with average MW 1000. AA=PheCit). A mixture of mPEG-1000-alcohol (Fluka) (0.173 g, 0.173 mmol), N,N-disuccinimidyl carbonate (62 mg, 0.242 mmol), and TEA (0.101 ml, 0.726 mmol) were stirred in MeCN (1 ml) for 16 h. All volatiles were removed on a rotovap and the crude residue was dissolved in CHCl$_3$ (10 ml). The organic layer was washed with H$_2$O (1 ml, pH=5), then brine, dried over Na$_2$SO$_4$ and concentrated to afford PEG-1000-NHS carbonate. This product was stirred for 16 h with 3e (0.121 mmol) and DIEA (30 µl, 0.173 mmol) in DMF (1 ml), filtered and all volatiles were removed on a rotovap at 40° C./oil pump vacuum. The residue was dissolved in a CHCl$_3$:MeOH=1:1 mixture (5 ml) and precipitated into Et$_2$O (45 ml). Precipitation was repeated two more times and the product was used without additional purification. Yield 134 mg (79%).

Product 22k (n=23, AA=ValCit). To a solution of 3g (1.0 mmol) and DIEA (183 µl, 1.04 mmol) in DMF (4 ml) was added a solution of PEG$_{23}$-NHS ester (0.87 mmol) in DMF (4 ml). The mixture was stirred for 16 h, filtered and all volatiles were removed on a rotovap at 40° C./oil pump vacuum. The residue was dissolved in a CHCl$_3$:MeOH=1:1 mixture (5 ml) and precipitated into Et$_2$O (45 ml). Precipitation was repeated two more times and the product was used without additional purification. Yield 1.0 g (77%). MS: 1496.1 [M+NH$_4$]$^+$; 1479.3 [M+1]$^+$.

Figure 10:
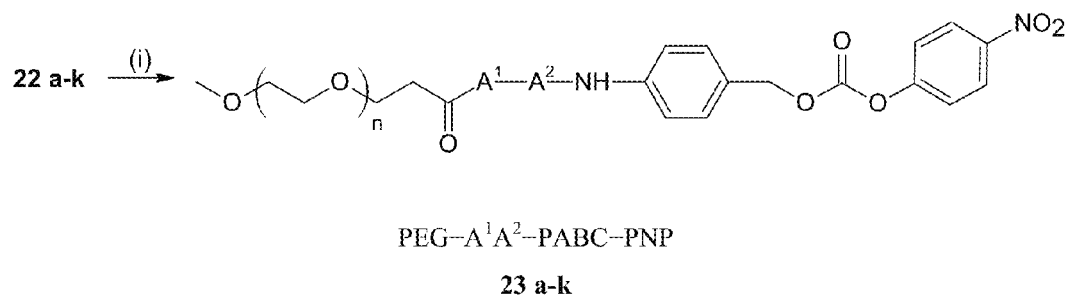
FIG. 10. Illustration showing formation of (A) and (B) PEG-AA-PABC-PNP.
Figure 10:
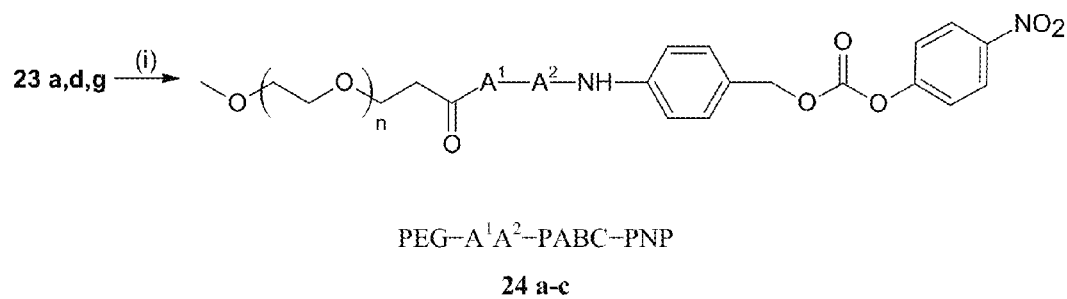

PEG-AA-PABC-PNP 23a-k (FIG. 10A)

For product 23a (n=11, AA=Glu(2PhiPr)Gly), product 22a (274 mg, 0.274 mmol) in DCM (15 ml) was stirred in the dark with (PNP)$_2$CO (418 mg, 1.372 mmol) and DIEA (0.143 ml, 0.823 mmol) for 15 h. The solvent was removed on a rotovap and the product was purified on a column, eluent 4% MeOH, 0.2% AcOH in CHCl$_3$. Yield 260 mg (81%). MS: 1180.7 [M+NH$_4$]$^+$.

For product 23b (n=11, AA=PheCit), a solution of 22b (419 mg, 0.42 mmol), (PNP)$_2$CO (766 mg, 2.52 mmol) and DIEA (263 µl, 1.52 mmol) in dioxane (4 ml) was stirred in the dark at 50° C. for 15 h and all volatiles were removed on a rotovap. The residual DIEA was removed by two consecutive evaporations of DMF on a rotovap at 40° C./oil pump vacuum and the product was purified on a column, eluent CHCl$_3$:EtOAc:MeOH (4.5:5:0.5) followed by CHCl$_3$:MeOH (9:1). Yield 390 mg (80%). MS: 1181.2 [M+NH$_4$]$^+$, 1164.2 [M+1]$^+$.

For product 23c (n=11, AA=ValCit), a solution of 22c (273 mg, 0.287 mmol), (PNP)$_2$CO (874 mg, 2.88 mmol) and DIEA (0.3 ml, 1.72 mmol) in 1,4-dioxane (22 ml) was stirred in the dark for 24 h at 50° C. The solvent was removed on rotovap at 40° C./oil pump and the product was purified on a column, eluent: CHCl$_3$:EtOAc:MeOH=16:3:1 followed by 12-15% MeOH in CHCl$_3$ Yield 163 mg (51%). MS: 1116.0 [M+1]$^+$.

Product 23d (n=1, AA=AlaAsn(DMCP)) was prepared as described in the preparation of 23b. The product was purified on a column, eluent CHCl$_3$:EtOAc:MeOH (9:2:1). Yield 77%. MS: 1144.0 [M+NH$_4$]$^+$; 1127.3 [M+1]$^+$.

Product 23e (n=1, AA=PheLys(Me)$_2$) was prepared as described for 23a and purified on a column, eluent: 10% MeOH, 0.2% AcOH in CHCl$_3$. Yield 63%. MS: 1163.1 [M+1]$^+$.

Product 23f (n=1, AA=Leu) was prepared as described for 23c using only 5 equivalents of (PNP)$_2$CO and 3 equivalents of DIEA applying heat for 24 h. The product was purified on a column, eluent gradient of MeOH (7-12%) in CHCl$_3$. Yield 75%. MS: 972 [M+1]$^+$.

Product 23g (n=11, AA=Asn(DMCP)) was prepared as described for 23f and the crude product was used in the following step without additional purification. MS: 1073.4 [M+18]$^+$.

For product 23h (n=11, AA=Cit), solution of 22h (340 mg, 0.40 mmol), (PNP)$_2$CO (608 mg, 2.00 mmol) and DIEA (208 µl, 1.20 mmol) in DCM (4 ml) was stirred in the dark at 30° C. for 15 h and all volatiles were removed on a rotovap. The residual DIEA was removed by two consecutive evaporations of DMF on a rotovap at 40° C./oil pump vacuum and the product was purified on a column, eluent CHCl$_3$:EtOAc:MeOH (7:2.5:0.5) followed by a gradient of MeOH (8-14%) in CHCl$_3$. Yield 390 mg (80%). MS: 1034.3 [M+NH$_4$]$^+$; 1016.9 [M+1]$^+$.

Product 23i (n=23, AA=PheCit) was prepared as described in the preparation of 23b and purified on a column, eluent CHCl$_3$:EtOAc:MeOH (4.5:5:0.5) followed by a gradient of MeOH (6-12%) in CHCl$_3$. Yield 86%. MS: 1711.4 [M+NH$_4$]$^+$; 1694.4 [M+1]$^+$.

Product 23j (PEG 1000K AA=PheCit) was prepared as described in the preparation of 23b and purified on a column, eluent CHCl$_3$:EtOAc:MeOH (4.5:5:0.5) followed by a gradient of MeOH (6-12%) in CHCl$_3$. Yield 72%.

Product 23k (n=23, AA=ValCit) was prepared as described in the preparation of 23b, and the product purified with HPLC. Column: Luna (Phenomenex) 5 u, C-8, 100 A. Mobile phase: ACN-H$_2$O (F$_3$CO$_2$H 0.01%), ACN gradient 30-37%, 31 min. Yield: 530 mg (48%). MS: 1666.4 [M+Na]$^+$; 1644.2 [M+1]$^+$.

PEG-AA-PABC-PNP 24a-c, AA Deprotection (FIG. 10B).

Product 24a (n=11, AA=GluGly). Product 23a (250 mg, 0.215 mmol) was stirred in a 3% TFA solution of CHCl$_3$ (16 ml) for 35 min, concentrated on a rotovap and dried in vacuo. Yield 224 mg (100%) (MS: 1062.6 [M+NH$_4$]$^+$; 1045.9 [M+1]$^+$.

Product 24b (n=11, AA=AlaAsn-PABC-PNP). Compound 23d was stirred for 1.5 h in a mixture of TFA:DCM (3:1) and all volatiles were removed on a rotovap at 20° C. The product was purified on a column, eluent gradient of MeOH (6-12%) in CHCl$_3$. Yield 30%. MS: 1066.7 [M+Na]$^+$, 1062.0 [M+NH$_4$]$^+$; 1045.2 [M+1]$^+$.

Product 24c (n=11, AA=Asn). A reaction flask with 23g (160 mg, 0.143 mmol) was chilled to 0° C. and a cold mixture of TFA:H$_2$O (9:1) (12.5 ml) was added. The mixture was stirred for 1.5 h and was diluted with cold H$_2$O (50 ml). The stirring was continued for 20 min at 20° C. The precipitate was filtered off and rinsed with H$_2$O. All volatiles were removed on a rotovap at 40° C. and the product was purified on a column, eluent CHCl$_3$:EtOAc:MeOH:AcOH=4.5:3.5:1.2:0.02. Yield 43 mg (30%). MS: 974.0 [M+1]$^+$.

TABLE 3

Final PEG-L-A$_1$A$_2$-PABC used for conjugate preparation.

| compound | | | | |
|---|---|---|---|---|
| PEG$_n$-AA-PABA | PEG$_n$-AA-(PNP) | AA A$^1$ | A$^2$ | size |
| 22 | 23a | Glu(2PhiPr) | Gly | n = 11 |
| 22 | 23b | Phe | Cit | n = 11 |
| 22 | 23c | Val | Cit | n = 11 |

TABLE 3-continued

Final PEG-L-A₁A₂-PABC used for conjugate preparation.

| PEG$_n$-AA-PABA | compound PEG$_n$-AA- (PNP) | AA A¹ | AA A² | size |
|---|---|---|---|---|
| 22 | 23d | Ala | Asn(DMCP) | n = 11 |
| 22 | 23e | Phe | Lys(CH₃)₂ | n = 11 |
| 22 | 23f | Leu | — | n = 11 |
| 22 | 23g | Asn(DMCP) | — | n = 11 |
| 22 | 23h | Cit | — | n = 11 |
| 22 | 23i | Phe | Cit | n = 23 |
| 22 | 23j | Phe | Cit | 1 kDa |
| 22 | 23k | Val | Cit | n = 23 |
|  | 24a | Glu | Gly | n = 11 |
|  | 24b | Ala | Asn | n = 11 |
|  | 24c | Asn | — | n = 11 |

Example 2

Synthesis or RGD Ligands

A. RGD-PEG-Thioate

1. RGD Mimic #1-PEG$_8$-Thioate, MW 982.1.

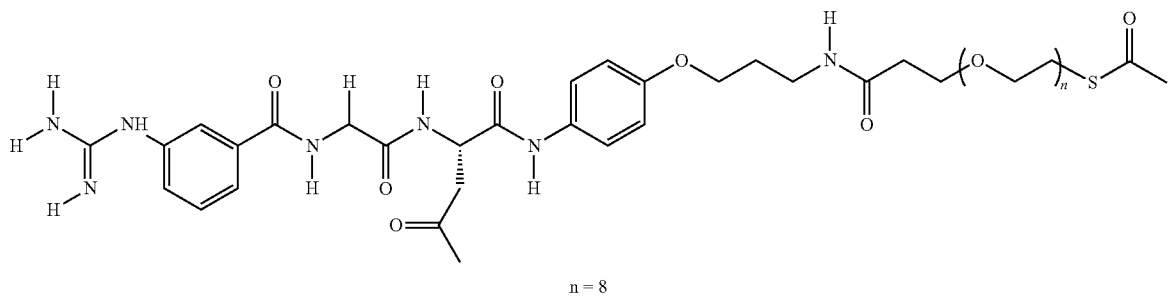

n = 8

2. RGD Mimic #2-PEG$_8$-Thioate, MW 1022.2.

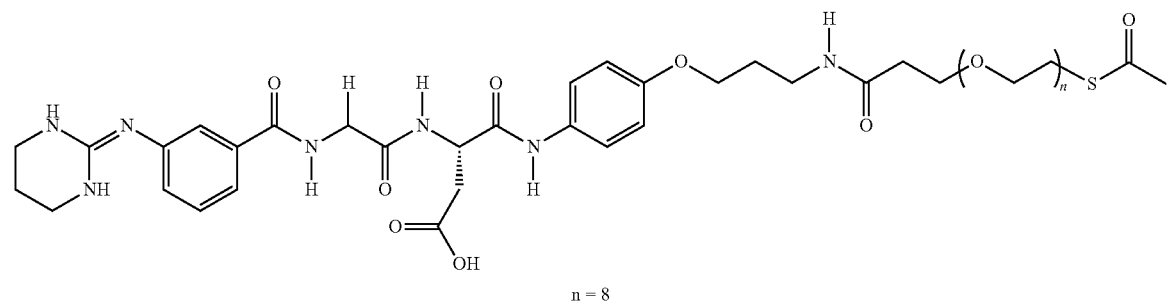

n = 8

3. RGD Mimic #3-PEG$_8$-Thioate, MW 1080.2.

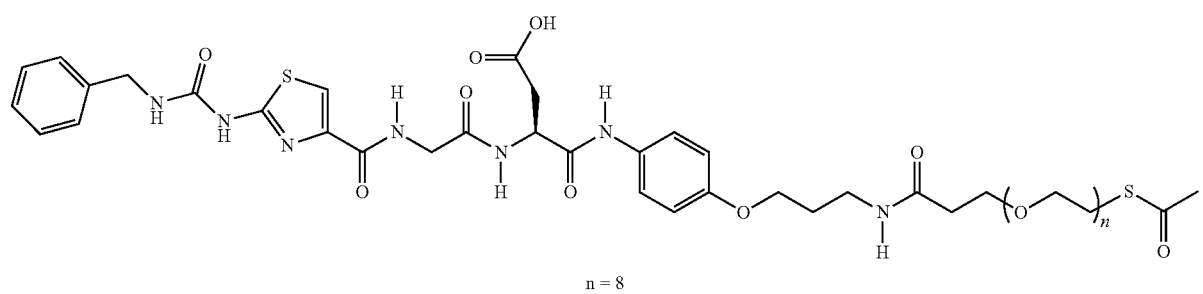

n = 8

4. RGD Mimic #3-PEG$_{12}$-Thioate, MW 1212.4.
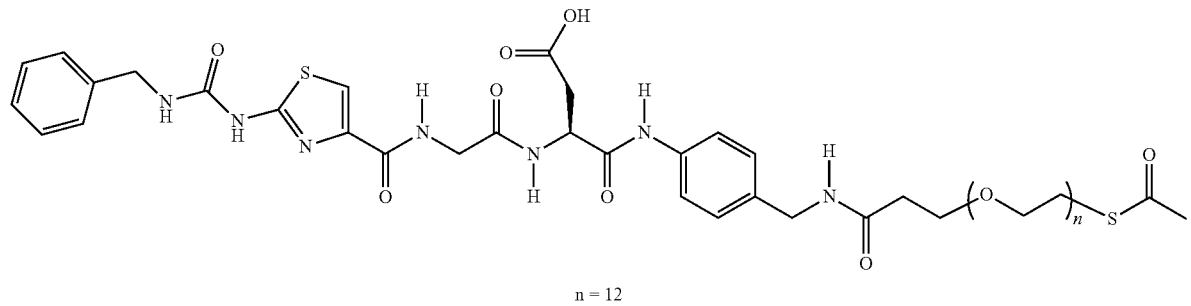
n = 12
B. RGD-HyNic
1. RGD Mimic #1-PEG$_{12}$-HyNic, MW 1272.
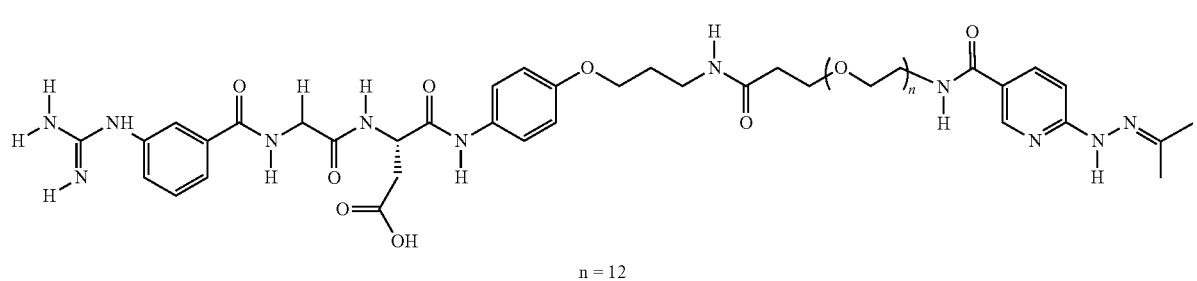
n = 12
2. RGD Mimic #1a-HyNic, MW 802.8.
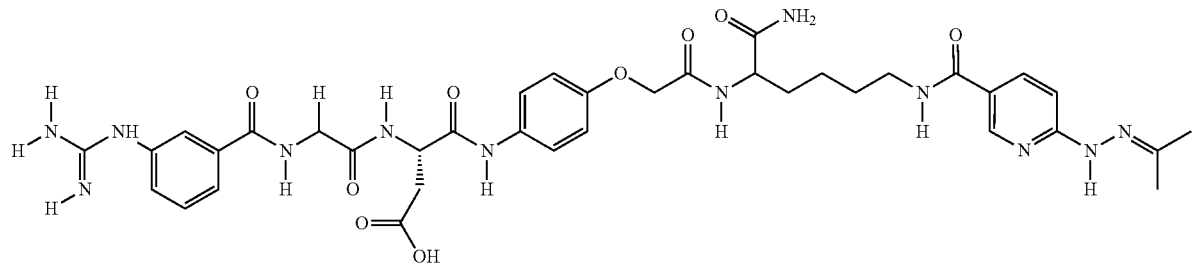 [SMILES: [H]/N=C(\N)Nc1cccc(C(=O)NCC(=O)N[C@@H](CC(=O)O)C(=O)Nc2ccc(OCC(=O)NC(CCCCNC(=O)c3ccc(NN=C(C)C)nc3)C(N)=O)cc2)c1]
3. RGD Mimic #1b-HyNic, MW 830.9 (RGD).
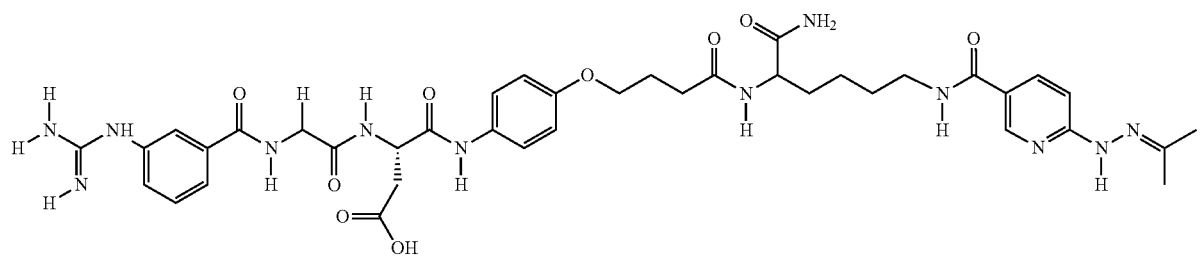 [SMILES: [H]/N=C(\N)Nc1cccc(C(=O)NCC(=O)N[C@@H](CC(=O)O)C(=O)Nc2ccc(OCCCC(=O)NC(CCCCNC(=O)c3ccc(NN=C(C)C)nc3)C(N)=O)cc2)c1]

C. RGE-PEG$_{12}$-HyNic (control). MW 1282

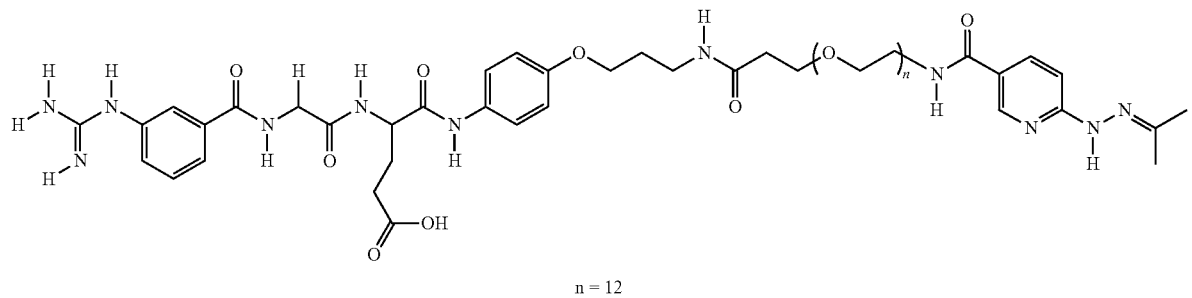

n = 12

D. RGD Peptide-HyNic: RGD4C, [NH$_2$-ACD-CRGDCFCG-Lys(e-6-HyNic); SEQ ID 5], MW 1407.83

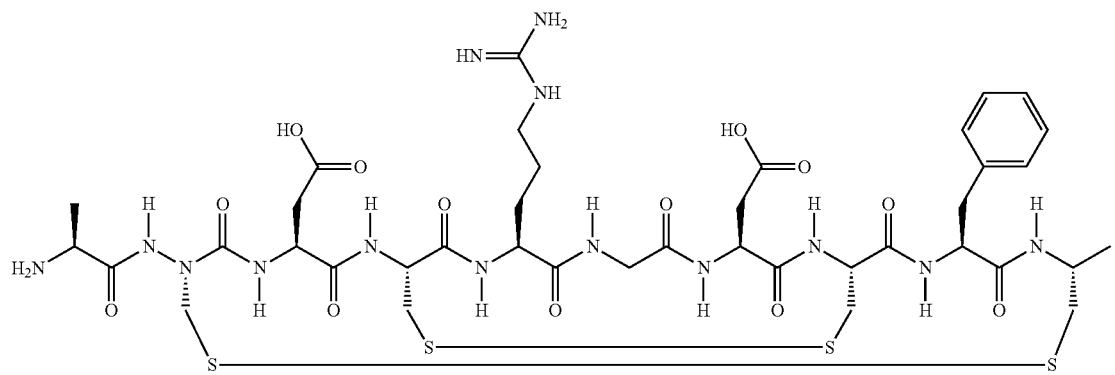

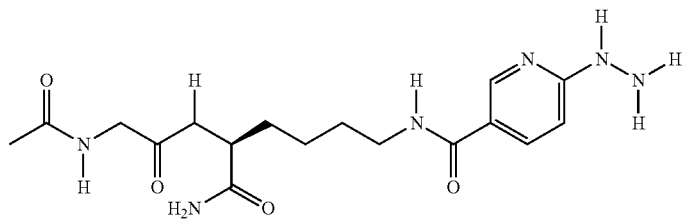

Example 3

Reversible Modification of Amphipathic Membrane Active Polyamines

Linkage of protease cleavable masking agents to amine-containing polymers—formation of p-acylamidobenzyl carbamate linkages.

A. RGD-PEG-Thioate

Cy3-labeled polymer was combined with SPDP-PEG$_{24}$-FCit-para-nitrophenol at desired ratios in 100 mM HEPES pH 9.0 buffer for 1 h at RT. The SPDP-PEG$_{24}$-FCit-modified polymer was then reacted with PEG$_{12}$-FCit at a weight ratio of 1:8 (polymer:PEG$_{12}$-FCit) in 100 mM HEPES, pH 9.0 buffer for 1 h at RT. The modified polymer was then purified using a sephadex G-50 spin column.

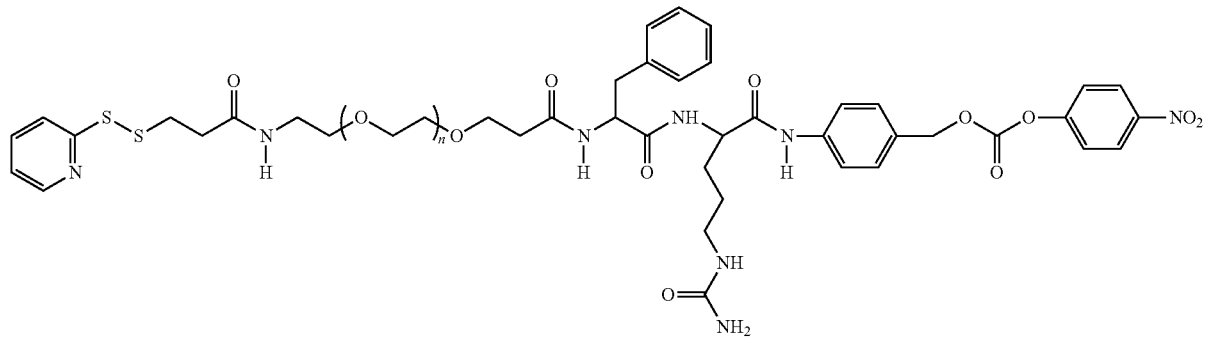

SPDP-PEG24-FCit (n = 23)

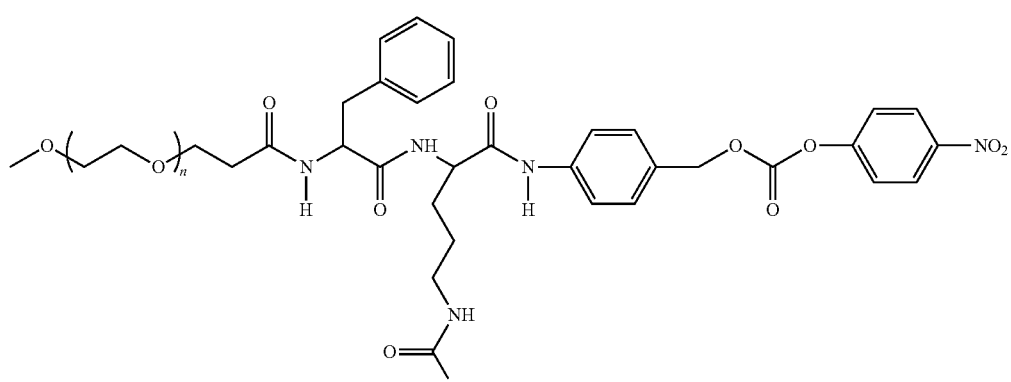

PEG₁₂-FCit (n = 11)

RGD-PEG-Thioate mimic was deacetylated with hydroxylamine at a molar ratio of 1:5 (RGD-PEG-Thioate mimic: hydroxylamine) in PBS pH 7.4 at RT for 2 h.

Modified polymer was combined with deacetylated RGD-PEG-Thioate mimic at a weight ratio of 1:1 (polymer:RGD) in PBS pH 7.4 at RT for a minimum of 4 h to form the polymer RGD conjugate. The polymer-RGD conjugate was purified using a sephadex G-50 spin column.

Conjugation efficiency was quantified by measuring Absorbance of the polymer-RGD conjugate at 343 nm using an extinction coefficient of $8.08 \times 10^3$ M$^{-1}$ cm$^{-1}$ for pyridine 2-thione.

Molar concentration of polymer (mM) =

$$\frac{\text{weight concentration of polymer (mg/ml)}}{\text{molecular weight of polymer (Dalton)}} \times 1000$$

Molar concentration of RGD (mM) =

$$\frac{[A_{343}(\text{conj.}-RGD^*) - A_{343}(\text{conj. no }RGD\text{ control})]}{8.08}$$

(*prior to sephadex G-50 purification)

Number of RGD per polymer = $\frac{\text{molar concentration }RGD\text{ (mM)}}{\text{molar concentration of polymer (mM)}}$ Polymer-RGD conjugates were diluted with isotonic glucose solution to desired concentrations.

$$\frac{mg}{ml}\text{polymer} = \frac{\text{conj. Cy3 fluorescence post-purification}}{\text{conj. Cy3 fluorescence pre-purification}} \times \frac{mg}{ml}\text{conj. pre-purification}$$

B. RGD-PEG-HyNic

Cy3-labeled polymer was combined with aldehyde-PEG₁₂/₂₄-TFP (Quanta Biodesign #10082) at desired ratios in 100 mM HEPES pH 9.0 buffer for 1 h at RT. The aldehyde-PEG₁₂/₂₄-TFP-modified polymer was then reacted with PEG₁₂-FCit at a weight ratio of 1:8 (polymer:PEG₁₂-FCit) in 100 mM HEPES, pH 9.0 buffer for 1 h at RT. The modified polymer was then purified using a sephadex G-50 spin column.

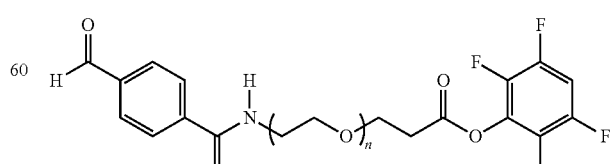

aldehyde-PEG₂₄-TFP (n = 12 or 24)

Modified polymer was combined with RGD-HyNic mimic at a weight ratio of 1:0.7 (polymer:RGD) in 50 mM MES, pH 5.0 buffer at RT for a minimum of 4 h to form the polymer RGD conjugate. The polymer-RGD conjugate was purified using a sephadex G-50 spin column.

Conjugation efficiency was quantified by measuring Absorbance of the polymer-RGD conjugate at 354 nm using an extinction coefficient of $2.9 \times 10^1$ $M^{-1}$ $cm^{-1}$ for bis-aryl hydrazone bond.

Molar concentration of polymer (mM) =
$$\frac{\text{weight concentration of polymer (mg/ml)}}{\text{molecular weight of polymer (Dalton)}} \times 1000$$

Molar concentration of $RGD$ (mM) =
$$\frac{[A_{343}(\text{conj.}-RGD) - A_{343}(\text{conj. no } RGD \text{ control})]}{29}$$

Number of $RGD$ per polymer = $\frac{\text{molar concentration } RGD \text{ (mM)}}{\text{molar concentration of polymer(mM)}}$ Polymer-RGD conjugates were diluted with isotonic glucose solution to desired concentrations.

polymer$\left(\frac{mg}{ml}\right)$ =
$$\frac{\text{conj. Cy3 fluorescence post-purification}}{\text{conj. Cy3 fluorescence pre-purification}} \times \frac{mg}{ml} \text{conj. pre-purification}$$

Example 4

Modification of Polyamines with PEG Protease Cleavable Masking Agents

Activated (amine reactive) carbonates of p-acylamidobenzyl alcohol derivatives are reacted with amino groups of amphipathic membrane active polyamines in $H_2O$ at pH>8 to yield a p-acylamidobenzyl carbamate.

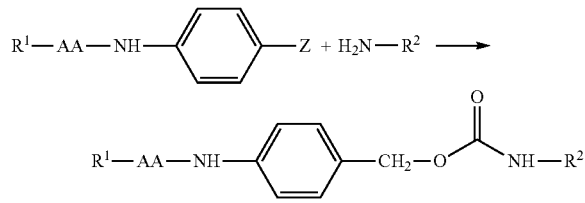

$R^1$ comprises a PEG,
$R^2$ is an amphipathic membrane active polyamine,
AA is a dipeptide (either protected or unprotected), and
Z is an amine-reactive carbonate.

To xmg polymer is added 12xmg of HEPES free base in isotonic glucose. To the buffered polymer solution is added 2x to 16xmg 200 mg/ml dipeptide masking agent in DMF. In some applications, the polymer is modified with 2xmg dipeptide masking agent followed by attachment of siRNA. The polymer-siRNA conjugate is then further modified with 6x to 8xmg dipeptide masking agent.

Example 5

Conjugate Formulation

A. Formation of siRNA Delivery Conjugate Using RGD-PEG-Thioate and PEG-Dipeptide Masking Agents The indicated polymer was reacted with SMPT at a weight ratio of 1:0.015 (polymer:SMPT) in 5 mM HEPES, pH 8.0 buffer for 1 h at RT.

The SMPT-modified polymer was then reacted with SPDP-PEG$_{24}$-FCit at desired ratios for 1 h at RT. The modified polymer was then reacted with PEG$_{12}$-FCit at a weight ratio of 1:2 (polymer:PEG$_{12}$-FCit) in 100 mM HEPES, pH 9.0 buffer for 1 h at RT. The modified polymer was then reacted overnight with SATA-siRNA at a weight ratio of 1:0.2 (polymer:SATA-siRNA) in 100 mM HEPES, pH 9.0 buffer at RT to attach the siRNA. Next, the modified polymer was reacted with PEG$_{12}$-FCit at a weight ratio of 1:6 (polymer:PEG$_{12}$-FCit) in 100 mM HEPES, pH 9.0 buffer for 1 h at RT. The resultant conjugate was purified using a sephadex G-50 spin column.

Deacetylated RGD-PEG-thioate was conjugated to the modified polymer to form the RGD-conjugate by reaction with the modified polymer at a weight ratio of 1:1 (polymer: RGD-PEG-thiol) in PBS pH 7.4 at RT for a minimum of 4 h. The conjugate was purified using a sephadex G-50 spin column. RGD targeting ligand conjugation efficiency was determined as described above and found to be 3.5 and 21 RGD ligands per 42K unmodified polymer.

B. Formation of siRNA Delivery Conjugate Using RGD-PEG-HyNic and PEG-Dipeptide Masking Agents 1) Protocol 1.

The indicated polymer was reacted with SMPT at a weight ratio of 1:0.015 (polymer:SMPT) in 5 mM HEPES, pH 8.0 buffer for 1 h at RT.

The SMPT-modified polymer was then reacted with aldehyde-PEG-dipeptide masking agent (aldehyde-PEG$_{12}$-FCit or aldehyde-PEG$_{24}$-ACit) at desired ratios for 1 h at RT. The modified polymer was then reacted with PEG$_{12}$-dipeptide masking agent (PEG$_{12}$-FCit, PEG$_{12}$-ACit or PEG$_{24}$-ACit) at a weight ratio of 1:2 (polymer:PEG) in 100 mM HEPES, pH 9.0 buffer for 1 h at RT. The modified polymer was then reacted overnight with SATA-siRNA at a weight ratio of 1:0.2 (polymer:SATA-siRNA) in 100 mM HEPES, pH 9.0 buffer at RT to attach the siRNA. Next, the modified polymer was reacted with protease cleavable PEG (PEG$_{12}$-FCit or PEG$_{12}$-ACit or PEG$_{24}$-ACit) at a weight ratio of 1:6 (polymer:PEG) in 100 mM HEPES, pH 9.0 buffer for 1 h at RT. The resultant conjugate was purified using a sephadex G-50 spin column.

RGD-HyNic (Example 2B) was attached to the modified polymer to form the full delivery conjugate by reaction with the modified polymer at a weight ratio of 1:0.7 (polymer: RGD-HyNic mimic) in 50 mM MES, pH 5.0 buffer for a minimum of 4 h at RT. The conjugate was purified using a sephadex G-50 spin column. RGD ligand attachment efficiency was determined as described above.

2) Protocol 2.

The indicated polymer was reacted with SMPT at a weight ratio of 1:0.015 (polymer:SMPT) in 5 mM HEPES, pH 8.0 buffer for 1 h at RT.

The SMPT-modified polymer was then reacted with aldehyde-PEG-dipeptide masking agent (aldehyde-PEG$_{24}$-ACit) at a weight ratio of 1:0.5 (polymer:PEG) and with PEG-dipeptide masking agent (PEG$_{12}$-FCit, PEG$_{12}$-ACit or PEG$_{24}$-ACit) at a weight ratio of 1:2 (polymer:PEG) in 100 mM HEPES, pH 9.0 buffer for 1 h at RT. The modified polymer was then reacted overnight with SATA-siRNA at a weight ratio of 1:0.2 (polymer:SATA-siRNA) in 100 mM HEPES, pH 9.0 buffer at RT to attach the siRNA. Next, the modified polymer was reacted with protease cleavable-PEG (PEG$_{12}$-FCit or PEG$_{12}$-ACit or PEG$_{24}$-ACit) at a weight ratio of 1:6 (polymer:PEG) in 100 mM HEPES, pH 9.0 buffer for 1 h at RT.

RGD-HyNic (Example 2B) was attached to the modified polymer to form the full conjugate by reaction with the modified polymer at a weight ratio of 1:0.7 (polymer:RGD-HyNic) in 69 mM hydrogen chloride solution (HCl) overnight at RT. RGD ligand attachment efficiency was determined as described above.

3) Protocol 3.

The indicated polymer was reacted with SMPT at a weight ratio of 1:0.015 (polymer:SMPT) in 5 mM HEPES, pH 8.0 buffer for 1 h at RT.

The SMPT-modified polymer was then reacted with aldehyde-PEG-dipeptide masking agent (aldehyde-PEG$_{24}$-ACit) at a weight ratio of 1:0.5 (polymer:PEG) and with PEG-dipeptide masking agent (PEG$_{12}$-FCit, PEG$_{12}$-ACit or PEG$_{24}$-ACit) at a weight ratio of 1:2 (polymer:PEG) in 50 mM HEPES, pH 9.0 buffer for 1 h at RT. The modified polymer was then reacted overnight with SATA-siRNA at a weight ratio of 1:0.2 (polymer:SATA-siRNA) in 50 mM HEPES, pH 9.0 buffer at RT to attach the siRNA. Next, the modified polymer was reacted with protease cleavable-PEG (PEG$_{12}$-FCit or PEG$_{12}$-ACit or PEG$_{24}$-ACit) at a weight ratio of 1:6 (polymer:PEG) in 50 mM HEPES, pH 9.0 buffer for 1 h at RT.

RGD-HyNic (Example 2B) was attached to the modified polymer to form the full delivery conjugate by reaction with the modified polymer at a weight ratio of 1:0.7 (polymer:RGD-HyNic mimic) in 100 mM MES free acid solution overnight at RT. RGD targeting ligand conjugation efficiency was determined as described above.

4) Protocol 4.

The indicated polymer was reacted with Azido-PEG4-NHS at a weight ratio of 1:0.015 (polymer:Azido) in 5 mM HEPES, pH 8.0 buffer for 1 h at RT.

The Azido-modified polymer was then reacted with aldehyde-PEG-dipeptide masking agent (aldehyde-PEG$_{24}$-ACit) at a weight ratio of 1:0.5 (polymer:PEG) and with PEG-dipeptide masking agent (PEG$_{12}$-ACit) at a weight ratio of 1:2 (polymer:PEG) in 50 mM HEPES, pH 9.0 buffer for 1 h at RT. The modified polymer was then reacted overnight with Alkyne-siRNA at a weight ratio of 1:0.2 (polymer:Alkyne-siRNA) in 50 mM HEPES, pH 9.0 buffer at RT to attach the siRNA. Next, the modified polymer was reacted with protease cleavable-PEG (PEG$_{12}$-ACit) at a weight ratio of 1:6 (polymer:PEG) in 50 mM HEPES, pH 9.0 buffer for 1 h at RT.

RGD-HyNic (Example 2B) was attached to the modified polymer to form the full delivery conjugate by reaction with the modified polymer at a weight ratio of 1:0.7 (polymer:RGD-HyNic mimic) in 100 mM sodium acetate-acetic acid buffer solution, pH 5.0 overnight at RT. RGD targeting ligand conjugation efficiency was determined as described above.

5) Protocol 5.

The mono azide-polymer was reacted with aldehyde-PEG-dipeptide masking agent (aldehyde-PEG$_{24}$-ACit) at a weight ratio of 1:0.5 (polymer:PEG) and with PEG-dipeptide masking agent (PEG$_{12}$-ACit) at a weight ratio of 1:2 (polymer:PEG) in 50 mM HEPES, pH 9.0 buffer for 1 h at RT. The modified polymer was then reacted overnight with Alkyne-siRNA at a weight ratio of 1:0.2 (polymer:Alkyne-siRNA) in 50 mM HEPES, pH 9.0 buffer at RT to attach the siRNA. Next, the modified polymer was reacted with protease cleavable-PEG (PEG$_{12}$-ACit) at a weight ratio of 1:6 (polymer:PEG) in 50 mM HEPES, pH 9.0 buffer for 1 h at RT.

RGD-HyNic (Example 2B) was attached to the modified polymer to form the full delivery conjugate by reaction with the modified polymer at a weight ratio of 1:0.7 (polymer:RGD-HyNic mimic) in 100 mM sodium acetate-acetic acid buffer solution, pH 5.0 overnight at RT. RGD targeting ligand conjugation efficiency was determined as described above.

Example 6

In Vitro Cell Binding

Tumor cells, at 50,000/ml in 2 ml, were seeded on glass coverslips in 6-well plates for 24 h. 5 µg/ml Cy3-labeled RGD-PEG-Thioate or Cy3-labeled RGD-PEG-HyNic (protocols 1-5) modified polymer (50 µl of 0.2 mg/ml, RGD-PEG, RGD #1) was added drop-wise to cells and the cells were incubated for 24 h at 37° C. Cells were washed 2× with PBS and fixed in 10% formalin solution or 30 min. After fixation, cells were washed 2× with PBS.

Cells were stained with Alexa Fluor 488 phalloidin (2 unit/ml) and ToPro-3 iodide (0.2 µM) for 20 min to stain actin and nuclei, respectively; followed by 2× wash with PBS. Coverslips were mounted to slides with Vectashield mounting medium and fluorescent signal was then captured with a Zeiss LSM 710 laser scanning confocal microscope. Cellular uptake of RDG-modified polyamines was determined by the presence of intracellular Cy3 fluorescence. Cy3 signal intensity in various types of tumor cells is summarized in the following Table 4 (5: highest; 1: lowest).

TABLE 4

Tumor Cell Uptake of RDG-modified polyamines

| cell line | origin | RGD-polymer internalization |
|---|---|---|
| A498 | kidney cancer | 5 |
| ACHN | kidney cancer | 5 |
| CAKI-2 | kidney cancer | 5 |
| 769-P | kidney cancer | 5 |
| 786-O | kidney cancer | 3 |
| A375 | melanoma | 3 |
| U87MG | glioblastoma | 3 |
| PANC-1 | pancreatic cancer | 4 |
| H460 | lung cancer | 3 |
| H661 | lung cancer | 3 |
| H1573 | lung cancer | 4 |
| H2126 | lung cancer | 3 |
| HT29 | Colon cancer | 3 |
| HCT116 | colon cancer | 2 |
| HepG2 | liver cancer | 3 |
| Hep3B | liver cancer | 1 |
| MCF7 | breast cancer | 2 |
| SK-BR3 | breast cancer | 2 |
| DU145 | prostate cancer | 1 |
| PC3 | prostate cancer | 1 |

TABLE 4-continued

Tumor Cell Uptake of RDG-modified polyamines

| cell line | origin | RGD-polymer internalization |
|---|---|---|
| LNCaP | prostate cancer | 1 |
| MDA-PCa-2b | prostate cancer | 1 |
| KB | oral cancer | 1 |
| CAL27 | tongue cancer | 2 |
| SCC9 | tongue cancer | 1 |
| Detroit562 | pharynx cancer | 2 |
| OVCAR3 | ovarian cancer | 1 |
| SKOV3 | ovarian cancer | 2 |
| A2780 | ovarian cancer | 2 |

Example 7

In Vivo Tumor Tracking

Cy3-labeled RGD(thiol-RGD #1)/PEG-modified Lau 1005-116C-1 (54% Ethylethoxyamine acrylate/46% Butyl acrylate RAFT Co-polymer, Fraction 1, 104 k protected MW, 76 k deprotected MW, 1.2 PDI) in isotonic glucose 100-200 µg (200 µl of 0.5 or 1 mg/ml) were injected into immunodeficient mice bearing human tumor xenografts via tail vein administration. 4 h after injection, animals were sacrificed and tumors were harvested. Whole tumors were fixed by incubation in 10% formalin solution for a minimum of 4 h. Tumors were then submerged into 30% sucrose solution overnight or until equilibrated. Saturated tumors were snap frozen in liquid nitrogen, and cryosectioned into 7 µm slices on glass slides (VWR superfrost plus micro slides). Sections were then stained with Alexa Fluor 488 phalloidin (2 unit/ml) and ToPro-3 iodide (0.2 µM) for 20 min at RT. After staining, sections were washed 2× with PBS and mounted with coverslips on top using Vectashield mounting medium and viewed with a Zeiss LSM 710 laser scanning laser confocal microscope. Representative images were taken to illustrate the tissue and cellular distribution of Cy3 fluorescence. In A498 tumor model, RGD-modified polymer penetrated deeply into tumor tissue and entered tumor cells, regardless of the location of tumor implantation (subcutaneous, liver, or kidney). Control polymers (either no RGD (PEG only) or RGE-modified) remained primarily in the vasculature, without entering tumor cells. In liver implanted HepG2 tumor model, strong RGD-conjugate penetration into tumor tissue was observed.

Example 8

In Vivo Tumor mRNA Knockdown

RGD-targeting conjugates in isotonic glucose (500 µg; 300 µl of 1.67 mg/ml) were injected into immunodeficient mice bearing human tumors xenografts via tail vein administration. 72 h after injection, animals were sacrificed and tumors were harvested. Tumor tissue was homogenized in Tri reagent (Molecular Research Center) to isolate total RNA. Relative mRNA knockdown by determined using quantitative RT-PCR.

Example 9

Orthotopic Renal Cell Carcinoma (RCC) Tumor Mice Model

A498 cells (ATCC) were grown in MEM (Invitrogen) supplemented with 10% FBS (Invitrogen). 786-0 RCC cells (ATCC) were grown in 1×MEM Non-Essential Amino Acids Solution (Invitrogen) and RPMI (Invitrogen) supplemented with 10% FBS. Cells were collected, counted, and mixed with matrigel matrix HC (BD Biosciences, 30% by volume) on ice.

Female athymic nude mice were anesthetized with ~3% isoflourane and placed in the right lateral decubitus position. A small, 0.5-1 cm, longitudinally abdominal incision in the left flank was made. Using a moist cotton swab, the left kidney was lifted out of peritoneum and gently stabilized. Just before injection, a 1.0 ml syringe was filled with the cell/Matrigel mixture and a 27 gauge needle catheter was attached to the syringe tip. The filled syringe was then attached to a syringe pump (Harvard Apparatus, model PHD2000) and primed to remove air. The tip of a 27-gauge needle catheter attached to a syringe was inserted just below the renal capsule near the caudal pole and the tip of the needle was then carefully advanced cranially along the capsule 3-4 mm. A 10 µl aliquot of 2.5:1 (vol:vol) cell/matrigel mixture containing about 200,000 cells was slowly injected into the kidney parenchyma using a syringe pump. The needle was left in the kidney for 15-20 seconds to ensure the injection was complete. The needle was then removed from the kidney and a cotton swab was placed over the injection site for 30 seconds to prevent leakage of the cells or bleeding. The kidney was then gently placed back into the abdomen and the abdominal wall was closed. Three (3) weeks after implantation, tumor progression was evaluated by visual examination and measurement after euthanasia. For most studies, tumor mice were used 5-6 weeks after implantation, when tumor measurements were typically around 4-8 mm.

Example 10

Subcutaneous (SQ) Tumors

For SQ tumor implantations, anesthesia was induced by placing mice in an induction chamber with 3% isoflurane. Once anesthetized, mice were placed on a drape and 3% isoflurane anesthesia was supplemented through a nose cone. Mice were positioned on their side (right or left) and injections were performed into the opposite flank. Just before injection, a 1.0 ml syringe was filled with the cell/Matrigel mixture and a 27 gauge needle catheter was attached to the syringe tip. The filled syringe was then attached to a syringe pump (Harvard Apparatus, model PHD2000) and primed to remove air. The needle was inserted in the flank just under the skin layer and cells (10 µl or 20 µl) were injected at a rate of 250 µl per minute. After the injection, the needle was removed and the mouse was placed in a recovery cage with heat provided by a water jacketed heating pad placed under the cage. Animals were returned to their housing racks once they have regained a normal level of activity.

Example 11

Liver Tumor Model

HepG2 cells were co-transfected with 2 expression vectors, pMIR85 a human placental secreted alkaline phosphatase (SEAP) vector and pMIR3 a neomycin/kanamycin-resistance gene vector, to develop cell lines with stable SEAP expression. Cells were grown in DMEM supplemented with 10% FBS and 300 µg/ml G418. HT-29 colon carcinoma cells were grown in McCoy's 5A medium supplemented with 10% FBS. For tumor implantation, cells were collected, counted, and mixed with matrigel (BD Biosciences, 40% by volume). Athymic nude mice were anesthetized with ~3% isoflourane and placed in a sternal recumbent position. A small, 1-2 cm, midline abdominal incision was made just below the xyphoid. Using a moist cotton swab, the left lobe of the liver was gently exteriorized. The left lobe of the liver was gently retracted and a syringe needle was inserted into the middle of the left lobe. Just before injection, a 1.0 ml syringe was filled with cell/Matrigel mixture and a 27 gauge needle catheter was attached to the syringe tip. The filled syringe was then attached to a syringe pump (Harvard Apparatus, model PHD2000) and primed to remove air. The syringe needle was inserted with the bevel down about 0.5 cm just under the capsule of the liver. 10 µl of cell/Matrigel mixture containing 100,000 cells, was injected into the liver using a syringe pump. The needle was left in the liver for 15-20 seconds to ensure the injection was complete. The needle was then removed from the liver and a cotton swab was placed over the injection site to prevent leakage of the cells or bleeding. The Matrigel/cells mixture formed a mass that was visible and did not disappear after removal of the needle. The liver lobe was then gently placed back into the abdomen and the abdominal wall was closed. For HepG2 tumor mice, sera were collected once per week after tumor implantation and subjected to SEAP assay to monitor tumor growth. For most studies, tumor mice were used 4-5 weeks after implantation, when tumor measurements were predicted to be around 4-8 mm based on SEAP values. For HT-29 tumor mice, based on historical observations, tumor mice were used 5-6 weeks after implantation when tumors typically reached 4-8 mm in length and width.

Example 12

Quantitative Real-Time PCR Assay

In preparation for quantitative PCR, total RNA was isolated from tissue samples homogenized in TriReagent (Molecular Research Center, Cincinnati, Ohio) following the manufacturer's protocol. Approximately 500 ng RNA was reverse-transcribed using the High Capacity cDNA Reverse Transcription Kit (Life Technologies). For human (tumor) Aha1 expression, pre-manufactured TaqMan gene expression assays for human Aha1 (Assay ID: Hs00201602_m1) and CycA (Part #: 4326316E) were used in biplex reactions in triplicate using TaqMan Gene Expression Master Mix (Life Technologies) or VeriQuest Probe Master Mix (Affymetrix). For human (tumor) EG5 expression, pre-manufactured TaqMan gene expression assays for human EG5 (Assay ID: Hs00189698_m1) and CycA (Part #: 4326316E) were used in biplex reactions in triplicate using TaqMan Gene Expression Master Mix (Life Technologies) or VeriQuest Probe Master Mix (Affymetrix). Quantitative PCR was performed by using a 7500 Fast or StepOnePlus Real-Time PCR system (Life Technologies). The $\Delta\Delta C_T$ method was used to calculate relative gene expression.

Example 13

Knockdown of Renal Cell Carcinoma Tumor Gene In Vivo

RGD targeted siRNA delivery conjugates were formed using RGD mimic #1-PEG-thioate or RGD mimic #1-PEG-HyNic. 500 µg Lau 41648-106 polymer modified with 8×PEG$_{12}$-FCit/0.5× aldehyde-PEG$_{24}$-FCit (with RGD mimic #1-PEG-HyNic using protocol #1) or SPDP-PEG$_{24}$-FCit (with RGD-PEG-thioate) and 100 µg Aha1 siRNA. Kidney RCC tumor-bearing mice were generated as described and treated with a single tail vein injection of Aha1 conjugates. Mice were euthanized 72 h after injection and total RNA was prepared from kidney tumor using Trizol reagent following manufacture's recommendation. Relative Aha1 mRNA levels were determined by RT-qPCR as described compared to mice treated with delivery buffer only. Conjugates formulated without targeting ligand or RGE control ligand exhibited 25-35% reduction in gene expression. RGD targeted conjugates exhibited 50-70% gene reduction in tumor Aha1 expression (n=3 or 4).

TABLE 5

Relative tumor Aha1 mRNA levels in orthotopic Kidney RCC tumor in mice following treatment with a single dose of Aha1 siRNA conjugates.

| Treatment | Relative human Aha1 mRNA level in tumor (%) |
| --- | --- |
| Delivery buffer (IG) | 100 ± 14 |
| No ligand-conjugate | 64 ± 2 |
| HyNic-RGE mimic #1-conjugate | 75 ± 5 |
| Thiol-RGD mimic #1-conjugate | 31 ± 4 |
| HyNic-RGD mimic #1-conjugate | 42 ± 8 |
| HyNic-RGD4C-conjugate (CS Bio) | 52 ± 14 |

Gene knockdown in animals treated with untargeted conjugates (no ligand or RGE mimic (negative control ligand) was likely the result of passive accumulation of conjugates in the tumor through the enhanced permeability and retention (EPR) effect (Torchilin, 2011). Long serum stability and circulation of the conjugates allows for significant accumulation in the tumor through EPR. Still, RGD-targeted conjugates exhibited an additional 20-40% reduction in gene expression compared to the passively targeted conjugates.

Example 14

Knockdown of Renal Cell Carcinoma Tumor Gene In Vivo

RGD mimic #1 targeted siRNA delivery conjugates were formed using RGD mimic #1-PEG and protocol #1. 500 µg Lau 41648-106 polymer was modified with 8×PEG$_{12}$-FCit/0.5× aldehyde-PEG$_{24}$-FCit, and 100 µg Aha1 siRNA. RGD mimic #1-PEG-HyNic was used as targeting ligand for these samples. Mice containing both metastatic (subcutaneous) and orthotopic kidney RCC tumors were generated as described above and treated with a single tail vein injection of Aha1 conjugates. Mice were euthanized 72 h after injection and total RNA was prepared from kidney tumor using Trizol reagent following manufacture's recommendation. Relative human (tumor) Aha1 mRNA levels at tumor implantation sites were determined by RT-qPCR as described above and normalized to mice injected with delivery buffer only. RGD-targeted conjugate exhibited 40-50% gene reduction in tumor Aha1 expression (n=3 or 4).

TABLE 6

Relative tumor Aha1 mRNA levels in orthotopic kidney or metastatic subcutaneous RCC tumors in mice following treatment with a single dose of Aha1 siRNA conjugates.

| Treatment | Tumor | Relative tumor Aha1 mRNA level (%) |
|---|---|---|
| Delivery buffer | kidney | 100 ± 7 |
| HyNic-RGD mimic #1-conjugate | kidney | 49 ± 14 |
| Delivery buffer | subcutaneous | 100 ± 6 |
| HyNic-RGD mimic #1-conjugate | subcutaneous | 59 ± 3 |

Example 15

RDG-Targeted siRNA Delivery Conjugates Delivery siRNA to Multiple Tumor Types Cancers that affect the liver include cancers originating from liver cells (e.g. hepatocellular carcinoma, HCC) and metastatic cancers originating in other tissues as the colon, lung, renal or breast. Various cancer cell types know to express $\alpha_v\beta_3$ integrin and bind to RGD-conjugates in vitro were implanted into the liver. RGD targeted siRNA delivery conjugates were formed using RGD mimic #1-HyNic or RDG mimic #1-PEG-thioate. 500 µg Lau 41648-106 polymer was modified with 8×PEG$_{12}$-FCit/0.5× aldehyde-PEG$_{24}$-FCit (protocol #1 or #5) or 8×PEG$_{12}$-FCit-/0.5× SPDP-PEG$_{24}$-FCit (using RGD-PEG-Thioate protocol) and 100 µg Aha1 siRNA. Tumor bearing mice were then treated with a single dose of Aha1 siRNA delivery conjugates administered by tail vein injection. Mice were euthanized 72 h after injection and total RNA was prepared from liver tumors using Trizol reagent following manufacture's recommendation. For each tumor type, tumor Aha1 mRNA levels were normalized tumor in mice receiving delivery buffer only. RGD-targeted conjugates exhibited 50-60% reduction in tumor Aha1 gene expression (n=3 or 4).

TABLE 7

Relative tumor Aha1 mRNA levels in various liver tumors in mice following treatment with a single dose of Aha1 siRNA conjugates.

| Treatment | Tumor cell type | Relative tumor Aha1 mRNA level (%) |
|---|---|---|
| Delivery buffer | | 100 ± sd |
| Thiol-RGD mimic #1-conjugate | RCC (A498) | 50 ± 15 |
| HyNic-RGD4C-conjugate | HCC (HepG2) | 60 ± 5 |
| HyNic-RGD mimic #1-conjugate | Colon (HT-29) | 63 ± 10 |
| HyNic-RGD mimic/click siRNA | Lung (H460) | 63 ± 8 |

Example 16

RGD-Conjugate Formulation with Different Polymer Classes

Polymer Emi 1034-68C-1
Polymer Emi 1034-81F-1
Polymer LH 1073-20C-1
RGD mimic #1 targeted siRNA delivery conjugates were formed using RGD mimic #1b and protocol #2, 400 µg Emi 1034-68C-1, Emi 1034-81F-1 or LH 1073-20C-1 polymer was modified with 8×PEG$_{12}$ ACit/0.5× aldehyde-PEG$_{24}$-ACit and 80 µg Aha1 siRNA. RGD mimic #1b was used as targeting ligand for these formulations. Orthotopic RCC tumor bearing mice were then treated with a single dose of Aha1 conjugates administered by tail vein injection. Mice were euthanized 72 h after injection and total RNA was prepared from liver tumors using Trizol reagent following manufacture's recommendation. Tumor Aha1 mRNA levels were normalized to tumor in mice receiving delivery buffer only.

TABLE 8

Relative tumor Aha1 mRNA levels in orthotopic kidney RCC tumor in mice following treatment with a single dose of Aha1 siRNA conjugates.

| Treatment | Relative tumor Aha1 mRNA level (%) |
|---|---|
| Delivery buffer | 100 ± 9.8 |
| RGD/PEG-Emi1034-68C-1 conjugate | 49 ± 4.9 |
| RGD/PEG-Emi1034-81F-1 conjugate | 42 ± 6.3 |
| RGD/PEG-Lor1073-20C-1 conjugate | 56 ± 4.5 |

Example 17

RGD-Conjugate Formulation with ACit or FCit Dipeptide Masking Reagents

RGD mimic #1 targeted siRNA delivery conjugates were formed using RGD mimic #1b and protocol #2. 400 µg Emi 1034-68C-1 polymer was modified with 8×PEG$_{12}$-FCit/0.5× aldehyde-PEG$_{12}$-FCit (for FCit dipeptide masked delivery conjugate) or 8×PEG$_{12}$-ACit/0.5× aldehyde-PEG$_{24}$-ACit (for ACit dipeptide masked delivery conjugate) and 80 µg Aha1 siRNA. RGD mimic #1b-HyNic was used as targeting ligand for these formulations. Orthotopic RCC tumor bearing mice were then treated with a single dose of Aha1 siRNA delivery conjugates administered by tail vein injection. Mice were euthanized 72 h after injection and total RNA was prepared from liver tumors using Trizol reagent following manufacture's recommendation. Tumor Aha1 mRNA levels were normalized to tumor in mice receiving delivery buffer only. There was no significant difference in gene knockdown efficacy between ACit or FCit siRNA delivery conjugates. RGD-targeted conjugates exhibited 51% or 53% reduction in tumor Aha1 gene expression (n=3) for ACit or FCit conjugates, respectively.

TABLE 9

Relative tumor Aha1 mRNA levels in orthotopic kidney RCC tumor in mice following treatment with a single dose of Aha1 siRNA conjugates.

| Treatment | Relative tumor Aha1 mRNA level (%) |
|---|---|
| Delivery buffer | 100 ± 9.8 |
| ACit RGD mimic #1b-conjugate | 49 ± 4.9 |
| FCit RGD mimic #1b-conjugate | 47 ± 7.3 |

Example 18 siRNAs siRNAs had the following sequences
Aha1 siRNA:

```
                                              (SEQ ID 3)
sense:  (NH2C6)GfgAfuGfaAfgUfgGfaGfaUfuAfgUf(invdT)

(SEQ ID 4)
antisense: pdAsCfuAfaUfcUfcCfaCfuUfcAfuCfcdTsdT
``` p=phosphate d before nucleotide=2'-deoxy s=phosphorothioate linkage f after nucleotide=2'-F substitution lower case=2'-O—CH₃ substitution RNA synthesis was performed on solid phase by conventional phosphoramidite chemistry on an ÄKTA Oligopilot 100 (GE Healthcare, Freiburg, Germany) or Mermade 12 (Bioautomation, Plano Tex.) and controlled pore glass (CPG) as solid support.

Example 19

Synthesis of Alkyne Disulfide Sense-Strand RNA Conjugate

Crude sense-strand RNA (3.4 mg, 506 nmol) with a 5' C-6 amino modification, was precipitated using sodium acetate (0.3M) in EtOH at −80° C., lyophilized, and dissolved in 300 µL 0.2M NaHCO₃, pH 8-9. Dibenzocyclooctyne-N-hydroxysuccinimidyl (Dibenzocyclooctyne-S—S—N-hydroxysuccinimidyl ester (DBCO-NHS), item #761532 Aldrich) (2.86 mg, 5060 nmol) was dissolved in 286 µL DMF and added to the RNA solution. The reaction mixture was mixed well and allowed to proceed for 2 h at RT. The reaction was monitored using RP-HPLC. After reaction completion, the reaction mixture was dried down and purified using RP-HPLC. The RNA conjugate was prepared in 45% yield (229 nmol). The purity of the RNA conjugate was determined by RP-HPLC (purity: 96.6%) and the identity was confirmed by MALDI-TOF/TOF (Mass calculated: 7164.0; Mass observed: 7164.8).

Example 20

Synthesis of 4-(Fmoc-4-Aminophenoxy) Butyric Acid

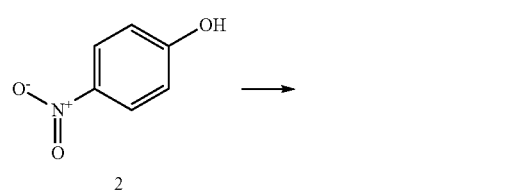

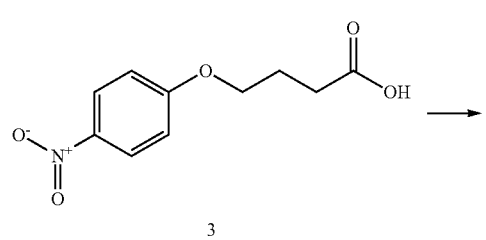

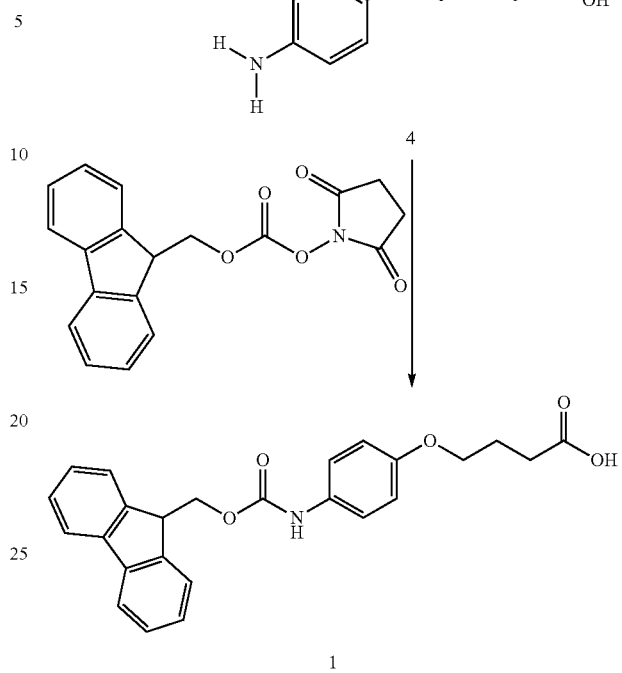

A. Synthesis of 3 p-nitro-phenol (2) (7.5 g, 53.9 mmol) was combined with ethyl 4-bromobutyrate (8.45 ml, 5.9 mmol) and K₂CO₃ (7.5 g, 5.4 mmol) in DMF (75 ml) and stirred for 2 h at 100° C. DMF was removed and the crude was diluted in a mixture of 3:1 mixture of 2 N NaOH and methanol and stirred 4 h at RT. The reaction mixture was acidified with 6M HCl. The white precipitate was collected (10.9 g 90% yield). [¹H-NMR (400 MHz, DMSO) δ: 12.165 (bs, 1H) δ: 8.175 (AA', J=Hz, 2H) δ: 7.120 (AA', J=Hz, 2H), δ: 4.122 (t, J=6.8 Hz, 2H), δ: 2.379 (t, J=6.8 Hz, 2H), δ: 1.975 (p, J=6.8 Hz, 2H)]

B. Synthesis of 4

3 (37.1 g, mmol) was dissolved in MeOH (1 L) with ammonium formate (35 g, mmol) and 10% Pd/C (Degussa Type) (3.5 g) was added. The mixture was refluxed at 65° C. overnight. The reaction was filtered with celite to yield a reddish brown solid (30.5 g, 95% yield). [¹H-NMR (400 MHz, DMSO), δ: 6.609 (AA', J=Hz, 2H) δ: 6.470 (AA', J=Hz, 2H), δ: 3.790 (t, J=6.8 Hz, 2H), δ: 2.288 (t, J=7.2 Hz, 2H), δ: 1.832 (p, J=7.2 Hz, 2H)]

C. Synthesis of 4-(Fmoc-4-Aminophenoxy) Butyric Acid (1)

4 (5.1 g, 26 mmol) was dissolved in a 6:4 a mixture of aqueous saturated sodium bicarbonate solution and THF (300 ml) to make a white slurry. Fmoc-OSu (8.82 g, 26.1 mmol) was added and the reaction was stirred for 4 h. The acetone was removed, the reaction was acidified and the off-white precipitate was collected and triturated in 1N HCl to yield 9.6 g product (88% yield, molecular weight 389.40066). [¹H-NMR (400 MHz, DMSO) δ: 9.508 (bs, 1

Hz), δ: 7.885 (d, J=7.6, 2 Hz, 2H), δ: 7.727 (d, J=6.8 Hz, 2H), δ: 7.389-7.32 (bm, 7H), δ: 7.328 (dd, J=6.8, 6.4 Hz, 2H), δ: 6.828 (d, J=7.6 Hz, 2H), δ: 4.435 (d, J=6.0 Hz, 2H), δ: 4.275 (t, J=6.4 Hz, 1H), δ: 3.897 (t, J=6.0 Hz, 2H), δ: 2.335 (t, J=7.2 Hz, 2H), δ: 1.885 (p, J=7.2 Hz)]

Reagents used: Dimethylformamide (DMF), Dichloromethane (DCM), Methanol (MeOH), H₂O(HPLC grade), Acetone, p-Nitrophenol, Ethyl 4-Bromobutyrate, Potassium Carbonate, Pd/C (Degussa type) were purchased from Sigma Aldrich and used as is. Fmoc-OSu was purchased from Novabiochem.

Example 21

Synthesis of Guanadino-Gly-Asp(OH)-APOA-PEG₁₂-HyNic-Boc

Fmoc-Gly-Asp(O-2PhiPr)-OH      2

A. Fmoc-Gly-Asp(O-2PhiPr)-OH (2). Fmoc-Gly-OH (CAS 29022-11-5) (1.57 g, 5.28 mmol) was dissolved in THF (30 ml) and set to stir in an ice water bath. NHS (0.668 g, 5.81 mmol) and DCC (1.2 g, 5.81 mmol) were added to the solution, stirred for 5 min, and the ice bath was removed. The reaction mixture was stirred for 16 h at 20° C., cooled to 0° C. for 1 h, then filtered, concentrated and dried in vacuum. The crude product was dissolved in THF (20 ml) and added to a solution of H-Asp(2-PhiPr)-OH (CAS 200336-86-3) (1.328 g, 5.28 mmol) and NaHCO₃ (600 mg, 7.14 mmol) in H₂O (30 ml). 1,2-Dimethoxyehtane (DME, 30 ml) was added to make the solution homogeneous and stirred for 16 h. THF and DME were removed on a rotovap, the residue was diluted with H₂O (150 ml) and acidified to pH=3 with 3% HCl to yield Fmoc-Gly-Asp(O-2PhiPr)-OH (2). Product was extracted 5 times with EtOAc, rinsed with brine, dried (Na₂SO₄) and concentrated and dried in vacuum. Yield 2.54 g. Crude product was used in the next step assuming 100% yield.

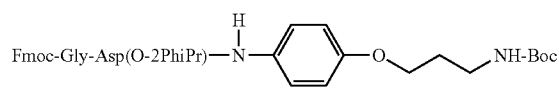

3

B. Fmoc-Gly-Asp(O-2PhiPr)-BAPOA-Boc (3). Dipeptide 2 (1.168 g, 2.2 mmol) was dissolved in DCM (20 ml) and set to stir in an ice water bath. NHS (291 mg, 2.53 mmol) and DCC (522 mg, 2.53 mmol) were added to the solution, stirred for 5 min at 0° C. and then 16 h at 20° C. The reaction mixture was cooled on an ice bath for 1 h, filtered and concentrated and dried in vacuum. The obtained NHS derivative was dissolved in DCM (15 ml) and added to a solution of 4-[3-(Boc-amino)propan-1-yloxy]-aniline (APOA-Boc, 644 mg, 2.42 mmol) (Quelever, Frederic. and Kraus *Organic & Biomolecular Chemistry*, 1(10), 1676-1683; 2003) and TEA (175 µl, 1.25 mmol). The reaction was stirred at 20° C. for 3 h and 1,4-dioxane (10 ml) was added. All volatiles were removed in vacuo. The residue was dissolved in EtOAc (200 ml), washed with 5% KHSO₄ (2×40 ml), water (1×40 ml), concentrated sodium bicarbonate solution (1×40 ml), and brine (1×40 ml). The organic layer was dried (Na₂SO₄), than concentrated and dried in vacuum. Yield 1.714 g. Crude product, Fmoc-Gly-Asp(O-2PhiPr)-BAPOA-Boc (3), was used in the next step assuming 100% yield.

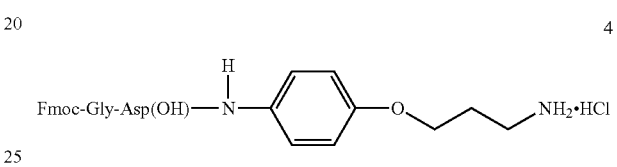

4

C. Fmoc-Gly-Asp(OH)-APOA HCl salt (4). Compound 3 (800 mg, 1.02 mmol) was treated with an ice cold solution of HCl in dioxane (4M, 22 ml) and stirred at 0° C. for 45 min. Cooling bath was removed and the suspension was concentrated. The residue was suspended in CHCl₃ (2.5 ml), diethyl ether (45 ml) was added, and the solid was separated. The reprecipitation procedure of HCl salt of 4-[3-(amino)propan-1-yloxy]-aniline (APOA) derivative was repeated twice and the product was dried in vacuo. Yield: 557 mg (92%).

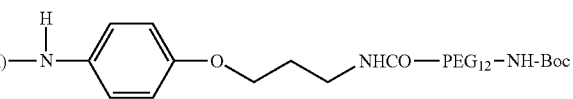

5

D. Fmoc-Gly-Asp(OH)-APOA-PEG₁₂-NH-Boc (5). To a solution containing Boc-Peg₁₂-CO₂H (Quanta Biodesign Limited 10761, 803 mg, 1.12 mmol) in DCM (8 ml) at 0° C. was added NHS (193 mg, 1.68 mmol) followed by DCC (346 mg, 1.68 mmol). Cooling was removed and stirring continued for 24 h. The reaction mixture was chilled to −20° C., filtered and concentrated. The NHS derivative was treated with a solution of compound 4 (667 mg, 1.12 mmol) and DIEA (154 µl, 0.89 mmol) in DMF (14 ml), stirred for 16 h, filtered, and concentrated. The crude residue obtained was purified by flash SiO₂ chromatography eluting

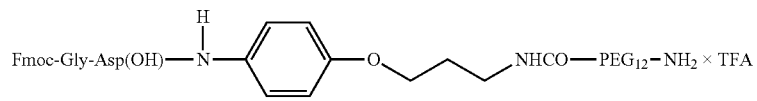

6

E. Fmoc-Gly-Asp(OH)-APOA-PEG₁₂-NH₂ (6). Compound 5 (140 mg, 0.11 mmol) was treated with TFA (3 ml)

and H₂O (1 ml). The mixture was stirred for 20 min, diluted with cold H₂O and all volatiles were removed on a rotovap. The residue was triturated 3× with Et₂O, dried in vacuo and used without further purification. Yield: 115 mg (90%).

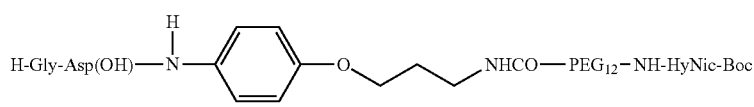

7

F. H₂N-Gly-Asp(OH)-APOA-PEG₁₂-HyNic-Boc (7). To a solution containing 6 (105 mg, 0.091 mmol) and DIEA (31 μl, 0.18 mmol) in DCM (3 ml) was added Boc-HyNic-NHS (Abrams, M. J., Juweid, M., Tenkate, C. I., Schwartz, D. A., Hauser, M. M. Gaul, F. E., Fuccello, A. J., Rubin, R. H., Strauss, H. W., Fischmann, A. J. *J. Nucl. Med.* 31, 2022-2028, 1990.) (35 mg, 0.10 mmol).

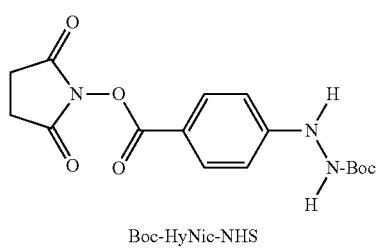

Boc-HyNic-NHS

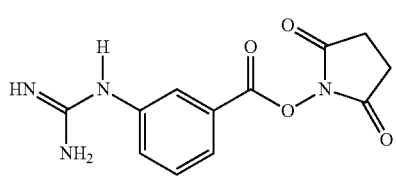

1

G. 3-Guanadinobenzoic acid-NHS ester (1). NHS (589 mg, 5.12 mmol) was added into a stirring solution of 3-guanidinobenzoic acid (1 g, 4.65 mmol; Chandrakumar, N., et al. U.S. Pat. No. 5,773,646) in DMF (25 ml), stirred for 5 min, then DCC (1.056 g, 5.12 mmol) was added into the reaction mixture. The stirring was continued for 2 h then the reaction mixture was cooled to −20° C. for 30 min, the product was filtered off, washed with cold DMF, and dried in vacuo using an oil pump. Yield: 1.283 g (100%).

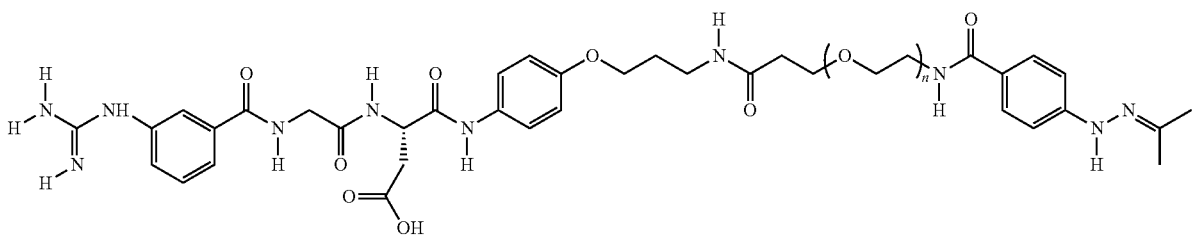

8, RGD mimic #1-PEG-HyNic, n = 12

The mixture was stirred for 16 hr, treated with ethyl amine (30 μl, 2.0M) in MeOH, and stirred for an additional 3 h (to quench the excess of unreacted Boc-HyNic-NHS). All volatiles were removed on a rotovap. The crude residue was dissolved in DMF (3 ml), then treated with TEA (400 μl) and stirred for 16 h. All volatiles removed on a rotovap with an oil pump vacuum. The crude product was purified with preparative HPLC using a Thermo Aquasil C18 column (5 u, 100 Å) eluting a gradient (18-43%) of ACN (0.1% formic acid) in H₂O (0.1% formic acid) over 30 min. Yield: 36 mg (34%).

H. Guanadino-Gly-Asp(OH)-APOA-PEG₁₂-HyNic-Boc (8). A mixture of H₂O (1 ml) and THF (0.9 ml) containing 7 (36 mg, 0.031 mmol) and NaHCO₃ (13 mg, 0.155 mmol) was treated with NHS ester of 3-guanadinobenzoic acid (1) (19.5 mg, 0.071 mmol) and stirred for 22 h. The mixture was then diluted with H₂O and THF was removed on a rotovap. The residue was suspended in water (3 ml) at pH=3 (1% HCl) and solid impurities were filtered off. Product was concentrated in vacuo, the crude residue was treated with a mixture of H₂O (0.8 ml), acetone (0.8 ml), and TFA (1.8 ml) and stirred for 40 min. Upon completion the solution was diluted with acetone (2 ml) and all volatiles were removed on a rotovap. The crude product obtained was purified with preparative HPLC using a Thermo Aquasil C18 column (5 u, 100 Å) eluting a gradient (18-43%) of ACN (0.1% formic acid) in H₂O (0.1% formic acid) over 30 min. Yield: 34 mg (89%).

Example 22

Solid Phase Synthesis of RGD Ligand

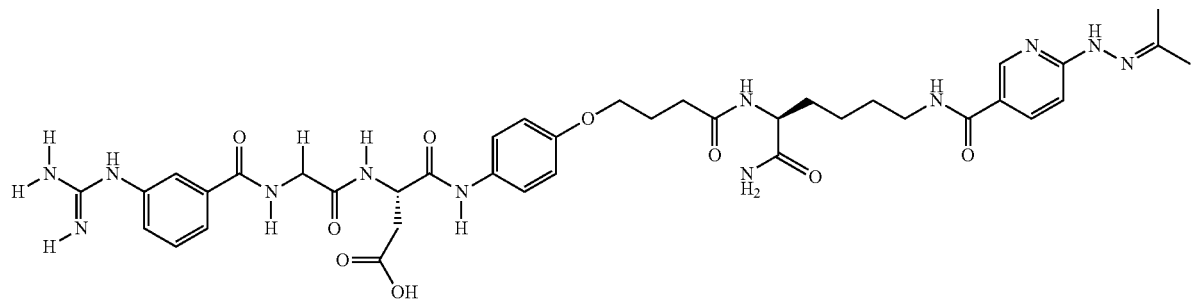 [SMILES: [H]/N=C(\N)Nc1cccc(C(=O)NCC(=O)N[C@@H](CC(=O)O)C(=O)Nc2ccc(OCCCC(=O)N[C@@H](CCCCNC(=O)c3ccc(NN=C(C)C)nc3)C(N)=O)cc2)c1]

Dimethylformamide (DMF), piperidine, dichloromethane (DCM), Diethyl ether (Et$_2$O), H$_2$O (HPLC grade), acetonitrile (ACN) (HPLC grade), triethylamine (TEA), F$_3$CCO$_2$H (TFA), and triisopropyl silane (TIPS). PyBOP (benzotriazol-1-yl-oxytripyrrolidino-phosphonium hexafluorophosphate) was purchased from Oakwood Products Inc. Rink Amide MBHA resin, Fmoc-Gly-OH, and Fmoc-Asp(tBu)-OH were purchased from Novabiochem. 4-(N-Fmoc para-aminophenoxy)-butyric acid and di-boc m-guanidino benzoic acid were synthesized using standard techniques in the art. Fritted polypropylene syringes were purchased from Torviq. Solvent A is H$_2$O:F$_3$CCO$_2$H 100:0.1 v/v. Solvent B is CH$_3$CN:F$_3$CCO$_2$H 100:0.1 v/v. Fmoc-Lys(HyNic)-OH was synthesized as previously described.

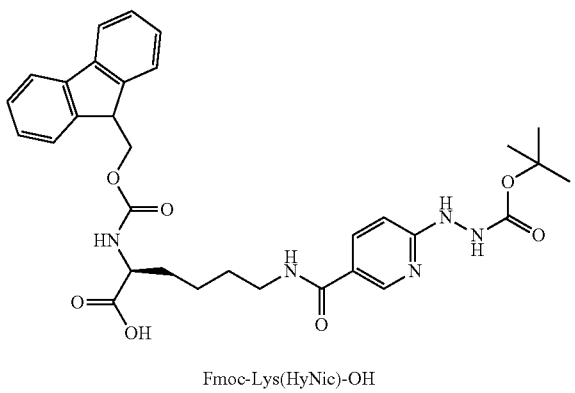

Fmoc-Lys(HyNic)-OH

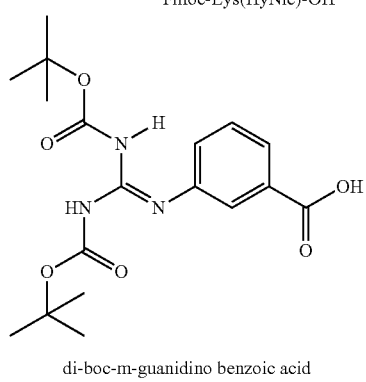

di-boc-m-guanidino benzoic acid

A. Peptide Synthesis

Rink Amide MBHA resin was placed in fritted polypropylene syringe and agitated in DCM for 2 h prior to use. The following standard solid phase peptide synthesis conditions were used. Fmoc deprotections were carried out by soaking 10 ml (per 1 mmol of resin) of a piperidine:DMF solution (20:80 v/v) for 20 min. Amide couplings were carried out by soaking the resin with 4 eq. Fmoc-amino acid, 4 eq.PyBOP and 10 eq. Triethylamine in DMF at 0.1 M concentration in DMF for 40 min.

Fmoc-Lys(HyNic)-OH, 4-(N-Fmoc para-aminophenoxy)-butyric acid, Fmoc-Asp(tBu)-OH, Fmoc-Gly-OH, and Fmoc-3-aminobenzoic acid were sequentially coupled onto the resin. Progress of amide couplings were checked using MALDI-TOF analysis. Fmoc deprotection of 4-(N-Fmoc para-aminophenoxy)-butyric acid was carried out for 40 min to ensure complete Fmoc-deprotection. The Fmoc-Asp(tBu)-OH residue was double coupled to ensure amide formation between the Fmoc-aspartate acid and the amino moiety of the 4-(aminophenoxy)-butyric acid residue. Cleavage from the resin was carried out in a TFA:H$_2$O:TIPS:Acetone (92.5:2.5:2.5:2.5 v/v/v/v) solution for 2 h. Blowing air was used to reduce TFA solution to ~10% volume, and the peptide was precipitated in Et$_2$O. The precipitate was redissolved in A:B (1:1 v/v) solvent mixture and purified using reverse phase HPLC.

B. Peptide Purification

Purification (to >90% homogeneity) was carried out on a preparative scale Shimadzu HPLC equipped with a Phenomenex Gemini C18 (250×21.2 mm, 5 μm particle) column using a 10-30% B solvent gradient over 20 min. Purity was assessed using a 10-60% B gradient over 50 min on an analytical Shimadzu HPLC equipped with a Waters xBridge C18 (4.6×250 mm, 5 μm particle) column. Lyophilization of the HPLC fractions yielded the purified peptide as a TFA salt.

Example 23

A. Synthesis of PEG$_{12/24}$-FCit-PABOC-PNP

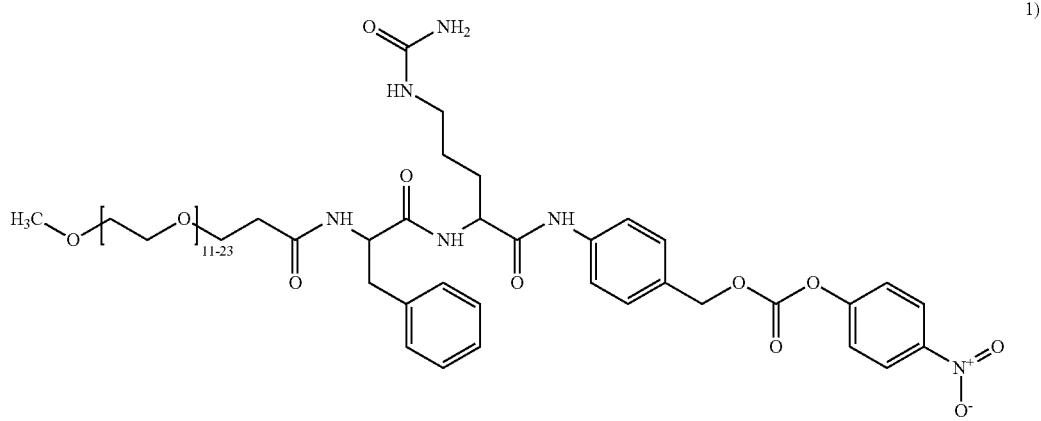

Preparation of Dipeptide Precursors:
a) Fmoc-FCit-OH

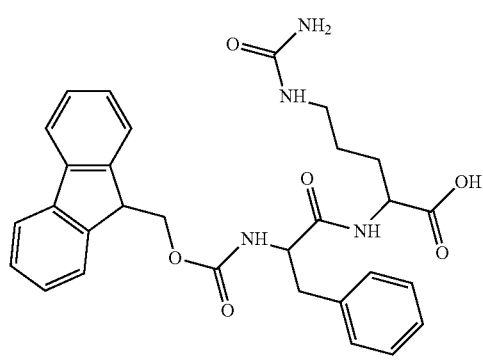 [SMILES: NC(=O)NCCCC(NC(=O)C(Cc1ccccc1)NC(=O)OCC1c2ccccc2-c2ccccc21)C(=O)O]

A solution of Fmoc-Phe-OPfp (EMD NovaBiochem 852226) (553 mg, 1 mmol) in THF (5 ml) was added to a solution of H-Cit-OH (Sigma-Aldrich C7629) (184 mg, 1.05 mmol) and NaHCO$_3$ (88.2 mg, 1.05 mmol) in H$_2$O (2.6 ml). THF (2 ml) was added to make the solution homogeneous and stirred for 10 h. THF was removed on a rotavap, the residue was diluted with H$_2$O (10 ml) and iPrOH (1 ml) and acidified to pH=1 with 3% HCl. Product was extracted 5× with 9:1 EtOAc:iPrOH solution, rinsed with a 9:1 mixture of brine:iPrOH, dried (Na$_2$SO$_4$) and concentrated and dried in vacuo. Trituration with ether afforded 313 mg of pure product (57%). Similar conditions can be used for the preparation of Fmoc-ACit-OH.

b) Fmoc-FCit-PAB-OH

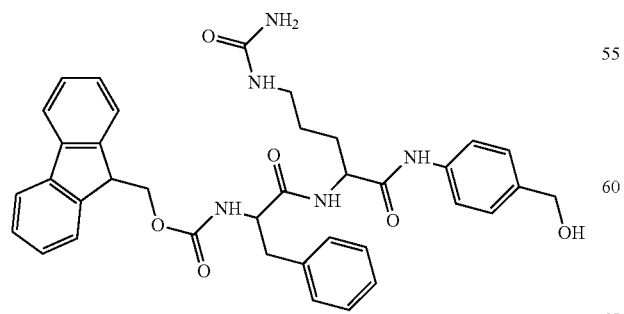

A solution of Fmoc-FCit-OH (5.98 g, 10.97 mmol) and PABA (2.70 g, 21.95 mmol) in DCM (150 ml) and MeOH (50 ml) was treated with EEDQ (5.43 g, 21.95 mmol) and let to stir at 20° C. for 15 h. All volatiles were removed on a rotavap, the residue was triturated with Et$_2$O, and product was filtered out and dried in vacuo. Yield 6.14 g (86%). Similar conditions can be used for the preparation of Fmoc-ACit-PAB-OH.

c) H$_2$N-FCit-PAB-OH (Same Conditions for Preparation of H$_2$N-A-Cit-PAB-OH)

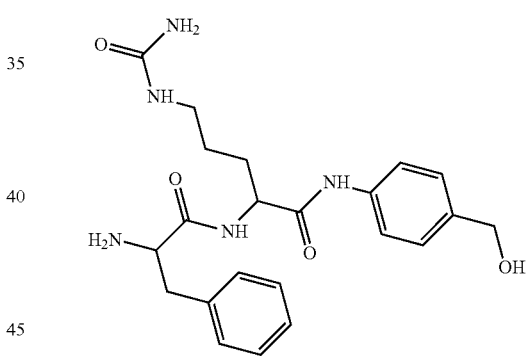

Fmoc-FCit-PAB-OH (0.83 mmol) was Fmoc deprotected by stirring with Et$_3$N (3.5 ml) in DMF (11 ml) for 10 h. All volatiles were removed on a rotavap at 40° C./oil pump vacuum to obtain crude product which was used without additional purification.

B. Preparation of PEG$_{12}$-FCit-PABC-PNP.
(FCit=Phenylalanine-Citrulline)

Quanta Biodesign Product Number: 10262

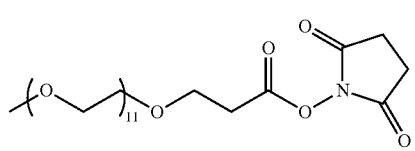

Quanta Biodesign Product Number: 10304

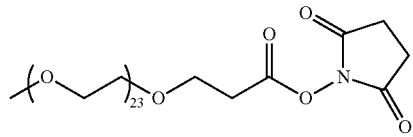

1. PEG$_{12}$-FCit-PAB-OH

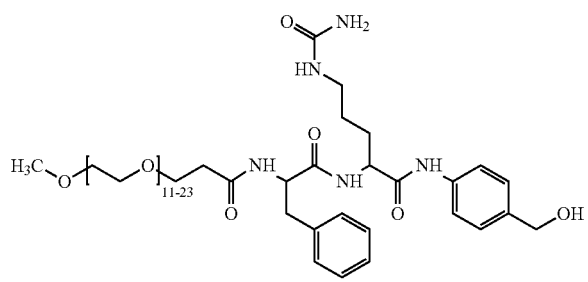

To a solution of H$_2$N-FCit-PAB-OH (0.88 mmol) and DIEA (167 μl, 0.96 mmol) in DMF (3 ml) was added a solution of PEG$_{12}$-NHS (Quanta Biodesign 10262) or PEG$_{24}$-NHS (Quanta Biodesign 10304) (0.8 mmol) in DMF (3 ml). The mixture was stirred for 16 h, filtered and concentrated. The crude was precipitated into Et$_2$O (45 ml) from CHCl$_3$:MeOH (1:1, 5 ml) and used without additional purification. Yield: 420 mg (53%).

ii) PEG$_{12}$-FCit-PABC-PNP

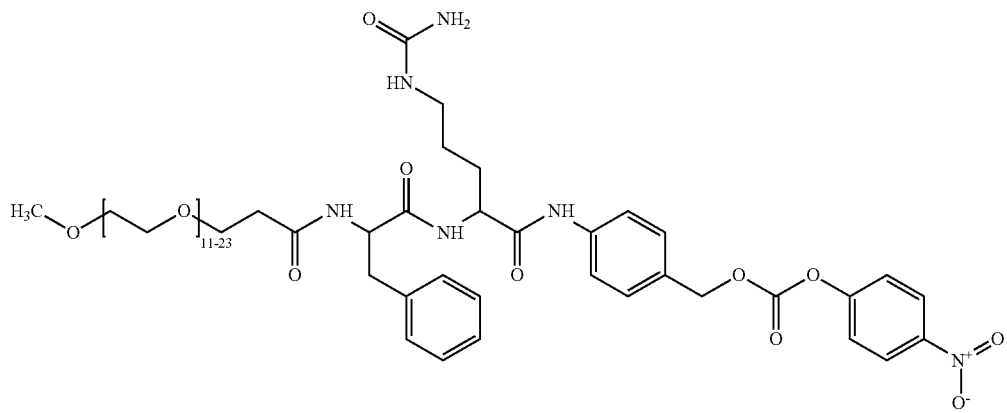

A solution containing PEG$_{12/24}$-FCit-PAB-OH (419 mg, 0.42 mmol), (PNP)$_2$CO (Sigma-Aldrich 161691) (766 mg, 2.52 mmol) and DIEA (263 μl, 1.52 mmol) in dioxane (4 ml) was stirred in the dark at 50° C. for 15 h. All volatiles were removed on a rotavap and residual DIEA was removed by evaporation from DMF. The product was purified on a column, eluent CHCl$_3$:EtOAc:MeOH=4.5:5:0.5 followed by a gradient of MeOH (12-15%) in CHCl$_3$. Yield: 390 mg (80%).

Example 24

Amphipathic Membrane Active Polyamine Syntheses

Figure 11:
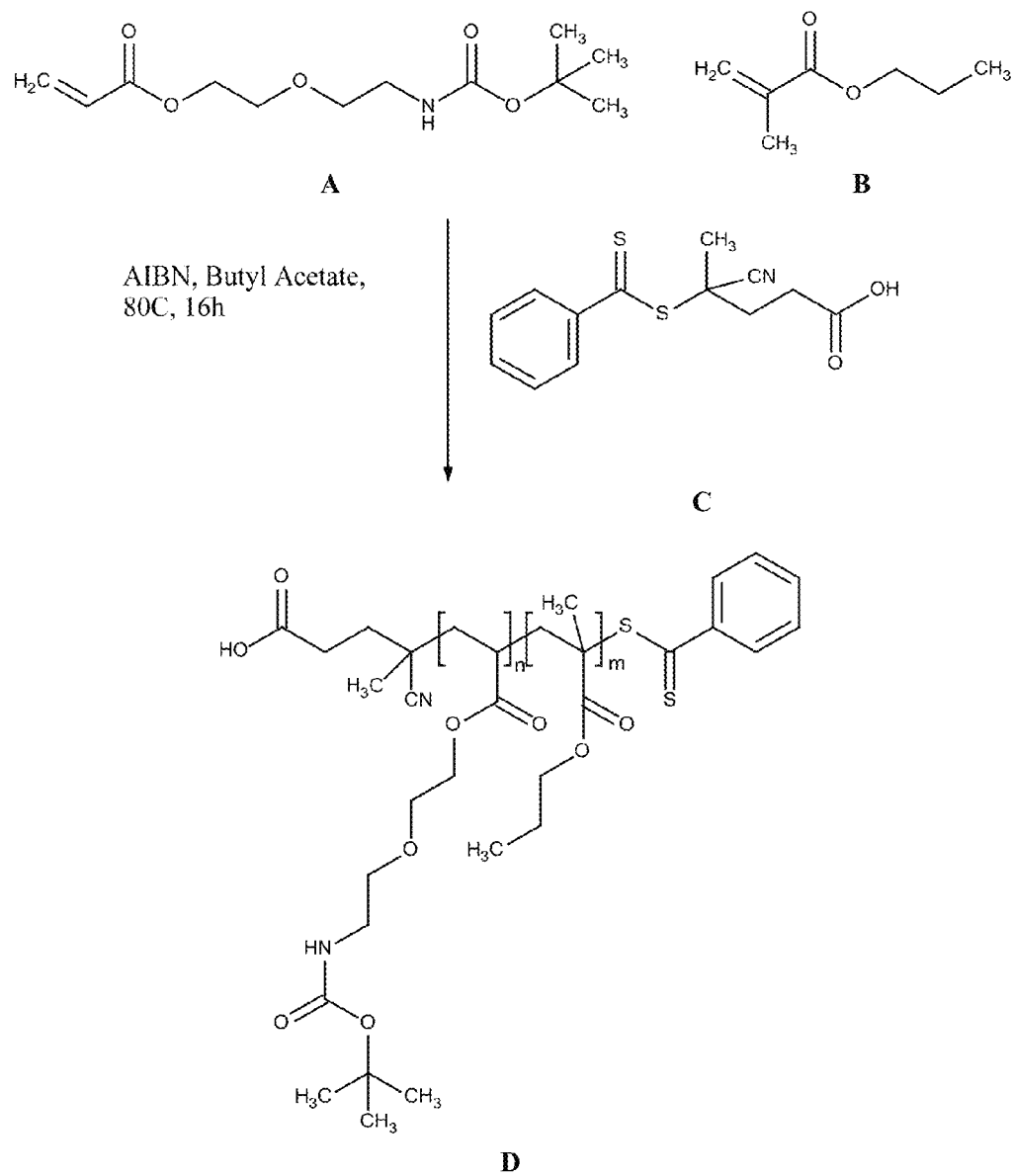
FIG. 11. Illustration showing RAFT copolymerization of N-Boc-ethylethoxy acrylate and propyl methacrylate.

A. RAFT Copolymerization of N-Boc-Ethylethoxy Acrylate and Propyl Methacrylate (FIG. 11)

For other membrane active polymers, A can be also be protected ethyl, propyl, or butyl amino acrylate. B can be higher hydrophobic (10-24 carbon atoms, C18 shown) acrylate, lower hydrophobic (1-6 carbon atoms, C4 shown) acrylate, or a combination of lower an higher hydrophobic acrylates.

Copolymers consisting of Amine acrylate/C3 methacrylate were synthesized as follows. The monomers and RAFT agent were weighed and brought up into butyl acetate at the indicated ratios. AIBN (azobis-isobutyronitrile) was added and nitrogen was bubbled through the reaction at RT for 1 h. The reaction mixture was then placed into an oil bath at 80° C. for 15 h. The polymer was then precipitated with hexane, and further fractionally precipitated using a DCM/Hexane solvent system (see below). The polymer was then dried under reduced pressure. The polymer was deprotected with 7 ml 2M HCl in Acetic Acid for 30 min at RT.

After 30 min, 15 ml of water was added to the reaction mixture, and the mixture was transferred into 3.5 kDa MWCO dialysis tubing. The polymer was dialyzed overnight against NaCl and then another day against dH$_2$O. The water was then removed through lyophilization, and the polymer was dissolved in dH$_2$O.

B. Random Copolymerization of N-Boc-Ethylethoxy Acrylate and Propyl Methacrylate Copolymers consisting of Amine acrylate/C$_n$ methacrylate were synthesized as follows. The monomers were weighed brought up into dioxane at the indicated ratios. AIBN (azobis-isobutyronitrile) was added and nitrogen was bubbled through the reaction at RT for 1 h. The reaction mixture was then placed into an oil bath at 60° C. for 3 h. The polymer was then dried under reduced pressure. The polymer was purified by GPC. After which the polymer fractions were deprotected with 7 ml 2M HCl in Acetic Acid for 30 min at RT. After 30 min, 15 ml of water was added to the reaction mixture, and the mixture was transferred into 3.5 kDa MWCO dialysis tubing. The polymer was dialyzed overnight against NaCl and then another day against dH$_2$O. The water was then removed through lyophilization, and the polymer was dissolved in dH$_2$O.

C. Synthesis of Water-Soluble, Amphipathic, Membrane Active Poly(Vinyl Ether)Polyamine Terpolymers X mol % amine-protected vinylether (e.g., 2-Vinyloxy Ethyl Phthalimide) is added to an oven dried round bottom flask under a blanket of nitrogen in anhydrous dichloromethane. To this solution Y mol % lower hydrophobic group (e.g., propyl, butyl) vinylether and optionally Z mol % higher hydrophobic group (e.g., dodecyl, octadecyl) vinylether are added (FIG. 1). The solution is placed in a −50 to −78° C. bath, and the 2-vinyloxy ethyl phthalimide is allowed to precipitate. To this solution 10 mol % BF$_3$.(OCH$_2$CH$_3$)$_2$ is added and the reaction is allowed to proceed for 2-3 h at −50 to −78° C. Polymerization is terminated by addition of ammonium hydroxide in methanol solution. The polymer is brought to dryness under reduced pressure and then brought up in 1,4-dioxane/methanol (2/1). 20 mol eq. of hydrazine per phthalimide is added to remove the protecting group from the amine. The solution is refluxed for 3 h and then brought to dryness under reduced pressure. The resulting solid is dissolved in 0.5 mol/L HCl and refluxed for 15-min to form the hydrochloride salt of the polymer, diluted with distilled water, and refluxed for an additional hour. The solution is then neutralized with NaOH, cooled to RT, transferred to molecular cellulose tubing, dialyzed against distilled water, and lyophilized. The polymer can be further purified using size exclusion or other chromatography. The molecular weight of the polymers is estimated using columns according to standard procedures, including analytical size-exclusion chromatography and size-exclusion chromatography with multi-angle light scattering (SEC-MALS).

D. Polymer Ant-41658-111

1) Monomer Synthesis.

2,2′-Azobis(2-methylpropionitrile) (AIBN, radical initiator), 4-Cyano-4-(phenylcarbonothioylthio)pentanoic acid (CPCPA, RAFT Agent) and butyl acetate were purchased from Sigma Aldrich. Propyl Methacrylate monomer (Alfa Aesar) was filtered to remove inhibitors.

In a 2 L round-bottom flask equipped with a stir bar, 2-(2-aminoethoxy) ethanol (21.1 g, 202.9 mmol, Sigma Aldrich) was dissolved in 350 ml dichloromethane. In a separate 1 L flask, BOC anhydride (36.6 g, 169.1 mmol) was dissolved in 660 ml dichloromethane. The 2 L round-bottom flask was fitted with an addition funnel and BOC anhydride solution was added to the flask over 6 h. The reaction was left to stir overnight. In a 2 L separatory funnel, the product was washed with 300 ml each of 10% citric acid, 10% K$_2$CO$_3$, sat. NaHCO$_3$, and sat. NaCl. The product, BOC protected 2-(2-aminoethoxy)ethanol, was dried over Na$_2$SO$_4$, gravity filtered, and DCM was evaporated using rotary evaporation and high vacuum.

In a 500 ml round bottom flask equipped with a stir bar and flushed with argon, BOC protected 2-(2-aminoethoxy) ethanol (27.836 g, 135.8 mmol) was added, followed by 240 ml anhydrous dichloromethane. Diisopropylethyl amine (35.5 ml, 203.7 mmol) was added, and the system was placed in a dry ice/acetone bath. Acryloyl Chloride (12.1 ml, 149.4 mmol) was diluted using 10 ml of dichloromethane, and added drop-wise to the argon flushed system. The system was kept under argon and left to come to RT and stirred overnight. The product was washed with 100 ml each of dH$_2$O, 10% citric acid, 10% K$_2$CO$_3$, sat. NaHCO$_3$, and saturated NaCl. The product, BOC-amino ethyl ethoxy acrylate (BAEEA), was dried over Na$_2$SO$_4$, gravity filtered, and DCM was evaporated using rotary evaporation. The product was purified through column chromatography on 29 cm silica using a 7.5 cm diameter column. The solvent system used was 30% ethyl acetate in hexane. Rf: 0.30. Fractions were collected and solvent was removed using rotary evaporation and high vacuum. BAEEA, was obtained with 74% yield. BAEEA was stored in the freezer.

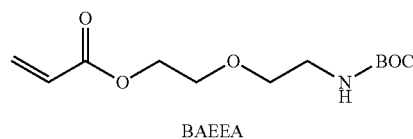 [SMILES: C=CC(=O)OCCOCCNC(=O)OC(C)(C)C]

BAEEA

2) Polymerization:

Solutions of AIBN (1.00 mg/ml) and RAFT agent (4-Cyano-4(phenylcarbonothioylthio)pentanoic acid (CP-CPA), 10.0 mg/ml) in butyl acetate were prepared. Monomer molar feed ratio was 75 BAEEA:25 propyl methacrylate (CAS: 2210-28-8) with 0.108 CPCPA RAFT agent and 0.016 AIBN catalyst (0.00562 total mol).

BAEEA (1.09 g, 4.21 mmol) (A), propyl methacrylate (0.180 g, 1.41 mmol) (B), CPCPA solution (0.170 ml, 0.00609 mmol) (C), AIBN solution (0.150 ml, 0.000915 mmol), and butyl acetate (5.68 ml) were added to a 20 ml glass vial with stirrer bar. The vial was sealed with a rubber cap and the solution was bubbled with nitrogen using a long syringe needle with a second short syringe needle as the outlet for 1 h. The syringe needles were removed and the system was heated to 80° C. for 15 h using an oil bath. The solution was allowed to cool to RT and transferred to a 50 ml centrifuge tube before hexane (35 ml) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 ml), precipitated in hexane (35 ml) and centrifuged once more. The supernatant was decanted and the bottom layer rinsed with hexane before the polymer was dried under reduced pressure for several hours. Molecular weight obtained through MALS: 73,000 (PDI 1.7); Polymer composition obtained using H$^1$NMR: 69:31 Amine:Alkyl.

Fractional Precipitation.

The dried, precipitated product was dissolved in DCM (100 mg/ml). Hexane was added until just after the cloud point was reached (~20 ml). The resulting milky solution was centrifuged. The bottom layer (thick liquid representing ~60% of polymer) was extracted and fully precipitated into hexane. The remaining upper solution was also fully precipitated by further addition of hexane. Both fractions were centrifuged, after which the polymer was isolated and dried under vacuum. Fraction 1: Mw 87,000 (PDI 1.5); Fraction 2: Mw 52,000 (PDI 1.5-1.6).

MALS Analysis.

Approximately 10 mg of the polymer was dissolved in 0.5 ml 89.8% dichloromethane, 10% tetrahydrofuran, 0.2% triethylamine. The molecular weight and polydispersity (PDI) were measured using a Wyatt Helos II multiangle light scattering detector attached to a Shimadzu Prominence HPLC using a Jordi 5μ 7.8×300 Mixed Bed LS DVB column. Crude Polymer: MW: 73,000 (PDI 1.7), Fraction 1: MW 87,000 (PDI: 1.5), Fraction 2: MW 52,000 (PDI 1.5-1.6)

The purified BOC-protected polymer was reacted 2M HCl in Acetic Acid (7 ml) for 0.5 h to remove the BOC protecting groups and produce the amines. 15 ml dH$_2$O were added to the reaction, the solution was transferred to 3500 MW cutoff cellulose tubing, dialyzed against high salt for 24 h, then against dH$_2$O for 18 h. The contents were lyophilized, then dissolved in DI H$_2$O at a concentration of 20 mg/ml. The polymer solution was stored at 2-8° C.

E. Polymer Lau24B was prepared as above except the monomer feed ratio was 72.5 BAEEA:27.5 propyl methacrylate.

F. Ant-129-1 was made as essentially as described above except the following monomers were used:

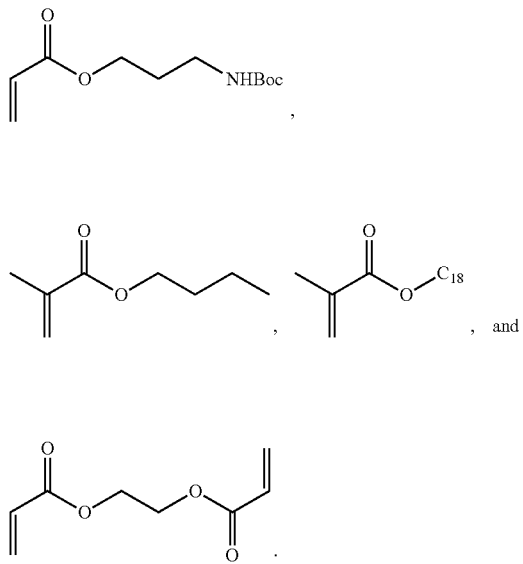

For N-Boc-Amino-Propyl-Acrylate (BAPA), In a 500 ml round bottom flask equipped with a stir bar and flushed with argon, 3-(BOC-amino)1-propanol (TCI) (135.8 mmol) was added, followed by 240 ml anhydrous dichloromethane. Diisopropylethyl amine (203.7 mmol) was added, and the system was placed in a dry ice/acetone bath. Acryloyl Chloride (149.4 mmol) was diluted using 10 ml of dichloromethane, and added drop-wise to the argon flushed system. The system was kept under argon and left to come to RT and stirred overnight. The product was washed with 100 ml each of dH$_2$O, 10% citric acid, 10% K$_2$CO$_3$, sat. NaHCO$_3$, and saturated NaCl. The product, BOC-amino propyl acrylate (BAPA), was dried over Na$_2$SO$_4$, gravity filtered, and DCM was evaporated using rotary evaporation. The product was purified through column chromatography on 29 cm silica using a 7.5 cm diameter column. The solvent system used was 30% ethyl acetate in hexane. Rf: 0.30. Fractions were collected and solvent was removed using rotary evaporation and high vacuum. BAPA was obtained with 74% yield. BAPA was stored in the freezer.

G. Polymer Lau41648-106

Monomer molar feed ratio was 80 BAEEA:20 propyl methacrylate (CAS:2210-28-8) and 3% AIBN catalyst based on total monomer moles. BAEEA (6.53 g, 25.2 mmol) (A), propyl methacrylate (0.808 g, 6.3 mmol) (B), AIBN (0.155 g, 0.945 mmol), and dioxane (34.5 ml) were added to a 50 ml glass tube with stir bar. Compounds A and B were prepared described above in Example 16Ai. The reaction was set up in triplicate. Each solution was bubbled with nitrogen using a long pipette for 1 h. The pipette was removed and each tube carefully capped. Then each solution was heated at 60° C. for 3 h using an oil bath. Each solution was allowed to cool to RT and combined in a round bottom. The crude polymer was dried under reduced pressure. Molecular weight obtained through MALS: 55,000 (PDI 2.1); Polymer composition obtained using H$^1$NMR: 74:26 Amine:Alkyl.

TABLE 10

Ant-129-1 polymer synthesis reactants.

| | MW (g/mol) | mol % | moles | mass (g) | volume (ml) | reaction moles |
|---|---|---|---|---|---|---|
| Monomers | | | | | | |
| N-Boc-amino-propyl acrylate | 229.27 | 70 | 3.94 × 10$^{-3}$ | 0.9031 | | 0.005627 |
| butyl methacrylate | 142.2 | 25 | 1.41 × 10$^{-3}$ | 0.2000 | 0.224 | 0.005627 |
| C18 methacrylate | 338.54 | 5 | 2.81 × 10$^{-4}$ | 0.0952 | | 0.005627 |
| ethylene glycol diacrylate | 170.16 | 5 | 2.81 × 10$^{-4}$ | 0.0479 | 0.44 | 0.005627 |
| other reagents | | | | | | |
| CPCPA (RAFT reagent) | 279.38 | 0.213 | 1.2 × 10$^{-5}$ | 0.0033 | 0.335 | 0.005627 |
| AIBN (initiator) | 164.21 | 0.032 | 1.8 × 10$^{-6}$ | 0.0003 | 0.295 | 0.005627 |
| butyl acetate | | | | | 5.272 | |
| target molecular weight | 100000 | | | | | |
| total units per CTA | 469.56 | | | | | |
| % CTA | | 0.213 | | | | |

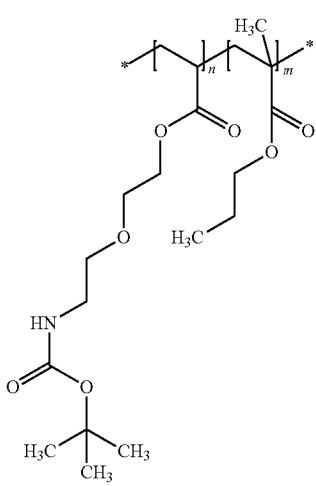

Lau41648-106

GPC Fractionation.

The dried crude polymer was brought up at 50 mg/ml in 75% dichloromethane, 25% tetrahydrafuran, and 0.2% triethylamine. The polymer was then fractionated on a Jordi Gel DVB $10^4$ Å-500 mm/22 mm column using a flow rate of 5 ml/min and 10 ml injections. An earlier fraction was collected from 15-17 min, and a later fraction was collected from 17-19 min. Fraction 15-17: Mw 138,000 (PDI 1.1); Fraction 17-19: Mw 64,000 (PDI 1.2).

MALS Analysis.

Approximately 10 mg of the polymer was dissolved in 0.5 ml 89.8% dichloromethane, 10% tetrahydrofuran, 0.2% triethylamine. The molecular weight and polydispersity (PDI) were measured using a Wyatt Helos II multiangle light scattering detector attached to a Shimadzu Prominence HPLC using a Jordi 5µ 7.8×300 Mixed Bed LS DVB column. Crude Polymer: MW: 55,000 (PDI 2.1), Fraction 15-17: MW 138,000 (PDI: 1.1), Fraction 17-19: MW 64,000 (PDI 1.2)

The purified BOC-protected polymer was reacted 2M HCl in Acetic Acid (7 ml) for 0.5 h to remove the BOC protecting groups and produce the amines. 15 ml $dH_2O$ were added to the reaction, the solution was transferred to 3500 MW cutoff cellulose tubing, dialyzed against high salt for 24 h, then against $dH_2O$ for 18 h. The contents were lyophilized, then dissolved in DI $H_2O$ at a concentration of 20 mg/ml. The polymer solution was stored at 2-8° C.

H. Polymer DW1360

An amine/butyl/octadecyl poly(vinyl ether) terpolymer, was synthesized from 2-vinyloxy ethyl phthalimide (5 g, 23.02 mmol), butyl vinylether (0.665 g, 6.58 mmol), and octadecyl vinylether (0.488 g, 1.64 mmol) monomers. 2-vinyloxy ethyl phthalimide was added to a 200 ml oven dried round bottom flask containing a magnetic stir bar under a blanket of Argon in 36 ml anhydrous dichloromethane. To this solution was added butyl vinyl ether and n-octadecyl vinyl ether. The monomers were fully dissolved at RT (RT) to obtain a clear, homogenous solution. The reaction vessel containing the clear solution was then placed into a -50° C. bath generated by addition of dry ice to a 1:1 solution of ACS grade denatured alcohol and ethylene glycol and a visible precipitation of phthalimide monomer was allowed to form. After cooling for about 1.5 min, $BF_3.(OCH_2CH_3)_2$ (0.058 g, 0.411 mmol) was added to initiate the polymerization reaction. The phthalimide monomer dissolved upon initiation of polymerization. The reaction was allowed to proceed for 3 h at -50° C. The polymerization was stopped by the addition of 5 ml of 1% ammonium hydroxide in methanol. The solvents were then removed by rotary evaporation.

The polymer was then dissolved in 30 ml of 1,4-dioxane/methanol (2/1). To this solution was added hydrazine (0.147 g, 46 mmol) and the mixture was heated to reflux for 3 h. The solvents were then removed by rotary evaporation and the resulting solid was then brought up in 20 ml of 0.5 mol/L HCl and refluxed for 15 min, diluted with 20 ml distilled water, and refluxed for an additional hour. This solution was then neutralized with NaOH, cooled to RT, transferred to 3,500 molecular weight cellulose tubing, dialyzed for 24 h (2×20 L) against distilled water, and lyophilized.

I. Polymer Emi 1034-68C

Monomer molar feed ratio was 52.5 BAEAA:47.5 propyl acrylate (CAS: 925-60-0) and 6.66:1 ratio of CTA (CPCPA) to Initiator (AIBN). BAEAA (2.6851 g, 10.35 mmol), propyl acrylate (1.0742 g, 9.41 mmol), CPCPA (0.0105 g, 0.0375 mmol), AIBN (0.000924 g, 0.00563 mmol), and butyl acetate (15.9 ml) were added to a 40 ml glass vial with stir bar. The solution was bubbled with nitrogen using a long hypodermic needle in a septum cap for 1 h. The needle was removed and the solution was heated at 80° C. for 16 h using an oil bath. Each solution was allowed to cool to RT. The crude polymer was precipitated out using hexane (~8× vol.) and centrifuged. The solvent was decanted and the polymer was rinsed with hexane and dissolved in DCM. The dissolved polymer was precipitated again with hexane (~8× vol.). After centrifugation, the solvent was decanted and the polymer was dried under reduced pressure. Molecular weight obtained through MALS: 59,640 (PDI 1.328); Polymer composition obtained using $H^1NMR$: 55.4:44.6 Amine: Alkyl.

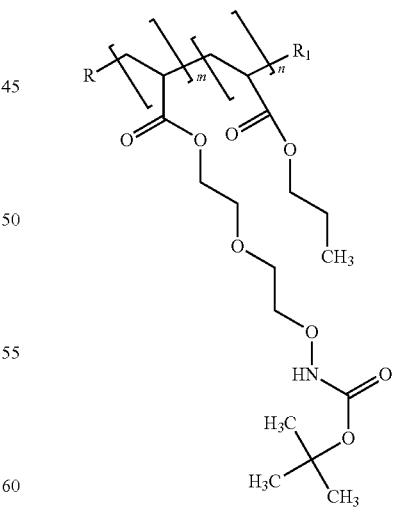

Fractional Precipitation.

In a 50 ml centrifuge tube, samples were dissolved in 60% heptane/40% dioxane at 25 mg sample/ml solvent using sonication. The samples were vortexed for 10 seconds and allowed to sit for 4 h. The solvent was pipetted off the top and the polymer that precipitated out was rinsed twice with hexane. The samples were dried using high vacuum.

MALS Analysis.

A small amount of the polymer was dissolved at 10 mg/ml in 75% DCM, 20% THF, and 5% ACN. The molecular weight and polydispersity (PDI) were measured using a Wyatt Helos II multiangle light scattering detector attached to a Shimadzu Prominence HPLC using a Phenogel 5μ Linear(2) 7.8×300 column. Crude Polymer: MW: 59,640 (PDI 1.328), Fraction 1: MW 80,540 (PDI: 1.120).

Boc-Deprotection.

The purified BOC-protected polymer was reacted 2M HCl in Acetic Acid (7 ml) for 0.5 h to remove the BOC protecting groups and produce the amines. 15 ml dH$_2$O were added to the reaction, the solution was transferred to 3500 MW cutoff cellulose tubing, dialyzed against high salt for 24 h, then against dH$_2$O for 18 h. The contents were lyophilized, then dissolved in DI H$_2$O at a concentration of 20 mg/ml. The polymer solution was stored at 2-8° C.

J. Polymer Emi1034-81F

Monomer molar feed ratio was 65 BAEAA:35 butyl acrylate (CAS: 141-32-2) and 6.66:1 ratio of CTA (CPCPA) to Initiator (AIBN). BAEAA (0.9876 g, 3.809 mmol), butyl acrylate (0.2607 g, 2.034 mmol), CPCPA (0.0035 g, 0.0125 mmol), AIBN (0.000308 g, 0.00188 mmol), and butyl acetate (5.3 ml) were added to a 20 ml glass vial with stir bar. The solution was bubbled with nitrogen using a long hypodermic needle in a septum cap for 1 h. The needle was removed and the solution was heated at 80° C. for 16 h using an oil bath. Each solution was allowed to cool to RT. The crude polymer was precipitated out using hexane (~8× vol.) and centrifuged. The solvent was decanted and the polymer was rinsed with hexane and dissolved in DCM. The dissolved polymer was precipitated again with hexane (~8× vol.). After centrifugation, the solvent was decanted and the polymer was dried under reduced pressure. Molecular weight obtained through MALS: 63,260 (PDI 1.318); Polymer composition obtained using H$^1$NMR: 68.7:31.3 Amine:Alkyl.

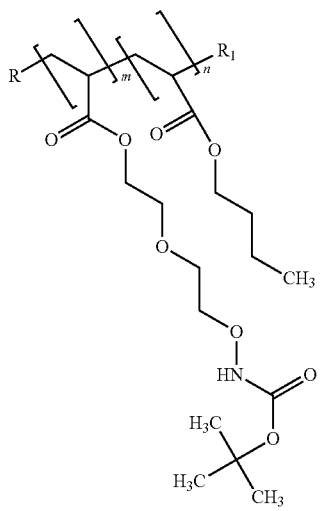

Fractional Precipitation.

In a 50 ml centrifuge tube, samples were dissolved in 60% heptane/40% dioxane at 25 mg sample/ml solvent using sonication. The samples were vortexed for 10 seconds and allowed to sit for 4 h. The solvent was pipetted off the top and the polymer that precipitated out was rinsed twice with hexane. The samples were dried using high vacuum.

MALS Analysis.

A small amount of the polymer was dissolved at 10 mg/ml in 75% DCM, 20% THF, and 5% ACN. The molecular weight and polydispersity (PDI) were measured using a Wyatt Helos II multiangle light scattering detector attached to a Shimadzu Prominence HPLC using a Phenogel 5μ Linear(2) 7.8×300 column. Crude Polymer: MW: 63,260 (PDI 1.318), Fraction 1: MW 65,990 (PDI: 1.246).

Boc-Deprotection.

The purified BOC-protected polymer was reacted 2M HCl in Acetic Acid (7 ml) for 0.5 h to remove the BOC protecting groups and produce the amines. 15 ml dH$_2$O were added to the reaction, the solution was transferred to 3500 MW cutoff cellulose tubing, dialyzed against high salt for 24 h, then against dH$_2$O for 18 h. The contents were lyophilized, then dissolved in DI H$_2$O at a concentration of 20 mg/ml. The polymer solution was stored at 2-8° C.

K. Polymer LH1073-20C-1

Monomer feed ratio was 55 BAPVE (Boc-amino propyl vinyl ester):45 vinyl butyrate (CAS: 123-20-6), and 10:1 ratio of Chain Transfer Agent (MDPD) to initiator (AIBN). BAPVE (0.8 g, 3.72 mmol), MDPD (9.26 mg, 0.0229 mmol), AIBN (0.21 mg, 0.00229 mmol), and butyl acetate (0.5 ml) were added to a 20 ml glass vial with stir bar. This solution was bubbled with nitrogen using a long hypodermic needle in a septum cap for 1 h. A separate vial of excess vinyl butyrate was degassed similarly. Needles/nitrogen were removed and vinyl butyrate (0.35 g, 3.04 mmol) was added to the reaction solution with a Hamilton syringe. The solution was stirred for 4 h at 80° C. and then allowed to cool to RT. The resulting viscous solution was dissolved in 5 ml DCM and the polymer was precipitated by addition of 40 ml hexane. After centrifugation, the upper solvent was decanted and the polymer was rinsed with 5 ml of hexane. The rinsed polymer was re-dissolved in 5 ml DCM, and precipitated once more with 40 ml hexane, centrifuged, and decanted upper solvent. The polymer was then dried under high vacuum. Molecular weight obtained through MALS: 42,230 (PDI 1.205); Polymer composition obtained using H$^1$NMR: 57.5:42.5 Amine:Alkyl.

Fractional Precipitation:

In a 50 ml centrifuge tube, polymer was dissolved in 10 ml DCM and enough hexane was added to take the solution past the cloud point (approximately 30 ml). The cloudy mixture was centrifuged, forming two liquid layers. The more viscous bottom layer was removed, diluted with 5 ml DCM and fully precipitated with 40 ml of hexane to yield fraction one. After centrifugation of fraction the solvent was decanted and the polymer dried under reduced pressure. Molecular weight obtained through MALS: 61,350 (PDI 1.205).

MALS Analysis:

A small amount of the polymer was dissolved to afford a 10 mg/ml in 75% DCM, 20% THF, and 5% ACN. The molecular weight and polydispersity (PDI) were measured using a Wyatt Helos II multiangle light scattering detector attached to a Shimadzu Prominence HPLC with a Phenogel 5 u Linear (2) 7.8×300 column. See molecular weight above.

Boc-Deprotection:

The fractionated BOC-protected polymer was reacted with 2N HCl in Acetic Acid (5 ml) and stirred for 1 h to remove the BOC groups and produce the amines. The solution was diluted with water (30 ml) and dialyzed (3500 MWCO cellulose tubing) against an aqueous NaCl solution and then deionized water over two days. The contents were lyophilized, and then dissolved in DI water at a concentration of 20 mg/ml. The polymer was stored at 2-8° C.

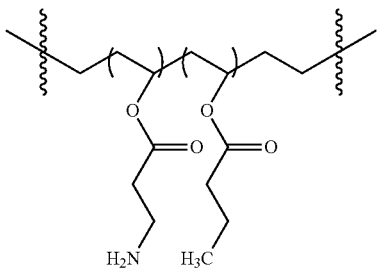

L. Melittin.

All melittin peptides were made using peptide synthesis techniques standard in the art. Suitable melittin peptides can be all L-form amino acids, all D-form amino acids (inverso). Independently of L or D form, the melittin peptide sequence can be reversed (retro).

Example 25

Terminal Polymer Modification with Azido-PEG-Amine

In a 40 ml scintillation vial equipped with a septa cap and stir bar, polymer (Emi 1034-68C class, 1 g, 0.0143 mmol) was dissolved in 20 ml anhydrous dichloromethane (Sigma). Pentafluorophenol (Sigma, 26.3 mg, 0.143 mmol) and N,N'-Dicyclohexylcarbodiimide (Sigma, 29.5 mg, 0.143 mmol) were added to the flask with stirring. Using a $N_2$ gas line and a needle for venting, the system was purged with $N_2$ for ~10 min. The reaction was left to stir at RT overnight. Additional Pentafluorophenol (Sigma, 26.3 mg, 0.143 mmol) and N,N'-Dicyclohexylcarbodiimide (Sigma, 29.5 mg, 0.143 mmol) were added to the flask, the system was purged with $N_2$ gas, and the reaction was stirred for 3 h at RT. The polymer was precipitated with hexane (~10× volume, Sigma), centrifuged, and the solvent was decanted. The polymer was dissolved in minimal dichloromethane, precipitated with hexane (10× volume), centrifuged, and the solvent was decanted. The polymer was dissolved in minimal ethyl acetate (Sigma), precipitated with hexane (~10× volume), centrifuged, and the solvent was decanted. The polymer precipitate was dried under high vacuum until the solid reached a constant weight.

Figure 12:
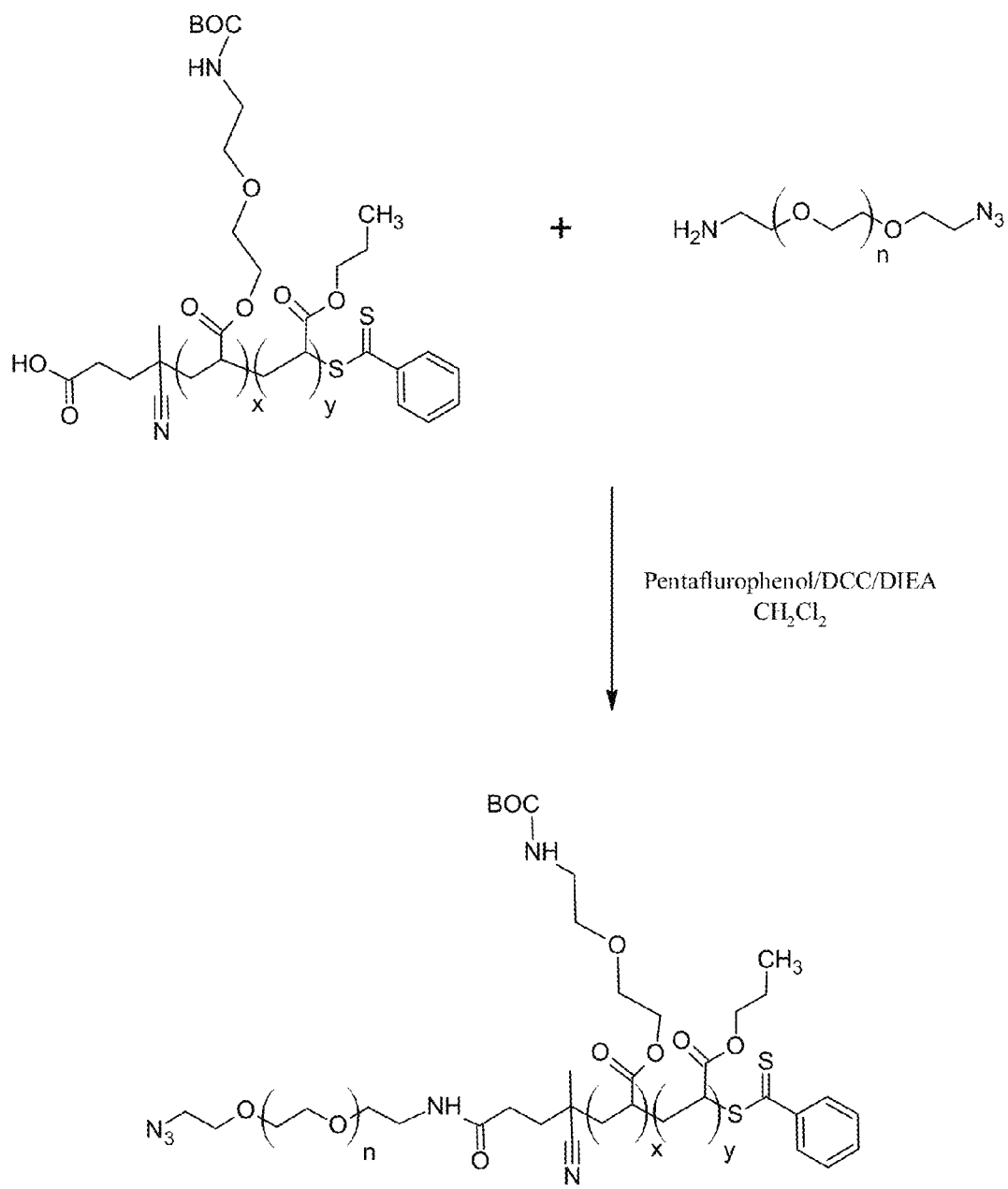
FIG. 12. Illustration showing terminal polymer modification with azido-PEG-amine.

In a 40 ml scintillation vial equipped with a septa cap and stir bar, polymer from the previous step (Emi 1034-68C class, 1 g, 0.0143 mmol) was dissolved in 20 ml anhydrous dichloromethane. Azido $PEG_4$ Amine (PurePeg, 37.5 mg, 0.143 mmol) and N,N-Diisopropylethylamine (Sigma, 20.3 mg, 0.157 mmol) were added to the flask with stirring. The system was purged with $N_2$ gas for ~10 min, and the reaction was left to stir at RT overnight. Additional Azido $PEG_4$ Amine (PurePeg, 37.5 mg, 0.143 mmol) and N,N-Diisopropylethylamine (Sigma, 20.3 mg, 0.157 mmol) were added to the flask, the system was purged with $N_2$ gas, and the reaction was stirred for 3 h at RT. The polymer was precipitated with hexane (~10× volume), centrifuged, and the solvent was decanted. The polymer was dissolved in minimal dichloromethane, precipitated with hexane (~10× volume), centrifuged, and the solvent was decanted. The polymer precipitate was dried under high vacuum until the solid reached a constant weight (FIG. 12).

We claim:

1. A compound for delivering an RNAi trigger to an integrin positive tumor cell in vivo comprising the structure represented by:

R-A$^1$A$^2$-amidobenzyl-carbamate-P-RNAi trigger wherein, R comprises an RGD mimic, A$^1$ is a hydrophobic amino acid, A$^2$ is a hydrophilic uncharged amino acid linked to A$^1$ via an amide bond, wherein said hydrophilic uncharged amino acid is uncharged at neutral pH, and P comprises a membrane active polyamine.

2. The compound of claim 1 wherein A$^1$ is selected from the group consisting of: alanine, phenylalanine, valine, leucine, isoleucine, and tryptophan.

3. The compound of claim 1 wherein A$^2$ is selected from the group consisting of: citrulline, threonine, asparagine, and glutamine.

4. The compound of claim 1 wherein the integrin is an $\alpha_v\beta_3$ integrin.

5. The compound of claim 1 wherein the R-A$^1$A$^2$-amidobenzyl-carbamate-P has the structure represented by:

[Structure diagram: R⁴-NH-CH(R¹)-C(=O)-NH-CH(R²)-C(=O)-NH-C₆H₄-CH₂-O-C(=O)-NH-polyamine]

wherein R⁴ comprises an RGD mimic, R¹ is the side group of a hydrophobic amino acid, R² is the side group of a hydrophilic uncharged amino acid and polyamine is the membrane active polyamine P.

6. The compound of claim 1 wherein the RGD mimic comprises a guanidinium group linked to a glycine-aspartate dipeptide via an amide bond.

7. The compound of claim 6 wherein the RGD mimic comprises the structure represented by:

[Structure: guanidinium-phenyl-C(=O)-NH-CH₂-C(=O)-NH-CH(CH₂COOH)-C(=O)-NH-C₆H₄-O-]

8. The compound of claim 7 wherein the guanidinium is selected from

[Structure: H₂N-C(=NH₂)-N(CH₃)- guanidinium]

and its resonance structures, or

[Structure: cyclic guanidine with N-CH₃]

and its resonance structures.

9. The compound of claim 1 wherein R comprises:

RGD mimic-PEG1-diaryl hydrazone-PEG2 wherein:
PEG1 comprises $(CH_2-CH_2-O)_n$,
PEG2 comprises $(CH_2-CH_2-O)_m$,
n and m are independently integers greater than or equal to 4,
the sum of n+m is 12-48, and RGD mimic consists of the structure represented by

[Structure: R¹⁴-C(=O)-NH-CH₂-C(=O)-NH-CH(CH₂COOH)-C(=O)-NH-C₆H₄-O-]

wherein R14 is selected from the group consisting of:

[Structure: guanidinium-substituted phenyl]

and its resonance structures, and

[Structure: tetrahydropyrimidinyl-imino-phenyl]

and its resonance structures.

10. The compound of claim 1 further comprising a polyethylene glycol linked to the membrane active polyamine via a reversible physiologically labile covalent linkage.

11. The compound of claim 10 wherein an RNAi trigger is covalently linked to the membrane active polyamine.

12. The compound of claim 11 wherein the compound has the structure represented by:

$$\begin{array}{c}(R-L^2)_y\\ \diagdown\\ P-L^1-N\\ \diagup\\ (PEG-L^2)_z\end{array}$$

wherein N is the RNAi trigger, $L^1$ is a physiologically labile linkage, PEG comprises polyethylene glycol, $L^2$ is $A^1A^2$-amidobenzyl-carbamate, y is an integer greater than zero, z is an integer greater than zero, and the value of the sum of y and z is greater than 50% of the number of amines present on membrane active polyamine P as determine by the number of amines on the unmodified membrane active polyamine.

13. The compound of claim 12 wherein P-L²-R comprises:

R-PEG'-diaryl hydrazone-PEG"-AA-amidobenzyl carbamate-polyamine wherein:
R has the structure represented by:

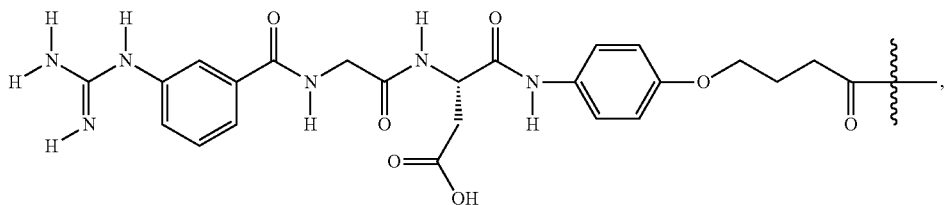 [SMILES: *C(=O)CCCOc1ccc(NC(=O)[C@H](CC(=O)O)NC(=O)CNC(=O)c2cccc(N/C(N)=N/[H])c2)cc1]

PEG' has the structure represented by:

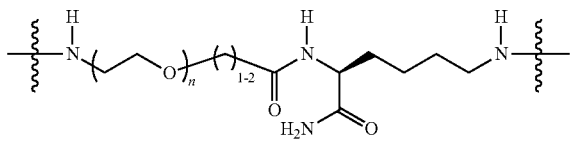

wherein n=4-44,
diaryl hydrazone has the structure represented by:

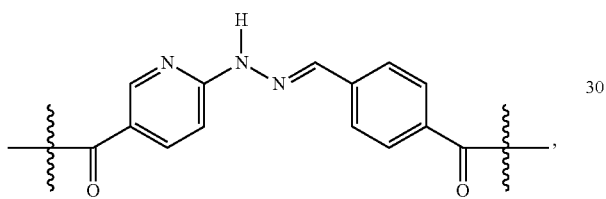

PEG" has the structure represented by:

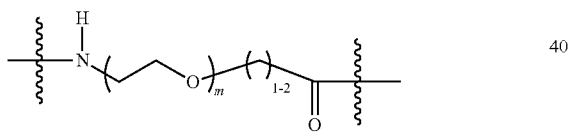

wherein m is 4-44, and
AA-amidobenzyl carbamate-polyamine has the structure represented by:

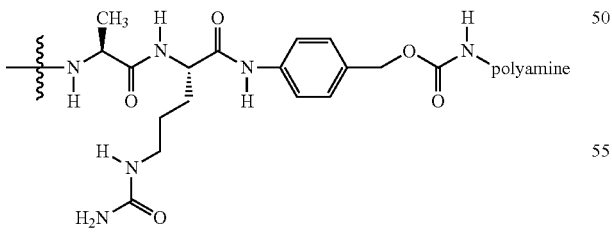

wherein polyamine is the membrane active polyamine P.

14. A method for reversibly modifying a membrane active polyamine comprising:
a) reversibly modifying one or more amines on the polyamine by reacting the one or more amines with one or more first compounds each having the structure represented by:

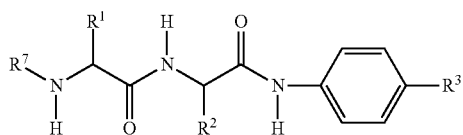

wherein $R^3$ comprises an amine reactive carbonate moiety capable of reacting with the amine to form a carbamate, $R^7$ comprises a first reactive group less amine reactive than the amine reactive carbonate, $R^1$ is a side group of a hydrophobic amino acid, $R^2$ is a side chain of a hydrophilic uncharged amino acid, and
b) reacting $R^7$ with a second compound having the structure represented by:

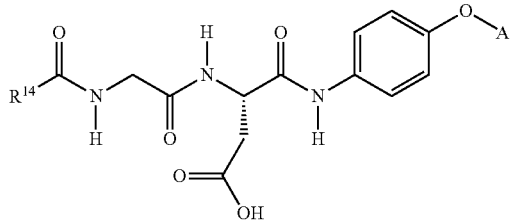

wherein $R^{14}$ is selected from the group consisting of:

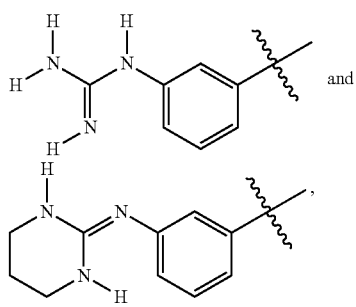

and A comprises a polyethylene glycol having 4-44 ethoxy units linked to a second reactive group capable of reacting with the first reactive group of R7 to form a covalent linkage.

15. The process of claim 14 wherein $R^7$ further comprises a polyethylene glycol group having 4 to 44 ethoxy units.

16. The process of claim 14 comprising further reversibly modifying one or more amines on the polyamine by reacting the one or more amines with a one or more compounds each having the structure represented by:

PEG-A$^1$A$^2$-amidobenzyl-carbonate

PEG comprises a polyethylene glycol, A$^1$ is a hydrophobic amino acid, A$^2$ is a hydrophilic uncharged amino acid linked to A$^1$ via an amide bond, wherein said hydrophilic uncharged amino acid is uncharged at neutral pH.

17. The process of claim 16 wherein the 80% or more of the number of amines on the polyamine are reversibly modified and the modified polyamine is not membrane active.

18. The process of claim 17 wherein an RNAi trigger molecule is covalently linked to the polyamine via a physiologically labile bond.

* * * * *

SEQUENCE LISTING

```
<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: RGD integrin binding peptide
<220> FEATURE:
<221> NAME/KEY: misc_feature
<222> LOCATION: 1, 3, 5, 9, 11, 13
<223> OTHER INFORMATION: Xaa can be any naturally occurring amino acid

<400> SEQUENCE: 1

Xaa Cys Xaa Cys Xaa Arg Gly Asp Xaa Cys Xaa Cys Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: RGD integrin binding peptide

<400> SEQUENCE: 2

Ala Cys Asp Cys Arg Gly Asp Cys Phe Cys
1               5                   10

<210> SEQ ID NO 3
```

```
<211> LENGTH: 20
<212> TYPE: DNA
<213> ORGANISM: Artificial Sequence
<220> FEATURE:
<223> OTHER INFORMATION: Mouse Aha1 siRNA sense strand sequence
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-flouro corresponding
      nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked deoxythymidine"

<400> SEQUENCE: 3
ggaugaagug gagauuagut                                                    20

<210> SEQ ID NO 4
<211> LENGTH: 21
<212> TYPE: DNA
<213> ORGANISM: Artificial Sequence
<220> FEATURE:
<223> OTHER INFORMATION: mouse Aha1 siRNA antisense strand sequence
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-flouro corresponding
      nucleoside"
<220> FEATURE:
<221> NAME/KEY: modified_base
<222> LOCATION: 2, 21
<223> OTHER INFORMATION: /mod_base = "5'-phosphorothioate nucleoside"
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
      nucleoside"

<400> SEQUENCE: 4
acuaaucucc acuucaucct t                                                  21

<210> SEQ ID NO 5
<211> LENGTH: 12
<212> TYPE: PRT
<213> ORGANISM: Artificial Sequence
<220> FEATURE:
<223> OTHER INFORMATION: RGD integrin binding peptide

<400> SEQUENCE: 5

Ala Cys Asp Cys Arg Gly Asp Cys Phe Cys Gly Lys
1               5                   10
```